US010246707B2

(12) United States Patent
Platenburg et al.

(10) Patent No.: US 10,246,707 B2
(45) Date of Patent: *Apr. 2, 2019

(54) METHOD FOR EFFICIENT EXON (44) SKIPPING IN DUCHENNE MUSCULAR DYSTROPHY AND ASSOCIATED MEANS

(71) Applicants: BioMarin Technologies B.V., Leiden (NL); Academisch Ziekenhuis Leiden, Leiden (NL)

(72) Inventors: Gerard Johannes Platenburg, Voorschoten (NL); Josephus Johannes de Kimpe, Utrecht (NL); Judith Christina Theodora van Deutekom, Dordrecht (NL); Garrit-Jan Boudewijn van Ommen, Amsterdam (NL); Annemieke Aartsma-Rus, Hoofddorp (NL)

(73) Assignees: Biomarin Technologies B.V., Leiden (NL); Academisch Ziekenhuis Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/859,598

(22) Filed: Sep. 21, 2015

(65) Prior Publication Data

US 2016/0053262 A1  Feb. 25, 2016

Related U.S. Application Data

(63) Continuation of application No. 12/992,218, filed on Nov. 11, 2010, now Pat. No. 9,139,828, which is a continuation of application No. PCT/NL2009/050258, filed on May 14, 2009.

(60) Provisional application No. 61/128,010, filed on May 15, 2008.

(30) Foreign Application Priority Data

May 14, 2008 (EP) ..................... 08156193

(51) Int. Cl.
*C12N 15/11* (2006.01)
*C12N 15/113* (2010.01)
*A61K 48/00* (2006.01)

(52) U.S. Cl.
CPC ............ *C12N 15/113* (2013.01); *A61K 48/00* (2013.01); *C12N 2310/11* (2013.01); *C12N 2310/111* (2013.01); *C12N 2310/314* (2013.01); *C12N 2310/315* (2013.01); *C12N 2310/321* (2013.01); *C12N 2310/3233* (2013.01); *C12N 2310/346* (2013.01); *C12N 2310/3513* (2013.01); *C12N 2310/3517* (2013.01); *C12N 2320/33* (2013.01)

(58) Field of Classification Search
CPC ............. C12N 15/113; C12N 2310/11; C12N 2310/3233; C12N 2320/33; C12N 15/111
See application file for complete search history.

(56) References Cited

U.S. PATENT DOCUMENTS

| | | | |
|---|---|---|---|
| 5,034,506 A | 7/1991 | Summerton et al. | 528/391 |
| 5,418,139 A | 5/1995 | Campbell | 435/7.21 |
| 5,541,308 A | 7/1996 | Hogan et al. | 536/23.1 |
| 5,593,974 A | 1/1997 | Rosenberg et al. | 514/44 |
| 5,608,046 A | 3/1997 | Cook et al. | 536/23.1 |
| 5,624,803 A | 4/1997 | Noonberg et al. | |
| 5,627,263 A | 5/1997 | Ruoslahti et al. | 530/327 |
| 5,658,764 A | 8/1997 | Pergolizzi et al. | 435/91.2 |
| 5,741,645 A | 4/1998 | Orr et al. | 435/6 |
| 5,766,847 A | 6/1998 | Jackle et al. | 435/6 |
| 5,853,995 A | 12/1998 | Lee | 435/6 |
| 5,869,252 A | 2/1999 | Bouma et al. | 435/6 |
| 5,916,808 A | 6/1999 | Kole et al. | 435/375 |
| 5,962,332 A | 10/1999 | Singer et al. | 436/94 |
| 5,968,909 A | 10/1999 | Agrawal et al. | 514/44 |
| 5,976,879 A | 11/1999 | Kole et al. | 435/375 |
| 6,124,100 A | 9/2000 | Jin | 435/6 |
| 6,130,207 A | 10/2000 | Dean et al. | 514/44 |
| 6,133,031 A | 10/2000 | Monia et al. | 435/375 |
| 6,165,786 A | 12/2000 | Bennett et al. | |
| 6,172,208 B1 | 1/2001 | Cook | 536/23.1 |
| 6,172,216 B1 | 1/2001 | Bennett et al. | 536/24.5 |
| 6,210,892 B1 | 4/2001 | Bennett et al. | 435/6 |
| 6,251,589 B1 | 6/2001 | Tsuji et al. | 435/6 |
| 6,280,938 B1 | 8/2001 | Ranum et al. | 435/6 |
| 6,300,060 B1 | 10/2001 | Kantoff et al. | 435/6 |
| 6,322,978 B1 | 11/2001 | Kahn et al. | 435/6 |
| 6,329,501 B1 | 12/2001 | Smith et al. | 530/329 |

(Continued)

FOREIGN PATENT DOCUMENTS

| | | | | |
|---|---|---|---|---|
| CA | 2 319 149 | 10/2001 | ............. | C07H 21/00 |
| CA | 2 526 893 | 11/2004 | ......... | A61K 31/7088 |
| EP | 0 438 512 | 7/1991 | ............... | C12Q 1/68 |
| EP | 0 558 697 | 9/1993 | ............. | A61K 48/00 |
| EP | 0 614 977 | 9/1994 | ............. | C12N 15/12 |
| EP | 1 015 628 | 1/1998 | ............... | C12Q 1/68 |
| EP | 0 850 300 | 7/1998 | ............. | C12N 15/11 |
| EP | 1 054 058 | 5/2000 | ............. | C12N 15/11 |
| EP | 1 133 993 | 9/2001 | ............. | A61K 38/17 |

(Continued)

OTHER PUBLICATIONS

Kneppers et al., Point mutation screening for 16 exons of the dystrophin gene by multiplex single-strand conformation polymorphism analysis, 1995, Human Mutation, vol. 5, pp. 235-242.*

(Continued)

*Primary Examiner* — Dana H Shin
(74) *Attorney, Agent, or Firm* — Jones Day

(57) ABSTRACT

The invention relates to a nucleic acid molecule that binds and/or is complementary to the nucleotide molecule having sequence 5'-GUGGCUAACAGAAGCU (SEQ ID NO 1) and to its use in a method for inducing skipping of exon 44 of the DMD gene in a DMD patient.

12 Claims, 3 Drawing Sheets

Specification includes a Sequence Listing.

(56) References Cited

U.S. PATENT DOCUMENTS

| | | |
|---|---|---|
| 6,355,481 B1 | 3/2002 | Li et al. .................... 435/331 |
| 6,355,690 B1 | 3/2002 | Tsuji ........................ 514/706 |
| 6,369,038 B1 | 4/2002 | Blumenfeld et al. ........ 514/44 |
| 6,379,698 B1 | 4/2002 | Leamon ...................... 424/450 |
| 6,399,575 B1 | 6/2002 | Smith et al. ................ 514/16 |
| 6,514,755 B1 | 2/2003 | Ranum et al. ............ 435/320.1 |
| 6,623,927 B1 | 9/2003 | Brahmachari et al. ........ 435/6 |
| 6,653,466 B2 | 11/2003 | Matsuo .................... 536/24.3 |
| 6,653,467 B1 | 11/2003 | Matsuo et al. ............. 536/24.5 |
| 6,670,461 B1 | 12/2003 | Wengel et al. ............. 536/23.1 |
| 6,727,355 B2 | 4/2004 | Matsuo et al. ............. 536/24.5 |
| 6,794,192 B2 | 9/2004 | Parums et al. ............ 436/15 |
| 6,902,896 B2 | 6/2005 | Ranum et al. ............. 435/6 |
| 6,982,150 B2 | 1/2006 | Sheetz et al. .............. 435/7.2 |
| 7,001,994 B2 | 2/2006 | Zhu ........................ 536/4.1 |
| 7,034,009 B2 | 4/2006 | Pavco et al. .............. 514/44 |
| 7,118,893 B2 | 10/2006 | Ranum et al. ............. 435/91.2 |
| 7,189,530 B2 | 3/2007 | Botstein et al. ............ 435/69.1 |
| 7,202,210 B2 | 4/2007 | Wolfman et al. ........... 514/12 |
| 7,250,404 B2 | 7/2007 | Felgner et al. ............. 514/44 |
| 7,355,018 B2 | 4/2008 | Glass ...................... 530/399 |
| 7,405,193 B2 | 7/2008 | Lodish et al. ............. 514/2 |
| 7,442,782 B2 | 10/2008 | Ranum et al. ............. 536/23.1 |
| 7,514,551 B2 | 4/2009 | Rabbani et al. ............ 536/26.6 |
| 7,534,879 B2 | 5/2009 | van Deutekom ............ 536/24.5 |
| 7,589,189 B2 | 9/2009 | Ichiro et al. ............... 536/24.5 |
| 7,655,785 B1 | 2/2010 | Bentwich .................. 536/24.1 |
| 7,771,727 B2 | 8/2010 | Fuselier et al. ............ 424/185.1 |
| 7,807,816 B2 | 10/2010 | Wilton et al. ............. 536/24.5 |
| 7,902,160 B2 | 3/2011 | Matsuo et al. ............. 514/44 |
| 7,960,541 B2 | 6/2011 | Wilton et al. ............. 536/24.5 |
| 7,973,015 B2 | 7/2011 | Van Ommen et al. |
| 8,084,601 B2 | 12/2011 | Popplewell et al. |
| 8,232,384 B2 | 7/2012 | Wilton et al. ............. 536/24.5 |
| 8,263,760 B2 | 9/2012 | De Kimpe et al. |
| 8,268,962 B2 | 9/2012 | Heemskerk et al. |
| 8,304,398 B2 | 11/2012 | 'T Hoen et al. |
| 8,324,371 B2 | 12/2012 | Popplewell et al. ........ 536/24.5 |
| 8,361,979 B2 | 1/2013 | Aartsma-Rus et al. |
| 8,450,474 B2 | 5/2013 | Wilton et al. ............. 536/24.5 |
| 8,455,634 B2 | 6/2013 | Wilton et al. ............. 536/24.5 |
| 8,455,635 B2 | 6/2013 | Wilton et al. ............. 536/24.5 |
| 8,455,636 B2 | 6/2013 | Wilton et al. ............. 536/24.5 |
| 8,476,423 B2 | 7/2013 | Wilton et al. ............. 536/24.5 |
| 8,486,907 B2 | 7/2013 | Wilton et al. ............. 514/44 |
| 8,519,097 B2 | 8/2013 | Heemskerk et al. |
| 8,524,880 B2 | 9/2013 | Wilton et al. ............. 536/24.5 |
| 8,609,065 B2 | 12/2013 | Kuik-Romeijn et al. |
| 8,637,483 B2 | 1/2014 | Wilton et al. ............. 514/44 |
| 8,759,507 B2 | 6/2014 | Van Deutekom et al. |
| 8,802,645 B2 | 8/2014 | Van Ommen et al. |
| 9,079,934 B2 | 7/2015 | Watanabe et al. |
| 9,139,828 B2 | 9/2015 | Platenburg et al. . C12N 15/113 |
| 9,243,026 B2 | 1/2016 | Matsuo et al. ........ C07H 21/04 |
| 9,243,245 B2 | 1/2016 | De Kimpe et al. |
| 9,499,818 B2 | 11/2016 | Van Deutekom et al. |
| 9,528,109 B2 | 12/2016 | De Kimpe et al. |
| 2001/0056077 A1 | 12/2001 | Matsuo .................... 514/44 |
| 2002/0049173 A1 | 4/2002 | Bennett et al. ............ 514/44 |
| 2002/0055481 A1 | 5/2002 | Matsuo et al. ............. 514/44 |
| 2002/0115824 A1 | 8/2002 | Engler et al. ............. 530/524 |
| 2002/0165150 A1 | 11/2002 | Ben-Sasson ............... 514/12 |
| 2003/0045488 A1 | 3/2003 | Brown et al. |
| 2003/0073215 A1 | 4/2003 | Baker et al. ............... 435/183 |
| 2003/0082763 A1 | 5/2003 | Baker et al. ............... 435/183 |
| 2003/0082766 A1 | 5/2003 | Baker et al. ............... 435/183 |
| 2003/0109476 A1 | 6/2003 | Kmiec et al. .............. 514/44 |
| 2003/0124523 A1 | 7/2003 | Asselbergs et al. ......... 435/6 |
| 2003/0134790 A1 | 7/2003 | Langenfeld ............... 514/12 |
| 2003/0175389 A1 | 9/2003 | Shaposhnikov ............ 426/106 |
| 2003/0235845 A1 | 12/2003 | van Ommen et al. ....... 435/6 |
| 2003/0236214 A1 | 12/2003 | Wolff et al. ............... 514/44 |
| 2004/0101852 A1 | 5/2004 | Bennett et al. ............ 435/6 |
| 2004/0132684 A1 | 7/2004 | Sampath et al. ........... 514/44 |
| 2004/0226056 A1 | 11/2004 | Roch et al. ............... 800/12 |
| 2004/0266707 A1* | 12/2004 | Leake .................. C12N 15/111 |
| | | 514/44 A |
| 2005/0048495 A1 | 3/2005 | Baker et al. |
| 2005/0096284 A1 | 5/2005 | McSwiggen .................... 514/44 |
| 2005/0222009 A1 | 10/2005 | Lamensdorf et al. ............ 514/7 |
| 2005/0246794 A1 | 11/2005 | Khvorova et al. ............ 800/286 |
| 2005/0277133 A1 | 12/2005 | McSwiggen ..................... 435/6 |
| 2005/0288246 A1 | 12/2005 | Iversen et al. |
| 2006/0024715 A1 | 2/2006 | Liu et al. |
| 2006/0074034 A1 | 4/2006 | Collins et al. ................. 514/44 |
| 2006/0099612 A1 | 5/2006 | Nakao et al. |
| 2006/0099616 A1* | 5/2006 | van Ommen ...... A61K 48/0016 |
| | | 435/6.11 |
| 2006/0147952 A1 | 7/2006 | Van Ommen et al. |
| 2006/0148740 A1 | 7/2006 | Platenburg ..................... 514/44 |
| 2006/0160121 A1 | 7/2006 | Mounts et al. |
| 2007/0021360 A1 | 1/2007 | Nyce et al. ..................... 514/44 |
| 2007/0082861 A1 | 4/2007 | Matsuo et al. ................. 514/44 |
| 2007/0134655 A1 | 6/2007 | Bentwich |
| 2007/0141628 A1 | 6/2007 | Cunningham et al. ........ 435/7.1 |
| 2007/0243546 A1* | 10/2007 | Cao ...................... C12Q 1/6837 |
| | | 435/6.12 |
| 2007/0275914 A1 | 11/2007 | Manoharan et al. ........... 514/44 |
| 2007/0292408 A1 | 12/2007 | Singh et al. ................. 424/130.1 |
| 2008/0015158 A1 | 1/2008 | Ichiro et al. |
| 2008/0015185 A1 | 1/2008 | Ahmed et al. ................ 514/218 |
| 2008/0039418 A1 | 2/2008 | Freier ........................... 514/44 |
| 2008/0113351 A1 | 5/2008 | Naito et al. ..................... 435/6 |
| 2008/0200409 A1 | 8/2008 | Wilson et al. .................. 514/44 |
| 2008/0207538 A1 | 8/2008 | Lawrence et al. ............. 514/41 |
| 2008/0209581 A1 | 8/2008 | Van Ommen et al. |
| 2008/0249294 A1 | 10/2008 | Haeberli et al. ............. 536/24.5 |
| 2009/0092981 A1 | 4/2009 | Swayze et al. ................... 435/6 |
| 2009/0099066 A1* | 4/2009 | Moulton ................ C12N 15/87 |
| | | 514/1.1 |
| 2009/0228998 A1 | 9/2009 | Van Ommen et al. |
| 2009/0269755 A1* | 10/2009 | Aartsma-Rus ..... A61K 48/0016 |
| | | 435/6.11 |
| 2009/0312532 A1 | 12/2009 | Van Deutekom et al. |
| 2010/0081627 A1 | 4/2010 | Sampath et al. ................. 514/47 |
| 2010/0099750 A1 | 4/2010 | McSwiggen et al. ...... 514/44 R |
| 2010/0130591 A1* | 5/2010 | Sazani ................. C12N 15/111 |
| | | 514/44 A |
| 2010/0168212 A1 | 7/2010 | Popplewell et al. ........ 514/44 R |
| 2010/0184833 A1 | 7/2010 | De Kimpe et al. |
| 2010/0248239 A1 | 9/2010 | Highsmith, Jr. et al. .......... 435/6 |
| 2011/0015253 A1 | 1/2011 | Wilton et al. ................. 514/44 A |
| 2011/0015258 A1 | 1/2011 | Wilton et al. ................. 514/44 R |
| 2011/0046203 A1 | 2/2011 | Wilton et al. ................. 514/44 A |
| 2011/0166081 A1 | 7/2011 | Campbell et al. ............. 514/20.9 |
| 2011/0263682 A1 | 10/2011 | De Kimpe et al. ............ 514/44 A |
| 2011/0263686 A1 | 10/2011 | Wilton et al. ................. 514/44 A |
| 2011/0294753 A1 | 12/2011 | De Kimpe et al. ............ 514/40 |
| 2012/0022134 A1 | 1/2012 | De Kimpe et al. |
| 2012/0022144 A1 | 1/2012 | Wilton et al. ................. 514/44 A |
| 2012/0022145 A1 | 1/2012 | Wilton et al. ................. 514/44 A |
| 2012/0029057 A1 | 2/2012 | Wilton et al. ................. 514/44 A |
| 2012/0029058 A1 | 2/2012 | Wilton et al. ................. 514/44 A |
| 2012/0029059 A1 | 2/2012 | Wilton et al. ................. 514/44 A |
| 2012/0029060 A1 | 2/2012 | Wilton et al. ................. 514/44 A |
| 2012/0041050 A1 | 2/2012 | Wilton et al. ................. 514/44 A |
| 2012/0046342 A1 | 2/2012 | Van Deutekom et al. |
| 2012/0046348 A1 | 2/2012 | Vaillant et al. ............... 514/44 R |
| 2012/0108652 A1 | 5/2012 | Popplewell et al. ........ 514/44 A |
| 2012/0122801 A1 | 5/2012 | Platenburg |
| 2012/0202752 A1 | 8/2012 | Lu |
| 2013/0072671 A1 | 3/2013 | Van Deutekom et al. |
| 2013/0116310 A1 | 5/2013 | Wilton et al. ................. 514/44 A |
| 2013/0217755 A1 | 8/2013 | Wilton et al. ................. 514/44 A |
| 2013/0253033 A1 | 9/2013 | Wilton et al. ................. 514/44 A |
| 2013/0253180 A1 | 9/2013 | Wilton et al. ................. 536/24.5 |
| 2013/0274313 A1 | 10/2013 | Wilton et al. ................. 514/44 A |
| 2013/0302806 A1 | 11/2013 | Van Deutekom |
| 2013/0331438 A1 | 12/2013 | Wilton et al. ................. 514/44 A |
| 2014/0045763 A1 | 2/2014 | Aguilera Diez et al. |
| 2014/0113955 A1 | 4/2014 | De Kimpe et al. |
| 2014/0128592 A1 | 5/2014 | De Kimpe et al. |
| 2014/0221458 A1 | 8/2014 | De Kimpe et al. |
| 2014/0275212 A1 | 9/2014 | Van Deutekom |

(56) References Cited

U.S. PATENT DOCUMENTS

| | | |
|---|---|---|
| 2014/0343266 A1 | 11/2014 | Watanabe et al. |
| 2014/0350076 A1 | 11/2014 | Van Deutekom |
| 2014/0357698 A1 | 12/2014 | Van Deutekom et al. |
| 2014/0357855 A1 | 12/2014 | Van Deutekom et al. |
| 2014/0378527 A1 | 12/2014 | Van Deutekom |
| 2015/0045413 A1 | 2/2015 | De Visser et al. |
| 2015/0080563 A2 | 3/2015 | Van Deutekom et al. |
| 2015/0148404 A1 | 5/2015 | De Visser et al. |
| 2015/0191725 A1 | 7/2015 | Van Deutekom |
| 2015/0203849 A1 | 7/2015 | Van Deutekom et al. |
| 2015/0218559 A1 | 8/2015 | Van Deutekom et al. |
| 2015/0322434 A1 | 11/2015 | Van Deutekom |
| 2015/0361424 A1 | 12/2015 | Van Deutekom |
| 2016/0053254 A1 | 2/2016 | De Kimpe et al. |
| 2016/0168570 A1 | 6/2016 | Van Deutekom et al. |
| 2016/0194636 A1 | 7/2016 | Van Deutekom et al. |
| 2016/0251658 A1 | 9/2016 | Van Deutekom et al. |
| 2016/0264967 A1 | 9/2016 | Van Deutekom et al. |
| 2016/0304864 A1 | 10/2016 | De Kimpe et al. |
| 2016/0355810 A1 | 12/2016 | Van Deutekom |
| 2017/0029818 A1 | 2/2017 | De Visser et al. |
| 2017/0029820 A1 | 2/2017 | Aguilera Diez et al. |
| 2017/0044534 A1 | 2/2017 | Van Deutekom |
| 2017/0107512 A1 | 4/2017 | De Kimpe et al. |

FOREIGN PATENT DOCUMENTS

| | | | |
|---|---|---|---|
| EP | 1 160 318 | 12/2001 | ............ C12N 15/11 |
| EP | 1 191 097 | 3/2002 | ............ C12N 15/11 |
| EP | 1 191 098 | 3/2002 | ............ C12N 15/11 |
| EP | 1 380 644 | 1/2004 | ............ C12N 15/11 |
| EP | 1 487 493 | 12/2004 | ............ A61K 47/48 |
| EP | 1 495 769 | 1/2005 | ............ A61K 47/48 |
| EP | 1 501 931 | 2/2005 | ............ C12N 15/11 |
| EP | 1 544 297 | 6/2005 | ............ C12N 15/11 |
| EP | 1 567 667 | 8/2005 | ............ C12Q 1/68 |
| EP | 1 568 769 | 8/2005 | ............ C12N 15/11 |
| EP | 1 619 249 | 1/2006 | ............ C12N 15/11 |
| EP | 1 857 548 | 11/2007 | ............ C12N 15/11 |
| EP | 2 119 783 | 11/2009 | ............ C12N 15/11 |
| EP | 2 135 948 | 12/2009 | ............ C12N 15/11 |
| JP | 2002-325582 A | 11/2002 | |
| KR | 2003/0035047 | 5/2003 | ............ A61K 48/00 |
| WO | WO 93/01286 | 1/1993 | ............ C12N 15/11 |
| WO | WO 95/16718 | 6/1995 | ............ C08F 255/02 |
| WO | WO 95/21184 | 8/1995 | ............ C07H 19/16 |
| WO | WO 95/030774 | 11/1995 | ............ C12Q 1/68 |
| WO | WO 97/012899 | 4/1997 | ............ C07H 21/04 |
| WO | WO 97/030067 | 8/1997 | ............ C07H 21/04 |
| WO | WO 98/18920 | 5/1998 | ............ C12N 15/12 |
| WO | WO 98/43993 | 10/1998 | ............ C07H 21/00 |
| WO | WO 98/49345 | 11/1998 | ............ C12Q 1/68 |
| WO | WO 98/53804 | 12/1998 | ............ A61K 31/00 |
| WO | WO 99/16871 | 4/1999 | ............ C12N 15/11 |
| WO | WO 99/55857 | 11/1999 | ............ C12N 15/11 |
| WO | WO-9963975 A2 | 12/1999 | |
| WO | WO 00/24885 | 5/2000 | ............ C12N 15/11 |
| WO | WO-0076554 A1 | 12/2000 | |
| WO | WO 01/16312 | 3/2001 | ............ C12N 15/11 |
| WO | WO 01/59102 | 8/2001 | ............ C12N 15/11 |
| WO | WO 01/79283 | 10/2001 | ............ C12N 15/87 |
| WO | WO 01/083503 | 11/2001 | ............ C07H 21/00 |
| WO | WO 01/083695 | 11/2001 | |
| WO | WO 02/02406 | 1/2002 | ............ B65B 9/02 |
| WO | WO 02/024906 | 3/2002 | ............ C12N 15/11 |
| WO | WO 02/26812 | 4/2002 | ............ C07K 14/47 |
| WO | WO 02/29006 | 4/2002 | |
| WO | WO 02/029056 | 4/2002 | ............ C12N 15/12 |
| WO | WO 03/002739 | 1/2003 | ............ C12N 15/11 |
| WO | WO-03004511 A2 | 1/2003 | |
| WO | WO 03/013437 | 2/2003 | |
| WO | WO 03/14145 | 2/2003 | ............ C07K 7/00 |
| WO | WO 03/037172 | 5/2003 | |
| WO | WO 03/062258 | 7/2003 | ............ C07H 21/02 |
| WO | WO 03/095647 | 11/2003 | ............ C12N 15/11 |
| WO | WO 2004/11060 | 2/2004 | |
| WO | WO 2004/015106 | 2/2004 | ............ C12N 15/11 |
| WO | WO 2004/016787 | 2/2004 | ............ C12N 15/11 |
| WO | WO 2004/037854 | 5/2004 | ............ C07K 1/04 |
| WO | WO 2004/047741 A2 | 6/2004 | |
| WO | WO 2004/048570 | 6/2004 | ............ C12N 15/11 |
| WO | WO 2004/083432 | 9/2004 | ............ C12N 15/11 |
| WO | WO 2004/083446 | 9/2004 | |
| WO | WO 2004/101787 | 11/2004 | ............ C12N 15/11 |
| WO | WO 2004/108157 | 12/2004 | ............ A61K 39/395 |
| WO | WO 2005/19453 | 3/2005 | ............ C12N 15/11 |
| WO | WO 2005/023836 | 3/2005 | |
| WO | WO 2005/035550 | 4/2005 | |
| WO | WO 2005/85476 | 9/2005 | ............ C12Q 1/68 |
| WO | WO 2005/086768 | 9/2005 | |
| WO | WO 2005/105995 | 11/2005 | ............ C12N 15/11 |
| WO | WO 2005/115439 | 12/2005 | ............ A61K 38/18 |
| WO | WO 2005/115479 | 12/2005 | ............ A61K 48/00 |
| WO | WO 2005/116204 | 12/2005 | ............ C12N 15/09 |
| WO | WO 2006/000057 | 1/2006 | ............ C12N 15/11 |
| WO | WO 2006/007910 | 1/2006 | ............ A61K 31/56 |
| WO | WO 2006/017522 | 2/2006 | ............ A61K 48/00 |
| WO | WO 2006/031267 | 3/2006 | ............ C12N 15/11 |
| WO | WO 2006/054262 | 5/2006 | |
| WO | WO 2006/083800 | 8/2006 | |
| WO | WO 2006/108052 | 10/2006 | ............ A61K 47/48 |
| WO | WO 2006/112705 | 10/2006 | ............ C12N 15/11 |
| WO | WO 2006/121960 | 11/2006 | ............ C12N 15/11 |
| WO | WO 2007/002904 | 1/2007 | ............ C12Q 1/68 |
| WO | WO 2007/004979 | 1/2007 | ............ A61K 38/00 |
| WO | WO 2007/044362 | 4/2007 | ............ A61K 48/00 |
| WO | WO 2007/089584 | 8/2007 | ............ A61K 48/00 |
| WO | WO 2007/089611 | 8/2007 | ............ C12N 15/11 |
| WO | WO 2007/123402 | 11/2007 | ............ A61K 38/18 |
| WO | WO 2007/135105 | 11/2007 | ............ C12N 15/11 |
| WO | WO 2008/11170 | 1/2008 | ............ C12Q 1/68 |
| WO | WO 2008/018795 | 2/2008 | ............ C12N 15/11 |
| WO | WO 2008/21136 | 2/2008 | ............ A01K 67/027 |
| WO | WO 2008/039418 | 4/2008 | ............ A61K 31/454 |
| WO | WO 2008/043561 | 4/2008 | ............ A61K 48/00 |
| WO | WO 2008/103060 | 8/2008 | ............ C12N 15/11 |
| WO | WO 2009/005793 | 1/2009 | ............ A61K 48/00 |
| WO | WO 2009/008727 | 1/2009 | ............ A61K 47/48 |
| WO | WO 2009/015384 | 1/2009 | ............ A61K 38/00 |
| WO | WO 2009/054725 | 4/2009 | ............ A61K 31/56 |
| WO | WO 2009/099326 | 8/2009 | ............ A61K 48/00 |
| WO | WO 2009/101399 | 8/2009 | ............ A61K 31/712 |
| WO | WO 2009/120887 | 10/2009 | ............ A61K 47/48 |
| WO | WO 2009/135322 | 11/2009 | ............ C12Q 1/68 |
| WO | WO 2009/139630 | 11/2009 | ............ C12N 15/11 |
| WO | WO 2009/144481 | 12/2009 | |
| WO | WO 2009/151600 | 12/2009 | ............ C12N 15/12 |
| WO | WO 2010/044894 | 4/2010 | ............ C07K 19/00 |
| WO | WO 2010/048586 | 4/2010 | ............ C12N 15/113 |
| WO | WO 2010/050802 | 5/2010 | ............ A61K 31/7105 |
| WO | WO 2010/110835 | 9/2010 | ............ C12Q 1/68 |
| WO | WO 2010/115993 | 10/2010 | ............ C12N 15/113 |
| WO | WO 2010/123369 | 10/2010 | ............ C12N 15/113 |
| WO | WO 2011/032045 | 3/2011 | ............ C07H 21/04 |
| WO | WO 2011/057350 | 5/2011 | ............ C12N 15/113 |
| WO | WO-2011078797 A2 | 6/2011 | |
| WO | WO 2011/097641 | 8/2011 | ............ C07H 21/04 |
| WO | WO-2012029986 A1 | 3/2012 | |
| WO | WO-2012150960 A1 | 11/2012 | |
| WO | WO-2013100190 A1 | 7/2013 | |
| WO | WO-2013170385 A1 | 11/2013 | |

OTHER PUBLICATIONS

Takeshima et al., Mutation spectrum of the dystrophin gene in 442 Duchenne/Becker muscular dystrophy cases from one Japanese referral center, 2010, Journal of Human Genetics, vol. 55, pp. 379-388.*

NCBI Reference SequenceL NM 004006.1, *Homo sapiens* dystrophin (DMD), transcript variant Dp427m, mRNA, accessed and retrieved from www.ncbi.nlm.nih.gov on Mar. 14, 2018.*

(56) References Cited

OTHER PUBLICATIONS

Aartsma-Rus et al., "Targeted exon skipping as a potential gene correction therapy for Duchenne muscular dystrophy," Neuromuscular Disorders 12, S71-S77, 2002.
Aartsma-Rus et al., "Therapeutic antisense-induced exon skipping in cultured muscle cells from six different DMD patients," Human Molecular Genetics, vol. 12, No. 8, 907-914, 2003.
Aartsma-Rus et al., "Antisense-Induced Multiexon Skipping for Duchenne Muscular Dystrophy Makes More Sense," Am. J. Hum. Genet, pp. 83-92, vol. 74, 2004.
Aartsma-Rus et al., "Comparative analysis of antisense oligonucleotide analogs for targeted DMD exon 46 skipping in muscle cells," Gene Ther., vol. 11, No. 18, pp. 1391-1398, Jul. 2004.
Aartsma-Rus et al., "Functional Analysis of 114 Exon-Internal AONs for Targeted DMD Exon Skipping: Induction for Steric Hindrance of SR Protein Binding Sites," Oligonucleotides 15: 284-297, 2005.
Aartsma-Rus et al., "Exploring the Frontiers of Therapeutic Exon Skipping for Duchenne Muscular Dystrophy by Double Targeting within One or Multiple Exons," Molecular Therapy, pp. 1-7, 2006.
Aartsma-Rus et al., "Therapeutic Modulation of DMD splicing by Blocking Exonic Splicing Enhancer Sites with Antisense Oligonucleotides," Ann NY Acad Sci, pp. 74-76, vol. 1082, 2006.
Aartsma-Rus et al., "Antisense Mediated exon skipping; A Versatile Tool with Therapeutic and Research Applications," RNA, pp. 1609-1624, vol. 13, No. 10, 2007.
Aartsma-Rus et al., "Antisense-Induced Exon Skipping for Duplications in Duchenne Muscular Dystrophy," BMC Med. Genet., 8:43, Jul. 5, 2007.
Aartsma-Rus et al., "Guidelines for Antisense Oligonucleotide Design and Insight into Splice-modulation Mechanisms," Molecular Therapy, vol. 17, No. 3, pp. 548-553, Mar. 2009.
Aartsma-Rus et al., "Theoretic Applicability of Antisense-Mediated Exon Skipping for Duchenne Muscular Dystrophy," Human Mutation, pp. 293-299, vol. 30, No. 3, 2009.
Abbs et al., "A convenient multiplex PCR system for the detection of dystrophin gene deletions: a comparative analysis with cDNA hybridisation shows mistypings by both methods," J. Med. Genet, pp. 304-311, vol. 28, 1991.
Agrawal et al., "Antisense therapeutics: is it as simple as complementary base recognition?" Mol. Med. Today, vol. 6., pp. 72-81, Feb. 2000.
Alter et al., "Systemic delivery of morpholino oligonucleotide restores dystrophin expression bodywide and improves dystrophic pathology." Nature Medicine. Feb. 2006;12(2):175-7, Epub, Jan. 29, 2006.
Anderson et al., "Correlated NOS-I[mu] and myf5 expression by satellite cells in mdx mouse muscle regeneration during NOS manipulation and deflazacort treatment," Neuromuscular Disorders, vol. 13(5): 388-396, Jun. 2003.
Arap et al., "Steps toward mapping the human vasculature by phage display," Nat. Med, vol. 8, No. 2, pp. 121-127, Feb. 2002.
Arechavala-Gomeza et al., "Comparative Analysis of Antisense Oligonucleotide Sequences for Targeted Skipping of Exon 51 During Dystrophin pre-mRNA Splicing in Human Muscle" Hum Gene Ther, pp. 798-810 vol. 18, No. 9, 2007.
Arruda V R, The role of immunosuppression in gene and cell based treatments for Duchenne Muscular Dystrophy. Molecular Therapy, Jun. 2007, vol. 15(6): 1040-1041.
Arzumanov et al., "Inhibition of HIV-1 Tat-dependent trans activation by steric block chimeric 2'-O-methyl/LNA oligoribonucleotides," Biochemistry, vol. 40, pp. 14645-14654, 2001.
Austin et al., "Cloning and characterization of alternatively spliced isoforms of Dp71," Hum Mol Genetics, vol. 4 No. 9 1475-1483, 1995.
Austin et al., "Expression and synthesis of alternatively spliced variants of Dp71 in adult human brain." Neuromuscular Disorders. 10(2000) 187-193.

Barabino et al., "Antisense probes targeted to an internal domain in US snRNP specifically inhibit the second step of pre-mRNA splicing," Nucleic Acids Res. 20(17):4457-4464, 1992.
Barany, "The ligase chain reaction in a PCR world," PCR Methods Appl., 1(1):5-16, Aug. 1991.
Beggs et al., "Detection of 98% of DMD/BMD gene deletions by polymerase chain reaction," Human Genetics, vol. 86, pp. 45-48, 1990.
Bijvoet et al., "Recombinant human acid α-glucosidase: high level production in mouse milk, biochemical characteristics, correction of enzyme deficiency in GSDII KO mice," Hum. Mol. Genet., vol. 7, No. 11, pp. 1815-1824, Oct. 1998.
Bionity.Com, NEWS—Center, Leiden University Medical Center and Prosensa B.V. Announce First Successful Clinical Study with RNA-based Therapeutic PRO051, dated Jan. 3, 2008, <http://www.bionity.com/news/e/76185>.
Biopharmaceutiques.com, Merging Pharma & Biotech, Edition 48, Jan. 10, 2008 <http://www.biopharmaceutiques.com/en/num>, visited Jan. 11, 2008.
Bremmer-Bout et al., "Targeted exon skipping in transgenic hDMD mice: A model for direct preclinical screening of human-specific antisense oligonucleotides," Mol Ther; 10(2):232-40, Aug. 2004.
Brett et al., "EST comparison indicates 38% of human m RNAs contain possible alternative splice forms," FEBS Lett 474(1): 83-86.
Brown et al., "Structure and mutation of the dystrophin gene," in Dystrophin: Gene, protein and cell biology, (Brown and Lucy, eds). Cambridge University Press, Cambridge, 1997, pp. 1-16.
Brown et al., "Gene delivery with synthetic (non viral) carriers," Int. J. Pharm., vol. 229, Nos. 1-2, pp. 1-21, Oct. 2001 [Abstract].
Buck et al., "Design Strategies and Performance of Custom DNA Sequencing Primers," Biotechniques. 27:528-536, 1999.
Burnett et al., "DNA sequence-specific polyamides alleviate transcription inhibition associated with long GAA. TTC repeats in Friedreich's ataxia," PNAS, pp. 11497-11502, vol. 103, No. 31, 2006.
Caplen et al., "Rescue of polyglutamine-mediated cytotoxicity by double-stranded RNA-mediated RNA interference," Human molecular genetics, pp. 175-184, vol. 11, No. 2, 2002.
Cartegni et al., Abstract, "Listening to silence and understanding nonsense: exonic mutations that affect splicing," Nature Reviews Genetics, pp. 285-298, vol. 3, Apr. 2002.
Cavanaugh, Third-Party Submission Under 35 U.S.C. §122(e) and 37 C.F.R. §1.290 for U.S. Appl. No. 11/233,495, 6 pages, Jun. 5, 2013.
Charley's Fund, Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.
Chaubourt et al., "Muscular nitric oxide synthase ([mu]NOS) and utrophin," J. of Physiology Paris, vol. 96(1-2): 43-52, Jan.-Mar. 2002.
Coulter et al., "Identification of a new class of exonic splicing enhancers by in vivo selection," Mol. Cell. Biol. 17(4) 2143-50, 1997.
Crooke, "Basic Principles of Antisense Therapeutics, Handbook of Experimental Pharmacology: Antisense Research and Application," Springer-Verlag, pp. 1-50, New York, 1998.
Dahlqvist et al., "Functional notch signaling is required for BMP4-induced inhibition of myogenic differentiation," Development 130:6089-6099, 2003.
De Angelis et al., "Chimeric snRNA molecules carrying antisense sequences against the splice junctions of exon 51 of the dystrophin pre-mRNA exon skipping and restoration of a dystrophin synthesis in delta 48-50 DMD cells," PNAS, pp. 9456-9461, vol. 99, No. 14, Jul. 9, 2002.
Denny et al., "Oligo-riboprobes. Tools for in situ hybridization," Histochemistry, 89:481-493, 1988.
Dickson et al., "Screening for antisense modulation of dystrophin pre-mRNA splicing," Neuromuscul. Disord., S67-70, Suppl. 1., 2002.

(56) References Cited

OTHER PUBLICATIONS

Dirkson et al. "Mapping the SF2/ASF Binding Sites in the Bovine Growth Hormone Exonic Splicing Enhancer," The Journal of Biological Chemistry, Sep. 15, 2000, pp. 29170-29177, vol. 275, No. 37.

Duboc et al., "Effect of Perindopril on the Onset and Progression of Left Ventricular Dysfunction in Duchenne Muscular Dystrophy," Journal of Amer. Coll. Cardiology, 45(6):855-7, Mar. 15, 2005.

Dubowitz, "Special Centennial Workshop—101st ENMC International Workshop: Therapeutic possibilities in Duchenne Muscular Dystrophy, Nov. 30-Dec. 2, 2001, Naarden, The Netherlands" Neuromuscul Disord., 12(4):421-31, May 2002.

Dubowitz, Foreword, Neuromuscular Disorders 12 www.elsevier. com/locate/nmd, pp. S1-S2, 2002.

Dunckley et al., "Modification of splicing in the Dsytrophin gene in cultured Mdx muscle cells by antisense oligoribonucleotides," Hum Mol Genet.,7(7):1083-90. 1995.

Dunckley et al., "Modulation of Splicing in the DMD Gene by Antisense Oligoribonucleotides," Nucleosides & Nucleotides, 1997, pp. 1665-1668, vol. 16, No. 7-9.

El-Andaloussi et al., "Induction of splice correction by cell-penetrating peptide nucleic acids," J. Gene Med., vol. 8, No. 10, pp. 1262-1273, Oct. 2006, [Abstract].

Erba et al., "Structure, chromosome location, and expression of the human gamma-actin gene: differential evolution, location, and expression of the cytoskeletal beta- and gamma-actin genes," Mol. Cell. Biology, 1988, 8(4):1775-89.

Errington et al., "Target selection for antisense oligonucleotide induced exon skipping in the dystrophin gene," J Gene Med. Jun. 2003; 5(6):518-27.

Espinos et al., "Efficient Non-Viral DNA-Mediated Gene Transfer to Human Primary Myoblasts Using Electroporation," Neuromuscular Disorders, 10, pp. 341-349, 2001.

Fainsod et al., "The dorsalizing and neural inducing gene follistatin is an antagonist of BMP-4," Mech Dev., 63(1): 39-50, 1997.

Feener et al., "Alternative splicing of human dystrophin mRNA generates isoforms at the carboxy terminus," Nature, 338 (6215): 509-511, 1989.

Fluiter, "In Vivo tumor growth inhibition and biodistribution studies of locked nucleic acid (LNA) antisense oligonucleotides," Nucl. Acids Research 2003, vol. 31., No. 3., pp. 953-962.

Fu et al., "An Unstable Triplet Repeat in a Gene Related to Myotonic Muscular Dystrophy", Science, vol. 255, 1256-1258, 1992.

Furling et al., "Viral vector producing antisense RNA restores myotonic dystrophy myoblast functions", Gene Therapy, 10, 795-802, 2003.

Galderisi et al., "Myotonic dystrophy: antisense oligonucleotide inhibition of DMPK gene expression in vitro," Biochem Biophys Res Commun 221:750-754, 1996.

Galderisi et al., "Antisense Oligonucleotides as Therapeutic Agents," Journal of Cellular Physiology, vol. 181, pp. 251-257, 1999.

Garcia-Blanco et al., "Alternative splicing in disease and therapy," Nat. Biotechnol., vol. 22, No. 5, pp. 535-546, May 2004.

Ghosh et al., "Mannose 6-phosphate receptors: new twists in the tale," Nat. Rev. Mol. Cell Biol., vol. 4, No. 3, pp. 202-212, Mar. 2003.

Ginjaar et al., "Dystrophin nonsense mutation induces different levels of exon 29 skipping and leads to variable phenotypes within one BMD family," European Journal of Human Genetics, 8, 793-796, 2000.

Gollins et al., "High-efficiency plasmid gene transfer into dystrophic muscle," Gene Ther., vol. 10, No. 6, pp. 504-512, Mar. 2003.

Grady, "Early drug test shows promise in treating muscular dystrophy," International Herald Tribune, Jan. 3, 2008, Health & Science, p. 9.

Grady, "Promising Dystrophy Drug Clears Early Test," The New York Times, Dec. 27, 2007.

Granchelli et al., "Pre-clinical screening of drugs using the mdx mouse," Neuromuscular Disorders, Pergamon Pres. vol. 10 (4-5): 235-239, Jun. 2000.

Gryaznov, "Oligonucleotide N3'--> P5' phosphoramidates as potential therapeutic agents," Biochemistry et Biophys. Acta, 1999, vol. 1489, pp. 131-140.

GSK Press Release, "GSK and Prosensa Announce Primary Endpoint Not Met in Phase III Study of Drisapersen in Patients With Duchenne Muscular Dystrophy," *Prosensa Press Release*, 3 pages, Sep. 20, 2013.

Hagiwara et al., "A novel point mutation (G-1 to T) in a 5' splice donor site of intron 13 of the dystrophin gene results in exon skipping and is responsible for Becker muscular dystrophy," Am J. Hum Genet. Jan. 1994;54(1):53-61.

Handa et al., "The AUUCU repeats responsible for spinocerebellar ataxia type 10 form unusual RNA hairpins," Journal of Biological Chemistry 280(32):29340-29345 (2005).

Hansen, "Product Development—Addition by subtraction," BioCentury, The Bernstein Report on BioBusiness, Jan. 7, 2008, p. A28 of 38.

Harding et al., "The Influence of Antisense Oligonucleotide Length on Dystrophin Exon Skipping," Molecular Therapy, vol. 15, No. 1, pp. 157-166, Jan. 2007.

Hasholt et al., "Antisense downregulation of mutant huntingtin in a cell model," Journal of Gene Medicine, 2003, pp. 528-538, vol. 5, No. 6.

Hassan, "Keys to the Hidden Treasures of the Mannose 6-Phosphate/ Insulin-Like Growth Factor 2 Receptor," Am. J. Path., vol. 162, No. 1, pp. 3-6 (Jan. 2003).

Heemskerk et al., "Development of Antisense-Mediated Exon Skipping as a Treatment for Duchenne Muscular Dystrophy," Annals NY Acad Sci vol. 1175 pp. 71-79, 2009.

Heemskerk et al. "In vivo comparison of 2'-O-methyl phosphorothioate and morpholino antisense oligonucleotides for Duchenne muscular dystrophy exon skipping," J. Gene Medicine, 11:257-266, 2009.

Heemskerk et al., "Preclinical PK and PD Studies on 2' O-methyl-phosphorothioate RNA antisense Oligonucleotides in the MDX Mouse Model," Mol. Ther vol. 18(6) pp. 1210-1217, 2010.

Highfield, "Hope for muscular dystrophy drug," The Daily Telegraph, Dec. 28, 2007.

Hoffman et al., "Somatic reversion/suppression of the mouse mdx phenotype in vivo." J. of the Neurological Sciences, 1990, 99: 9-25.

Hoffman, "Skipping toward Personalized Molecular Medicine," N. England J. Med., Dec. 27, 2007, pp. 2719-2722, vol. 357, No. 26.

Hussey et al., "Analysis of five Duchenne muscular dystrophy exons and gender determination using conventional duplex polymerase chain reaction on single cells," Molecular Human Reproduction, 1999, pp. 1089-1094, vol. 5, No. 11.

Hyndman, "High affinity binding of transferrin in cultures of embryonic neurons from the chick retina," Brain Res., 564(1):127-31, 1991.

Iezzi et al., "Deacetylase inhibitors increase muscle cell size by promoting myoblast recruitment and fusion through induction of follistation," Development Cell 6:673-684, 2004.

Ikezawa et al., "Dystrophin gene analysis on 130 patients with Duchenne Muscular dystrophy with a special reference to muscle mRNA analysis," Brain & Develop. 20:165-168, 1998.

Ito et al., "One of three examined purine-rich sequences selected from dystrophin exons exhibits splicing enhancer activity," Acta Myologica, vol. XX, pp. 151-153, 2001.

Ito et al., "Purine-Rich Exon Sequences Are Not Necessarily Splicing Enhancer Sequence in the Dystrophin Gene," Kobe J. Med. Sci. 47, 193/202, Oct. 2001.

Jou et al., "Deletion Detection in the Dystrophin Gene by Multiplex Gap Ligase Chain Reaction and Immunochromatographic Strip Technology," Human Mutation, 5:86-93, 1995.

Karras et al., "Deletion of Individual Exons and Induction of Soluble Murine Interleukin-5 Receptor-alpha Chain Expression through Antisense Oligonucleotide-Mediated Redirection of Pre-mRNA Splicing," Molecular Pharmacology, pp. 380-387, vol. 58, 2000.

Katholieke Universiteit Leuven, Letter from Katholieke Universiteit Leuven to Dr. N. Goemans, Child Neurology, UZ dated Jan. 22,

(56) References Cited

OTHER PUBLICATIONS 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).
J.A. Kemp, Request for an Opinion under Section 74(A) in relation to Patent No. EP (UK) 1619249B in the name of Academisch Ziekenhuis Leiden, 33 pages, dated Apr. 20, 2009.
J.A. Kemp, Request for an Opinion under Section 74(A) in relation to Patent No. EP (UK) 1 619 249B in the name of Academisch Ziekenhuis Leiden, opinion issued on Jun. 4, 2009.
J.A. Kemp, Request for UK IPO Opinion (Section 74A & Rule 93)—EP(UK) 1619249 dated Mar. 9, 2009.
Kerr et al., "BMP Regulates Skeletal Myogenesis at Two Steps," Molecular Cellular Proteomics 2.9:976. 123.8, 2003, [Abstract].
Kinali et al., "Local Restoration of Dystrophin Expression With the Morpholino Oligomer AVI-4658 in Duchenne Muscular Dystrophy: A Single-blind, Placebo-Controlled Dose-Escalation, Proof-of Concept Study. Lancet Neurol," vol. 8(10) pp. 918-928, 2009.
Krainer, Declaration of Dr. Adrian Krainer (submitted in Third Party's Stmt for JP Appl. No. 2002-529499, dated Oct. 29, 2010).
Kurrek et al., "Design of antisense oligonucleotides stabilized by locked nucleic acids." Nucleic Acids Research, 2002, vol. 30, No. 9, pp. 1911-1918.
Langlois et al., "Hammerhead ribozyme-mediated destruction of nuclear foci in myotonic dystrophy myoblasts," Molecular therapy, 2003, pp. 670-680, vol. 7, No. 5.
Laptev et al., "Specific inhibition of expression of a human collagen gene (COL1A1) with modified antisense oligonucleotides. The most effective target sites are clustered in double-stranded regions of the predicted secondary structure for the mRNA," Biochemistry 33(36):11033-11039, 1994.
Lee et al., "Receptor mediated uptake of peptides that bind the human transferrin receptor", Eur. J. Biochem. 268, 2004-2012, 2001.
Lewin, Genes VII, Chapter 22, Nuclear Splicing, pp. 704-705, Jan. 2000.
Liu et al., "A mechanism for exon skipping caused by nonsense or missense mutations in BRCA1 and other genes," Nat Genet, 27(1):55-8, Jan. 2001.
Liu et al., "Specific inhibition of Huntington's disease gene expression by siRNAs in cultured cells", Proc. Japan Acad. 79, Ser. B, 293-298, 2003.
Liu et al., "Identification of functional exonic splicing enhancer motifs recognized by individual SR proteins," Genes & Development, 1998, pp. 1998-2012, vol. 12.
Liu et al., "Efficiency of DNA Transfection of Rat Heart Myoblast Cells H9c2(2-1) by Either Polyethyleneimine or Electroporation," Appl Biochem Biotechnol, 164: 1172-1182 (2011).
Lonza, "Amaxa Cell Line Nucleofector.RTM. Kit V" for C2C12, 4 pages [date unknown].
Lu et al., "Massive Idiosyncratic Exon Skipping Corrects the Nonsense Mutation in Dystrophic Mouse Muscle and Produces Functional Revertant Fibers by Clonal Expansion," The Journal Cell Biology, Mar. 6, 2000, pp. 985-995, vol. 148, No. 5.
Lu et al., "Functional Amounts of Dystrophin Produced by Skipping the Mutated Exon in the MDX Dystrophic Mouse," Nat Med, 8: 1009-1014, 2003.
Lu et al., "Systemic delivery of antisense oligoribonucleotide restores dystrophin expression in body-wide skeletal muscles," *Proc. Natl. Acad. Sci. U.S.A.*, vol. 102, No. 1, pp. 198-203, Jan. 2005.
Lu et al., "Non-viral gene delivery in skeletal muscle: a protein factory," *Gene Ther.*, vol. 10, No. 2, pp. 131-142, Jan. 2003.
Ludolph et al., "Transcription Factor Families: Muscling in on the Myogenic Program," Dept. of Biological Sciences, 9(15): 1595-604. 1995.
Mann et al., "Antisense-induced exon skipping and synthesis of dystrophin in the mdx mouse," Proc Natl Acad Sci USA, 98(1):42-7, Jan. 2, 2001.
Mann et al., "Improved antisense oligonucleotide induced exon skipping in the mdx mouse model of muscular dystrophy," J Gene Med. Nov.-Dec. 2002:4(6):644-54.
Martiniuk et al., "Correction of glycogen storage disease type II by enzyme replacement with a recombinant human acid maltase produced by over-expression in a CHO-DHFR(neg) cell line," *Biochem. Biophys. Res. Commun.*, vol. 276, No. 3, pp. 917-923 (Oct. 2000) [Abstract].
Matsuo et al., "Exon Skipping during Splicing of Dystrophin mRNA Precursor due to an Intraexon Deletion in the Dystrophin Gene of Duchenne Muscular Dystrophy Kobe," J. Clin. Invest. 87, 2127-2131, 1991.
Matsuo et al., "Partial deletion of a dystrophin gene leads to exon skipping and to loss of an intra-exon hairpin structure from the predicted mRNA precursor" Biochem. Biophys. Res. Commun. 182(2):495-500, 1992.
Matsuo et al., "Duchenne/Becker muscular dystrophy: from molecular diagnosis to gene therapy," Brain Dev., 18(3):167-172, 1996.
Matsuo et al., "Duchenne and Becker Muscular Dystrophy: From Gene Diagnosis to Molecular Therapy", IUBMB Life, vol. 53, pp. 147-152, 2002.
Matteucci, "Structural modifications toward improved antisense oligonucleotides," Perspectives in Drug Disc and Design, vol. 4, pp. 1-16, 1996.
McClorey et al., "Induced Dystrophin Exon Skipping in Human Muscle Explants," Neuromuscul Disord, pp. 583-590, vol. 16, No. 9-10, 2006.
Medical News Today, LUMC and Prosensa report positive results of DMD study, Pharmaceutical Business Review Online, dated Dec. 28, 2007, <http://www.pharmaceutical-business-review.com/article.sub.--news.sub.- --print.asp?guid=8462FD44-F35D-4EOB-BC>.
Medical News Today, New Clinical Trial Results Show How Personalized Medicine Will Alter Treatment of Genetic Disorders, Medical News Today, Dec. 29, 2007 <http://www.medicalnewstoday.com/article/92777.php>.
Miller et al., "Antisense oligonucleotides: strategies for delivery" PSST vol. 1, No. 9; pp. 377-386, 1988.
Monaco et al., "An Explanation for the Phenotypic Differences between Patients Bearing Partial Deletions of the DMD Locus," Genomics, 1988, pp. 90-95, vol. 2.
Moon et al., "Target site Search and effective inhibition of leukaemic cell growth by a covalently closed multiple anti-sense oligonucleotide to c-myb," The Biochemical Journal, Mar. 1, 2000, vol. 346 Pt 2, pp. 295-303.
Munroe, "Antisense RNA inhibits splicing of pre-mRNA in vitro" EMBO J. 7(8):2523-2532, 1988.
Muntoni et al., "A Mutation in the Dystrophin Gene Selectively Affecting Dystrophin Expression in the Heart." J. Clin Invest, vol. 96 Aug. 1995, 693-699.
Muntoni et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.
Nakamura et al., "Exon Skipping Therapy for Duchenne Muscular Dystrophy Neuropathology," vol. 29(4) pp. 494-501, 2009.
Nishio et al., "Identification of a novel first exon in the human dystrophin gene and of a new promoter located more than 500 kb upstream of the nearest known promoter," J. Clin. Invest. 94:1037-1042, 1994.
O'Shaughnessy et al., "Superior Survival With Capecitabine Plus Docetaxel Combination Therapy in Anthracycline-Pretreated Patients With Advanced Breast Cancer: Phase III Trial Results," Journal of Clinical Oncology, vol. 20, No. 12 Jun. 15, 2002: pp. 2812-2823.
Onlo, Comparative analysis of AONs for inducing the skipping of exon 45 and 53 from the dystrophin gene in human control muscle cells, EP1619249, 3 pages, Aug. 23, 2013.
Onlo, Grounds of Appeal,—EP1619249, 16 pages, Aug. 23, 2013.
Onlo, List of all submitted documents—EP1619249, 4 pages, Aug. 23, 2013.
Onlo, Comparative Analysis of AONs for inducing the skipping of exon 53 from the dystrophin gene in human control muscle cells, EP1619249, 3 pages, Jan. 8, 2014.

(56) References Cited

OTHER PUBLICATIONS

Onlo, Exon 53 Alignment—EP1619249, 1 page, Jan. 8, 2014.
Onlo, Reply to the Grounds of Appeal filed in Opposition Proceedings of EP1619249, 35 pages, dated Jan. 8, 2014.
Opalinska and Gewirtz, "Nucleic-acid therapeutics: basic principles and recent applications," Nature Reviews Drug Discovery, 2002, vol. 1, pp. 503-514.
Oxford Dictionary of English, Oxford Dictionary of English, 2nd Edition, Revised, Oxford University Press, p. 158.
Pallard, Letter from C. Pallard re: Patentee in the Above-Identified Opposition Appeal Proceedings, 25 pages, Jun. 10, 2014.
Patel et al., "The Function of Myostatin and strategies of Myostatin blockade—new hope for therapies aimed at promoting growth of skeletal muscle," Neuromuscular Disorders 15(2):117-126, 2005.
Peterson et al., "Selective Down-Regulation of c-jun Gene Expression by Pentoxifylline and c-jun Antisense Interrupts Platelet-Derived Growth Factor Signaling: Pentoxifylline Inhibits Phosphorylation of c-Jun on Serine 73," Mol Pharmacol., 61(6): 1476-88, 2002.
Phillips, "Antisense Inhibition and Adeno-Associated Viral Vector Delivery for Reducing Hypertension," Hypertension, vol. 29, 177-187, 1997.
Politano et al., "Gentamicin administration in Duchenne patients with Premature stop codon, Preliminary results." Acta Myologica 22:15-21, 2003.
Popplewell et al., "Design of Phosphorodiamidate Morpholino Oligomers (PMOs) for the Induction of Exon Skipping of the Human DMD Gene," Mol. Ther vol. 17(3) pp. 554-561, 2009.
Pramono et al., Abstract, "Induction of Exon Skipping of the Dystrophin Transcript in Lymphoblastoid Cells by Transfecting an Antisense Oligodeoxynucleotide Complementary to an Exon Recognition Sequence," Biochemical and Biophysical Research Communications, Sep. 13, 1996, pp. 445-449, vol. 226, No. 2.
Prosensa Therapeutics B.V., Letter from Prosensa Therapeutics B.V. To Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.
Radley et al., "Duchenne muscular dystrophy: Focus on pharmaceutical and nutritional interventions," International J. of Biochem. and Cell Biol., vol. 39(3):469-477, Oct. 2006.
Rando, "Oligonucleotide-mediated gene therapy for muscular dystrophies," Neuromuscular Disorders, 2002, vol. 12, pp. S55-S60.
Reitter, "Deflazacort vs. prednisone in Duchenne muscular dystrophy: trends of an ongoing study," Brain Dev. 1995;17 Suppl:39-43.
Reuser et al., "Uptake and Stability of Human and Bovine Acid α-Glucosidase in Cultured Fibroblasts and Skeletal Muscle Cells from Glycogenosis Type II Patients," Exp. Cell Res., vol. 155, No. 1, pp. 178-189 (Nov. 1984).
Roberts et al., "Direct diagnosis of carriers of Duchenne and Becker muscular dystrophy by amplification of lymphocyte RNA," Lancet, 336 (8730-8731): 1523-6, 1990.
Roberts et al., "Direct detection of dystrophin gene rearrangements by analysis of dystrophin mRNA in peripheral blood lymphocytes," Am. J. Hum. Genet. 49(2): 298-310, 1991.
Roberts et al., "Exon structure of the human dystrophin gene," Genomics, 1993, vol. 16, No. 2, pp. 536-538, 1993.
Roberts et al., "Searching for the 1 in 2,400,000: a review of dystrophin gene point mutations," Hum. Mut. 4:1-11, 1994.
Rolland et al., "Overactivity of exercise-sensitive cation channels and their impaired modulation by IGF-1 in mdx native muscle fibers: beneficial effect of pentoxifylline," Dec. 2006; Epub Sep. 28, Neurobiology Disease, vol. 24(3): 466-474.
Rosen et al., "Combination Chemotherapy and Radiation Therapy in the Treatment of Metastatic Osteogenic Sarcoma." Cancer 35: 622-630, 1975.
Samoylova et al., "Elucidation of muscle-binding peptides by phage display screening," *Muscle Nerve*, vol. 22, No. 4, pp. 460-466, Apr. 1999.

Sarepta Therapeutics Inc., "Sarepta Therapeutics and University of Western Australia Announce Exclusive Worldwide Licensing Agreement for Exon-Skipping Program in Duchenne Muscular Dystrophy," News Release, EP1619249, 3 pages (2013).
Scanlon, "Anti-genes: siRNA, ribozymes, and antisense," Curr. Pharmaceutical Biotechnology, 2004, vol. 5, pp. 415-420.
Schnell, "Declaration of Dr. Fred Schnell in Support of Appeal of the Opposition Division's Decision to Maintain EP-B1 1 619 249 in amended form," 6 pages, Jan. 8, 2014.
Segalat et al., "Capon expression in skeletal muscle is regulated by position, repair, NOS activity, and dystrophy," Experimental Cell Research, Jan. 2005, vol. 302(2): 170-179.
Sertic et al., "Deletion screening of the Duchenne/Becker muscular dystrophy gene in Croatian population" Coll. Antropol. 1997, 1:151-156.
Shapiro and Senapathy, "RNA splice junctions of different classes of eukaryotes: sequence statistics and functional implications in gene expression." Nucleic Acids Research, 1987, vol. 15. No. 17, pp. 7155-7174.
Sherratt et al. "Exon Skipping and Translation in Patients with Frameshift Deletions in the Dystrophin Gene," Am. J. Hum. Genet, 1993, pp. 1007-1015, vol. 53.
Shiga et al., "Disruption of the Splicing Enhancer Sequence within Exon 27 of the Dystrophin Gene by a Nonsense Mutation Induces Partial Skipping of the Exon and Is Responsible for Becker Muscular Dystrophy," J. Clin. Invest., Nov. 1997, pp. 2204-2210, vol. 100, No. 9.
Simoes-Wust et al., "bcl-xL Antisense Treatment Induces Apoptosis in Breast Carcinoma Cells," Int. J. Cancer, 2000, pp. 582-590, vol. 87.
Sironi et al., "The dystrophin gene is alternatively spliced throughout its coding sequence," FEBS Letters 517, pp. 163-166, 2002.
Smith et al., "Muscle-specific peptide #5", Mar. 23, 1999. From http://www.ebi.ac.uk/cgi-bin/epo/epofetch?AAW89659, downloaded Jul. 16, 2007. XP 002442550.
Spitali et al., "Exon skipping mediated dystrophin reading frame restoration for small mutations," Hum Mut vol. 30(11) pp. 1527-1534, 2009.
Squires, "An Introduction to Nucleside and Nucelotide Analogues," Antiviral Therapy6 (Suppl. 3): 1-14, 2001.
Sterrenburg et al., "Gene expression of profiling highlights defective myogenesis in DMD patients and a possible role for bone morphogenetic protein 4," Neurobiology of Disease 23(1):228-236 (2006).
Summerton et al., "Morpholino Antisense Oligomers: Design, Preparation, and Properties," Antisense & Nucleic Acid Drug Development, vol. 7, pp. 187-195 (1997).
Surono et al., "Six Novel Transcripts that Remove a Huge Intron Ranging from 250 to 800 kb are Produced by Alternative Splicing of the 5' Region of the Dystrophin Gene in Human Skeletal Muscle," BBRC 239 895-899 (1997).
Surono et al., "Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther.," vol. 15(8) pp. 749-757 (2004).
Suter et al., "Double-target antisense U7 snRNAs promote efficient skipping of an aberrant exon in three human B-thalassemic mutations," Human Molecular Genetics, 1999, pp. 2415-2423, vol. 8, No. 13.
Suwanmanee et al., "Restoration of Human b-globin Gene Expression in Murine and Human IVS2-654 Thalassemic Erythroid Cells by Free Uptake of Antisense Oligonucleotides" Mol. Pharmacology 62(3):545-553.
Takeshima et al., "Modulation of In Vitro Splicing of the Upstream Intron by Modifying an Intra-Exon Sequence Which is Deleted from the Dystrophin Gene in Dystrophin Kobe," J. Clin. Invest., Feb. 1995, pp. 515-520, vol. 95.
Takeshima et al., "Expression of Dystrophin Protein in Cultured Duchenne Muscular Dystrophy Cells by Exon Skipping Induced by Antisense Oligonucleotide" (Abstract); Abstract of the Japan Society of Human Genetics General Meeting Program, 8 pages, Nov. 17-19, 1999.

(56) References Cited

OTHER PUBLICATIONS

Takeshima et al., "Oligonucleotides Against a Splicing Enhancer Sequence Led to Dystrophin Production in Muscle Cells From a Duchenne Muscular Dystrophy Patient Brain Dev," 23:788-90, Dec. 2001.
Takeshima et al., "Intravenous Infusion of an Antisense Oligonucleotide Results in Exon Skipping in Muscle Dystrophin mRNA of Duchenne Muscular Dystrophy," Pediatric Research. May 2006, 59, 5, p. 690-694.
Takeshima et al., "Basic research for treatment of Duchene muscular dystrophy using induction of exon skipping by means of antisense oligo DNA: effect of in vivo administration in mice," Park IP Translations, vol. 15, No. 2, 6 pages (2012).
Tanaka et al., "Polypurine Sequences within a Downstream Exon Function as a Splicing Enhanced, Molecular and Cellular Biology", Feb. 1994, pp. 1347-1354, vol. 14, No. 2.
Thanh et al., "Characterization of revertant muscle fibers in Duchenne muscular dystrophy, using exon-specific monoclonal antibodies against dystrophin." Am. J. Hum. Genet. 1995, vol. 56, pp. 725-731.
Tian et al., "Selection of novel exon recognition elements from a pool of random sequences." Mol Cell Biot 15(11):6291-8, 1995.
TREAT-NMD, TREAT-NMD, Neuromuscular Network, Jan. 11, 2008.
Tsuchida, "Peptides, Proteins & Antisense: the role of myostatin and bone morphogenetic proteins in muscular disorders," Expert Opinion of Biologica Therapy 6(2):147-153 (2006).
Van Deutekom et al., "Antisense-induced exon skipping restores dystrophin expression in DMD patient derived muscle cells," Hum Mol Genet. Jul. 15, 2001:10(15:1547-54).
Van Deutekom et al., "Advance in Duchenne Muscular Dystrophy gene therapy", Nature Reviews Genetics, vol. 4, Oct. 2003, 774-783.
Van Deutekom et al., "Local Dystrophin Restoration with Antisense Oligonucleotide PRO051," N. England J. Med., Dec. 27, 2007, pp. 2677-2686.
Van Deutekom, Declaration of Dr. JCT van Deutekom, EP1619249, 2 pages, Aug. 23, 2013.
Van Deutekom, Declaration of Dr. JCT Van Deutekom, EP1619249, 6 pages, Jan. 7, 2014.
Van Deutekom, Declaration of Dr. Judith van Deutekom, 8 pages, Jun. 10, 2014.
van Ommen et al., "The therapeutic potential of antisense-mediated exon skipping", Current Opinion in Molecular Therapeutics, 10(2); 140-149, 2008.
Van Vliet et al., "Assessment of the feasibility of exon 45-55 multiexon skipping for duchenne muscular dystrophy." BMC Medical Genetics, vol. 9:105 (7 pages), Dec. 2008.
Varani et al., "The G+U wobble base pair: A fundamental building block of RNA structure crucial to RNA function in diverse biological systems," EMBO Rep., vol. 1, No. 1, pp. 18-23, Jul. 2000.
Verhaart et al., "Prednisolone treatment does not interfere with 2'-O-methyl phosphorothioate antisense-mediated exon skipping in Duchenne muscular dystrophy." Hum Gene Ther. Mar. 2012;23(3):262-73. Epub Jan. 26, 2012.
Verreault et al., "Gene silencing in the development of personalized cancer treatment: the targets, the agents and the delivery systems." Curr. Gene Therapy, 2006, vol. 6, pp. 505-553.
Vickers et al., "Efficient reduction of target RNAs by small interfering RNA and RNase H-dependent antisense agents. A comparative analysis." J. Biol. Chem. 278(9):7108-7118 (2003).
Vossius & Partners, "Statement of Grounds of Appeal" filed in the opposition proceeding of EP1619249; dated Aug. 23, 2013, 41 pages.
Vossius & Partners, Reply of the Opponent to the Grounds of Appeal, 31 pages, Jan. 8, 2014.
Wang et al., "Adeno-associated virus vector carrying human minidystrophin genes effectively ameliorates muscular dystrophy in mdx mouse model", P.N.A.S. 97(25):13714-13719, Dec. 5, 2000.
Watakabe et al., "The role of exon sequences in splice site selection," Genes & Development, pp. 407-418, vol. 7, 1993.
Weiler et al., "Identical mutation in patients with limb girdle muscular dystrophy type 2B or Miyoshi myopathy suggests a role for modifier gene(s)," Human Molecular Genetics, vol. 8, No. 5, pp. 871-877, 1999.
Weisbart et al., "Cell type specific targeted intracellular delivery into muscle of a monoclonal antibody that binds myosin llb.," Mol. Immunol., vol. 39, No. 13, pp. 783-789 (Mar. 2003) [Abstract].
Wells et al., "Enhanced in Vivo Delivery of Antisense Oligonucleotide to Restore Dystrophin Expression in Adult MDX Mouse Muscle," FEBS Letters 2003 552: 145-149.
Wenk et al., "Quantitation of Mr 46000 and Mr 300000 mannose 6-phosphate receptors in human cells and tissues," Biochem. Int., vol. 23, No. 4, pp. 723-731 (Mar. 1991) [Abstract].
Wheway et al., "The Dystrophin Lymphocyte promoter revisited: 4.5-megabase intron, or artefact?" Neuromuscular Disorders 13(2003) 17-20.
Wilton et al., "Specific removal of the nonsense mutation from the mdx dystrophin protein mRNA using antisense oligonucleotides." Neuromuscular Disorders, 1999, vol. 9, pp. 330-338.
Wilton et al., "Antisense oligonucleotides, exon skipping and the dystrophin gene transcript," Acta Myologica XXIV:222-229 (2005).
Wilton et al., "Antisense Oligonucleotide-induced Exon Skipping Across the Human Dystrophin Gene Transcript", Molecular Therapy: The Journal of the American Society of Gene Therapy, vol. 15, No. 7, 1288-1296, Jul. 2007.
Yen et al., "Sequence-specific cleavage of Huntingtin MRNA by catalytic DNA," Animals of Neurology, pp. 366-373, vol. 46, No. 3, 1999.
Yin et al., "Effective Exon Skipping and Restoration of Dystrophin Expression by Peptide Nucleic Acid Antisense Oligonucleotides in mdx Mice," Mol. Ther., vol. 16, No. 1, pp. 38-45, Jan. 2008.
Yokota et al., "Efficacy of Systemic Morpholino Exon-Skipping in Duchenne Dystrophy Dogs," Ann Neurol., pp. 667-676, vol. 65, 2009.
Zhang et al., "Efficient expression of naked DNA delivered intraarterially to limb muscles of nonhuman primates," Hum. Gene. Ther., vol. 12, No. 4, pp. 427-438, Mar. 2001 [Abstract].
Zhou et al., "Current understanding of dystrophin-related muscular dystrophy and therapeutic challenges ahead," Chinese Medical J., Aug. 2006, vol. 119(16): 1381-1391.
GenBank, GenBank accession No. AZ993191.1, 2M0278E12F mouse 10kb plasmid UUGC2M library Mus muscu genomic clone UUGC2M0278E12F, genomic survey sequence, entry created and last updated on Apr. 27, 2001.
GenBank, GenBank accession No. EW162121.1, rfat0126.sub.--k17.y1 fat Sus scrofa cDNA5-, mRNA sequence, entry created on Aug. 13, 2007.
Australian Patent Office, Australian Office Action for AU 2009240879, dated Jun. 22, 2011.
Canadian Patent Office, Canadian Office Action for CA 2,524,255, dated Jul. 6, 2011.
Commissioner for Patents, Authorized Officer: Lee W. Young, International Search Report, International Application No. PCT/US10/48532, 4 pages, dated Jan. 26, 2011.
AVI Biopharma, Inc., Notice of Opposition filed against EP 1 619 249 B, dated Jun. 23, 2009.
Academisch Ziekenhuis Leiden, Patentee's response during prosecution of opposed patent, dated Jan. 27, 2010.
European Patent Office, International Preliminary Examination Report, International Application No. PCT/NL01/00697, dated Aug. 1, 2002.
European Patent Office, International Search Report, International Application No. PCT/NL01/00697, dated Dec. 21, 2002.
European Patent Office, Partial European Search Report—Application No. EP 03 07 7205, dated Dec. 10, 2003 (6 pages).
European Patent Office, Annex to the European Search Report on European Patent Application No. EP 03 07 7205, dated Dec. 10, 2003 (1 page).
European Patent Office, International Search Report, International Application No. PCT/NL2004/000196, dated Oct. 28, 2004.
European Patent Office, International Search Report, PCT/NL2006/000209, Oct. 5, 2006.

(56) References Cited

OTHER PUBLICATIONS

European Patent Office, Office Action—Application No. EP 05 076 770.6, dated Jan. 29, 2007 (5 pages).
European Patent Office, International Search Report for PCT/EP2007/054842, dated Aug. 21, 2007, 3 pages.
European Patent Office, International Preliminary Report on Patentability and Written Opinion for PCT/EP2007/054842, dated Nov. 21, 2008, 8 pages.
European Patent Office, International Search Report, International Application No. PCT/NL 2008/050673, dated Feb. 9, 2009.
European Patent Office, International Search Report, International Application No. PCT/NL 2008/050470, dated Jul. 2, 2009.
European Patent Office, International Search Report for PCT/NL2009/050006 dated Jul. 31, 2009.
European Patent Office, Authorized Officer: Romano, Alper, International Search Report for PCT/NL2010/050230, 5 pages, dated Jun. 24, 2010.
European Patent Office, International Search Report for PCT/NL2009/050113 dated Jun. 30, 2010.
United States Patent and Trademark Office, Office Action for U.S. Appl. No. 10/395,031, dated Apr. 2, 2009.
United States Patent and Trademark Office, Office Action for U.S. Appl. No. 10/395,031, dated Aug. 23, 2007.
United States Patent and Trademark Office, Office Action for U.S. Appl. No. 10/395,031, dated Feb. 6, 2006.
United States Patent and Trademark Office, Office Action for U.S. Appl. No. 10/395,031, dated Jul. 8, 2005.
United States Patent and Trademark Office, Office Action for U.S. Appl. No. 10/395,031, dated May 30, 2008.
United States Patent and Trademark Office, Office Action for U.S. Appl. No. 10/395,031, dated Nov. 30, 2006.
United States Patent and Trademark Office, Office Action for U.S. Appl. No. 10/395,031, dated Oct. 16, 2009.
United States Patent and Trademark Office, Office Action for U.S. Appl. No. 11/233,495, dated Dec. 1, 2008.
United States Patent and Trademark Office, Office Action for U.S. Appl. No. 11/233,495, dated Jun. 25, 2009.
United States Patent and Trademark Office, Office Action for U.S. Appl. No. 11/233,507, dated Jun. 15, 2007.
United States Patent and Trademark Office, Office Action for U.S. Appl. No. 11/233,507, dated Mar. 19, 2008.
United States Patent and Trademark Office, Office Action for U.S. Appl. No. 11/233,507, dated May 29, 2009.
United States Patent and Trademark Office, Office Action for U.S. Appl. No. 11/233,507, dated Nov. 12, 2008.
United States Patent and Trademark Office, Office Action for U.S. Appl. No. 11/982,285, dated May 4, 2009.
United States Patent and Trademark Office, Office Action for U.S. Appl. No. 11/982,285, dated Sep. 18, 2009.
Academisch Ziekenhuis Leiden, EPO—Munich, Translation of Japanese Patent Application No. 2000-125448 (D59), 31 pages, dated Sep. 27, 2000.
Academisch Ziekenhuis Leiden, EPO—Munich, Translation of Japanese Patent Application No. 2000-256547(D61), 42 pages, dated Aug. 23, 2001.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/55,210 are barred under 35 U.S.C. §135(b)); 25 pages, filed Nov. 18, 2014 [Patent Interference No. 106,008].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 2 (for Judgment Under 35 U.S.C. §112(b)), 32 pages, filed Nov. 18, 2014 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 1 (for Judgment Under 35 U.S.C. §112(a)), 38 pages, filed Nov. 18, 2014 [Patent Interference No. 106,008 (RES)].
University of Western Australia, *University of Western Australia* (U.S. Pat. Nos. 8,455,636, 7,960,541, 7,807,816, 8,486,907) v. *Academisch Ziekenhuis Leiden* (U.S. Appl. No. 11/233,495, 13/550,210, 14/198,992), Declaration of Matthew J.A. Wood, M.D.,D. Phil.—UVA Exhibit 2081, 184 pages, filed Sep. 19, 2014 [Patent Interference Nos. 106,007, 106,008, 106,113 (RES)].
University of Western Australia, *University of Western Australia* (U.S. Pat. Nos. 7,960,541, 7,807,816) v. *Academisch Ziekenhuis Leiden* (U.S. Appl. No. 13/550,210), University of Western Australia List of Proposed Motions, 6 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 1 (For Judgment that UWA's Claims are Unpatentable Under 35 U.S.C. §§ 102 and 103) 69 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 2 (To Deny UWA the Benefit of AU2004903474, 24 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 3 (For Judgment of Unpatentability Based on Myriad), 20 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Declaration of Erik Sontheimer, Ph.D., 112 pages, filed Nov. 17, 2014 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia List of Proposed Motions, 7 pages, filed Sep. 10, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 1 (For Judgment Under 35 U.S.C. §112(a)), 40 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 2 (For Judgment Under 35 U.S.C. §112(b)), 34 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA U.S. Pat. No. 8,455,636 and Academisch Ziekenhuis Leiden's U.S. Appl. No. 14/248,279), 36 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 1 (For Judgment that UWA Claims are Unpatentable Under 35 U.S.C. §§ 102 and 103) 69 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substan-

(56) References Cited

OTHER PUBLICATIONS tive Motion 3 (For Judgment of Unpatentability based on Myriad), 19 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Substantive Motion 2 (To Deny UWA the Benefit of AU 2004903474), 23 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Proposed Motions, 6 pages, filed Sep. 10, 2014 [Patent Interference No. 106,007 (RES)].
University of Western Australia, *University of Western Australia* (U.S. Pat. No. 8,486,907) v. *Academisch Ziekenhuis Leiden* (U.S. Appl. No. 14/198,992),University of Western Australia Motion 1 (To Maintain Interference Between UWA U.S. Pat. No. 8,486,907 and Academisch Ziekenhuis Leiden's U.S. Appl. No. 14/198,992), 45 pages, filed Nov. 18, 2014 [Patent Interference No. 106,013 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014 [Patent Interference No. 106,007 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Responsive Motion 4 (to Add Two New Claims), 57 pages, filed Dec. 23, 2014 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Second Declaration of Erik Sontheimer, Ph.D., 44 pages, filed Dec. 23, 2014 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015, [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S. C. § 102/103), 38 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S. C. § 101), 22 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Feb. 17, 2015), 18 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 1 (35 U.S. C. § 112(a)), 93 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 2 (Indefiniteness), 31 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 3 (Standing Order ¶ 203.1 and 37 C.F.R. § 41.202(a) and (e)), 20 pages, filed Feb. 17, 2015 [Patent Interference No. 106,007 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Exhibit List as of Feb. 17, 2015, 8 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 1 (Regarding Patentability Under 35 U.S.C. § 102/103), 39 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 2 (To Retain UWA's Benefit of AU 2004903474), 31 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 3 (Regarding Patentability Under 35 U.S.C. § 101), 22 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 4 (To deny entry of AZL's Proposed New Claims 30 and 31), 36 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden List of Exhibits (as of Feb. 17, 2015) 18 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 1 (35 U.S.C. § 112(a)), 83 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 2 (Indefiniteness), 32 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 3 (U.S.C. § 135(b)), 44 pages, filed Feb. 17, 2015 [Patent Interference No. 106,008 (RES)].
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden List of Exhibits (as of Feb. 17, 2015) 3 pages, filed Feb. 17, 2015 [Patent Interference No. 106,013 (RES)].
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden Opposition 1 (Standing Order ¶ 203.1 and 37 C.F.R. § 41.202 (a) and (e)) 20 pages, filed Feb. 17, 2015 [Patent Interference No. 106,013 (RES)].
University of Western Australia, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and

(56) References Cited

OTHER PUBLICATIONS 7,807,816) v. *Academisch Ziekenhuis Leiden* (U.S. Appl. No. 13/550,210) [Patent Interference No. 106,008 (RES)], Second Declaration of Matthew J.A. Wood, M.D., D. Phil., 78 pages, filed Feb. 17, 2015.

Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210) [Patent Interference No. 106,008 (RES)], $3^{rd}$ Declaration of Erik J. Sontheimer, Ph.D., 123 pages, filed Feb. 17, 2015 [Patent Interference Nos. 106,007 and 106,008 (RES)].

Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210) [Patent Interference No. 106,008 (RES)], Declaration of Judith Van Deutekom, 45 pages, filed Feb. 17, 2015 [Patent Interference Nos. 106,007 and 106,008 (RES)].

University of Western Australia, *University of Western Australia* (U.S. Pat. No. 8,455,636) v. *Academisch Ziekenhuis Leiden* (U.S. Appl. No. 11/233,495) University of Western Australia Objections (to Opposition Evidence) 15 pages, filed Feb. 24, 2015 [Patent Interference No. 106,007 (RES)].

University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Objections (to Opposition Evidence) 15 pages, filed Feb. 24, 2015 [Patent Interference No. 106,008 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 1 (For Judgment that UWA's Claims are Unpatentable Under 35 U.S.C. §§ 102 and 103) 17 pages, filed Apr. 3, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 2 (To Deny the Benefit of AU 2004903474) 11 pages, filed Apr. 3, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 3 (For Judgment of Unpatentability based on Myriad) 12 pages, filed Apr. 3, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 4 (In Support of Responsive Motion 4 to Add Two New Claims) 17 pages, filed Apr. 3, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015 [Patent Interference No. 106,007 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 1 (For Judgment that UWA's Claims are Unpatentable Under 35 U.S.C. §§ 102 and 103) 17 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 2 (To Deny the Benefit of AU 2004903474) 12 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 3 (For Judgment of Unpatentability based on Myriad) 13 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden List of Exhibits (as of Apr. 3, 2015) 18 pages, filed Apr. 3, 2015 [Patent Interference No. 106,008 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 1) 28 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 2) 22 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference) 17 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 3, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Request for Oral Argument, 3 pages, filed Apr. 10, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495 University of Western Australia Request for Oral Argument, 4 pages, filed Apr. 10, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495 University of Western Australia Miscellaneous Motion 4 (to exclude evidence), 21 pages, filed Apr. 10, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495 University of Western Australia Exhibit List, 10 pages, filed Apr. 10, 2015 [Patent Interference No. 106,007 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 1 (to AZL Opposition 1) 28 pages, filed Apr. 3, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 2 (to AZL Opposition 2) 22 pages, filed Apr. 3, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 3 (for judgment under 35 U.S.C. §135(b)) 19 pages, filed Apr. 3, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Request for Oral Argument, 3 pages, filed Apr. 10, 2015 [Patent Interference No. 106,008 (RES)].

(56) References Cited

OTHER PUBLICATIONS

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Request for Oral Argument, 4 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Miscellaneous Motion 4 (to exclude evidence), 21 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 10, 2015 [Patent Interference No. 106,008 (RES)].
Aartsma-Rus, A., et al., "Exonic Sequences Provide Better Targets for Antisense Oligonucleotides Than Splice Site Sequences in the Modulation of Duchenne Muscular Dystrophy Splicing," Oligonucleotides, vol. 20 (2), pp. 69-77, 2010.
Academisch Ziekenhuis Leiden, "Sequences of Exon 53, Putative SES Fragments and Oligonucleotides," p. 1, Dec. 5, 2001.
Beggs, et al., "*Homo sapiens* Dystrophin (DMD) Gene, Exon 55 and Partial CDS," National Center for Biotechnology Information, Database GenBank [Online], GenBank Accession No. AF213440.1, 2 pages, Jan. 27, 2002.
Cartegni, L., et al., "Correction of Disease-Associated Exon Skipping by Synthetic Exon-Specific Activators," Nature Structural Biology, vol. 10 (2), pp. 120-125, 2003.
Case-Green, S.C., et al., "Studies on the Base Pairing Properties of Deoxyinosine by Solid Phase Hybridisation to Oligonucleotides," Nucleic Acids Research, vol. 22 (2), pp. 131-136, 1994.
Chamberlain, "Dystrophin Levels Required for Genetic Correction of Duchenne Muscular Dystrophy," Basic and Applied Myology, vol. 7 (3-4), pp. 251-255, 1997.
Dorchies, O.M., et al., "Green Tea Extract and its Major Polyphenol (−)-Epigallocatechin Gallate Improve Muscle Function in a Mouse Model for Duchenne Muscular Dystrophy," American Journal of Physiology—Cell Physiology, vol. 290 (2), pp. C616-C625, 2006.
Goemans, N.M., et al., "Systemic Administration of PRO051 in Duchenne's Muscular Dystrophy," The New England Journal of Medicine, vol. 364 (16), pp. 1513-1522, 2011.
Habara, Y., et al., "In Vitro Splicing Analysis Showed that Availability of a Cryptic Splice Site is not a Determinant for Alternative Splicing Patterns Caused by +1G-A Mutations in Introns of the Dystrophin Gene," Journal of Medical Genetics, vol. 46 (8), pp. 542-547, 2009.
Henderson, A.M., et al., "The Basic Helix-Loop-Helix Transcription Factor HESR1 Regulates Endothelial Cell Tube Formation," The Journal of Biological Chemistry, vol. 276 (9), pp. 6169-6176, 2001.
Kendall, G.C., et al., "Dantrolene Enhances Antisense-Mediated Exon Skipping in Human and Mouse Models of Duchenne Muscular Dystrophy," Science Translational Medicine, vol. 4 (164), 26 pages, Dec. 12, 2012.
Martin, F.H., et al., "Base Pairing Involving Deoxyinosine: Implications for Probe Design," Nucleic Acids Research, vol. 13 (24), pp. 8927-8938, 1985.
McClorey, G., et al., "Antisense Oligonucleotide-Induced Exon Skipping Restores Dystrophin Expression in Vitro in a Canine Model of DMD," Gene Therapy, vol. 13, pp. 1373-1381, 2006.
Singh, V., et al., "Proportion and Pattern of Dystrophin Gene Deletions in North Indian Duchenne and Becker Muscular Dystrophy Patients," Human Genetics, vol. 99 (2), pp. 206-208, 1997.
Tennyson, C.N., et al., "The Human Dystrophin Gene Requires 16 Hours to be Transcribed and is Cotranscriptionally Spliced," Nature Genetics, vol. 9 (2), pp. 184-190, 1995.
Thomson Reuters Integrity, "Dystrophin gene (DMD) expression inhibitor PR0-051," Prous Integrity, XP002677703, Mar. 8, 2012.
Wang, Z., et al., "Sustained AAV-Mediated Dystrophin Expression in a Canine Model of Duchenne Muscular Dystrophy with a Brief Course of Immunosuppression," Molecular Therapy, vol. 15 (6), pp. 1160-1166, Jun. 2007.
Watkins, N.E., et al., "Nearest-Neighbor Thermodynamics of Deoxyinosine Pairs in DNA Duplexes," Nucleic Acids Research, vol. 33 (19), pp. 6258-6267, 2005.
Xu, L., et al., "Potential for Pharmacology of Ryanodine Receptor/Calcium Release Channels," Annals of the New York Academy of Sciences, vol. 853, pp. 130-148, Sep. 16, 1998.
Yokota, T., et al., "Antisense Oligo-Mediated Multiple Exon Skipping in a Dog Model of Duchenne Muscular Dystrophy," Methods in Molecular Biology, vol. 709, pp. 299-312, 2011.
Yu, R.Z., et al., "Development of an Ultrasensitive Noncompetitive Hybridization-Ligation Enzyme-Linked Immunosorbent Assay for the Determination of Phosphorothioate Oligodeoxynucleotide in Plasma," Analytical Biochemistry, vol. 304 (1), pp. 19-25, 2002.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Opposition 4 (To Not Exclude Evidence), 22 pages, filed May 5, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Exhibits (as of May 5, 2015) 18 pages, filed May 5, 2015 [Patent Interference No. 106,007 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's Opposition 4 (To Not Exclude Evidence), 21 pages, filed May 5, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's List of Exhibits (as of May 5, 2015) 18 pages, filed May 5, 2015 [Patent Interference No. 106,008 (RES)].
Patent Trial and Appeal Board, *University of Western Australia* (U.S. Pat. No. 8,486,907) v. *Academisch Ziekenhuis Leiden* (U.S. Appl. No. 14/198,992), Order to Show Cause—37 C.F.R. § 41.104(a), 3 pages, entered Jun. 22, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Decision-Motions—37 C.F.R. § 41.125(a), 12 pages, entered Jun. 22, 2015 [Patent Interference No. 106,013 (RES)].
University of Western Australia, *University of Western Australia* (U.S. Pat. No. 8,486,907) v. *Academisch Ziekenhuis Leiden* (U.S. Appl. No. 14/198,992), University of Western Australia Response to Order to Show Cause, 28 pages, filed Jul. 20, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Decision—Priority—37 C.F.R. § 41.125(a), 18 pages, entered Sep. 29, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Judgment—37 C.F.R. § 41.127, 2 pages, entered Sep. 29, 2015 [Patent Interference No. 106,013 (RES)].
Patent Trial and Appeal Board, *University of Western Australia* (U.S. Pat. No. 8,455,636) v. *Academisch Ziekenhuis Leiden* (U.S. Appl. No. 11/233,495); University of Western Australia (U.S. Pat. Nos. 7,960,541 and 7,807,816) v. Academisch Ziekenhuis Leiden (U.S. Appl. No. 13/550,210), Order—Oral Argument—37 C.F.R. § 41.124, 2 pages, entered Mar. 29, 2016 [Patent Interference Nos. 106,007 (RES) and 106,008 (RES)].
Patent Trial and Appeal Board, *University of Western Australia* (U.S. Pat. No. 8,455,636) v. *Academisch Ziekenhuis Leiden* (U.S. Appl. No. 11/233,495), Decision Motions—37 C.F.R. § 41.125(a), 53 pages, entered Apr. 29, 2016 [Patent Interference No. 106,007 (RES)].

(56) References Cited

OTHER PUBLICATIONS

Patent Trial and Appeal Board, *University of Western Australia* (U.S. Pat. No. 8,455,636) v. *Academisch Ziekenhuis Leiden* (U.S. Appl. No. 11/233,495), Redeclaration 37 C.F.R. § 41.203(c), 2 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Judgment—Motions—37 C.F.R. § 41.127, 3 pages, entered Apr. 29, 2016 [Patent Interference No. 106,007 (RES)].
University of Western Australia, *University of Western Australia* v. *Academisch Ziekenhuis Leiden*, Motion of Appellant University of Western Australia to Stay Appeal Pending Appeals in Two Related Interferences, Document 4-1, 7 pages, entered May 6, 2016 [Patent Interference No. 106,013] [Civil Action No. 2016-1937].
Patent Trial and Appeal Board, *University of Western Australia* (U.S. Pat. No. 8,455,636) v. *Academisch Ziekenhuis Leiden* (U.S. Appl. No. 11/233,495), Withdrawal and Reissue of Decision on Motions, 2 pages, entered May 12, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Decision Motions—37 C.F.R. § 41.125(a) (Substitute), 53 pages, entered May 12, 2016 [Patent Interference No. 106,007 (RES)].
Wu, et al., "Targeted Skipping of Human Dystrophin Exons in Transgenic Mouse Model Systemically for Antisense Drug Development," PLoS ONE, vol. 6, issue 5, May 17, 2011, 12 pages.
Academisch Ziekenhuis Leiden, *Academisch Ziekenhuis Leiden* v. *University of Western Australia, University of Western Australia* v. *Academisch Ziekenhuis Leiden*, "Academisch Ziekenhuis Leiden's Response to Motion of University of Western Australia to Designate as Companion Cases to Extend the Briefing Schedules," 6 pages, Nov. 18, 2016 [Interference Nos. 106,007, 106,008, 106,013].
Academisch Ziekenhuis Leiden, "Comparative analysis of AONs for inducing the skipping of exon 45 from the dystrophin gene in human control muscle cells," 2 pages, Oct. 23, 2014.
Academisch Ziekenhuis Leiden, Letter in Response to Article 94(3) EPC relating to EP2594641, 7 pages, Oct. 23, 2014.
Academisch Ziekenhuis Leiden, Patentee's letter to European Patent Office in the examination of EP 2602322, 4 pages, Dec. 9, 2013.
Academisch Ziekenhuis Leiden, Patentee's Response to Office Action to European Patent Office in the examination of EP 2602322, 6 pages, Oct. 21, 2014.
Academisch Ziekenhuis Leiden, Reply Brief of Appellant Academisch Ziekenhuis Leiden, US Court of Appeals for the Federal Circuit, Case: 16-2262, 40 pages, Apr. 25, 2017.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 4 (In Support of Responsive Motion 4 to Add Two New Claims), 17 pages, filed Apr. 3, 2015 [Patent Interference No. 106,008 (RES)].
Academisch Ziekenhuis Leiden, *University of Western Australia* v. *Academisch Ziekenhuis Leiden*, "Principal Brief of Appellee Academisch Ziekenhuis Leiden," 69 pages, filed Mar. 28, 2017 [Interference No. 106,013].
Anonymous, Third Party's Statement, Japanese Application No. 2002-529499, dated Oct. 29, 2010, 28 pages (English Translation attached).
Axelrod et al., "Intestinal Transport of Gentamicin with a Novel, Glycosteroid Drug Transport Agent," Pharmaceutical Research, vol. 15, No. 12, pp. 1876-1881, 1998.
Board of Patent Appeals and Interferences, Order—Motion Times—37 C.F.R., §41.104(c) 6 pages, entered Jul. 18, 2014.
Board of Patent Appeals and Interferences, Standing Order, 81 pages, entered Mar. 8, 2011.

International Searching Authority—European Patent Office, International Search Report, International Application No. PCT/NL2008/050475, 30 pages, Jun. 25, 2009.
Itoh et al., "Allergic Contact Dermatitis Due to Topical Drugs Contaiing Corticosteroids," Skin Research, 24(2), pp. 270-271, 1982.
Lewin, B., "Genes VII," Oxford University Press, 2000, Chapters: 1, 5, 22; pp. 29, 126, 129, 686, 704, 705.
Nakamura, et al., "The Latest Finding on Muscular Dystrophy," Medical Online, vol. 42, No. 4, pp. 382-386, 2008 (English translation attached 5 pgs.).
Nederlandsch Octrooibureau, Patentee's Letter in Response to EPO Communication regarding EP 13170245.8, 4 pages, Apr. 15, 2015.
Nederlandsch Octrooibureau, Patentee's Letter in Response to EPO Communication regarding EP 13170245.8, 5 pages, Oct. 20, 2014.
Nelson et al., "The Properties of Nucleotide Bases Affect the Three-Dimensional Structure of Nucleic Acids," Lehninger Principles of Biochemistry, Third Edition, p. 331, 2000.
Patent Trial and Appeal Board, Declaration—37 C.F.R., §41.203(b), 7 pages, entered Jul. 18, 2014.
Patent Trial and Appeal Board, *University of Western Australia* (U.S. Pat. No. 8,455,636) v. *Academisch Ziekenhuis Leiden* (U.S. Appl. No. 11/233,495), Errata, filed May 23, 2016, 2 pages [Patent Interference No. 106,007 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Declaration 37 C.F.R. § 41.203(b), entered Jul. 24, 2014, 7 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Order—Motion Times—37 CFR §41.104(C), entered Jul. 24, 2014, 6 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Decision—Motions—37 C.F.R. § 41.125(a), 20 pages, Sep. 20, 2016 [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Judgment—Motions—37 C.F.R. § 41.127, entered Sep. 20, 2016, 3 pages [Patent Interference No. 106,008 (RES)].
Sarepta Therapeutics Inc., Notice of Opposition to European patent EP 2636741 B1, 72 pages, Jan. 27, 2017.
United States Court of Appeals for the Federal Circuit, *Academisch Ziekenhuis Leiden* v. *University of Western Australia*, Notice Forwarding Certified List, Appeal No. 2016-2262, Aug. 5, 2016, 18 pages [Patent Interference No. 106,007 (RES)].
United States Court of Appeals for the Federal Circuit, Brief of Appellant University of Western Australia, 223 pages, dated Jan. 23, 2017 [Interference No. 106,013).
United States Court of Appeals for the Federal Circuit, Principal Brief of Appellant Academisch Ziekenhuis Leiden, 135 pages, filed Jan. 23, 2017 [Interference Patent No. 106,007].
United States Court of Appeals for the Federal Circuit, Principal Brief of Appellant Academisch Ziekenhuis Leiden, 80 pages, filed Jan. 23, 2017 [Patent Interference No. 106,008].
University of Western Australia, *Academisch Ziekenhuis Leiden* v. *University of Western Australia*, "Brief of Appellee University of Western Australia," 76 pages, Mar. 6, 2017 [Interference No. 106,007] .
University of Western Australia, *Academisch Ziekenhuis Leiden* v. *University of Western Australia*, "Response Brief of Appellee University of Western Australia," 51 pages, Mar. 6, 2017 [Interference No. 106,008] .
University of Western Australia, *Academisch Ziekenhuis Leiden* v. *University of Western Australia, University of Western Australia* v. *Academisch Ziekenhuis Leiden*, "Reply of University of Western Australia in Support of It's Motion to Designate as Companion Cases to Extend the Briefing Schedules," 8 pages, Nov. 21, 2016 [Interference Nos. 106,007, 106,008, 106,013] .

(56) References Cited

OTHER PUBLICATIONS

University of Western Australia, Reply Brief of Appellant University of Western Australia, US Court of Appeals for the Federal Circuit, Case: 16-1937, 16-2086, 40 pages, Apr. 25, 2017.
University of Western Australia, *University of Western Australia* v. *Academisch Ziekenhuis Leiden*, Corrected Brief of Appellant University of Western Australia, 223 pages, filed Feb. 16, 2017 [Interference No. 106,013].
Van Deutekom, J.C., Transcript of deposition testimony of Dr. Judith van Deutekom taken on Mar. 11, 2015, pertaining to Patent Interference No. 106,007 (RES); relating to U.S. Pat. No. 8,455,636, 169 pages.
U.S. Appl. No. 10/395,031, filed Mar. 21, 2003, issued Jul. 5, 2011 as U.S. Pat. No. 7,973,015.
U.S. Appl. No. 11/233,495, filed Sep. 21, 2005.
U.S. Appl. No. 11/233,507, filed Sep. 21, 2005.
U.S. Appl. No. 11/919,248, filed Feb. 28, 2008.
U.S. Appl. No. 11/982,285, filed Oct. 31, 2007.
U.S. Appl. No. 12/198,007, filed Aug. 25, 2008, issued May 19, 2009 as U.S. Pat. No. 7,534,879.
U.S. Appl. No. 12/297,251, filed Nov. 25, 2009, issued Nov. 6, 2012 as U.S. Pat. No. 8,304,398.
U.S. Appl. No. 12/300,629, filed Mar. 24, 2009, issued Jan. 29, 2013 as U.S. Pat. No. 8,361,979.
U.S. Appl. No. 12/377,160, filed Feb. 24, 2010.
U.S. Appl. No. 12/383,897, filed Mar. 30, 2009.
U.S. Appl. No. 12/684,534, filed Jan. 8, 2010, issued Dec. 17, 2013 as U.S. Pat. No. 8,609,065.
U.S. Appl. No. 12/685,369, filed Jan. 11, 2010, issued Sep. 18, 2012 as U.S. Pat. No. 8,268,962.
U.S. Appl. No. 12/767,702, filed Apr. 26, 2010, issued Jan. 26, 2016 as U.S. Pat. No. 9,243,245.
U.S. Appl. No. 12/852,057, filed Aug. 6, 2010, issued Sep. 11, 2012 as U.S. Pat. No. 8,263,760.
U.S. Appl. No. 12/976,381, filed Dec. 22, 2010, issued Jun. 24, 2014 as U.S. Pat. No. 8,759,507.
U.S. Appl. No. 12/992,218, filed Nov. 11, 2010, issued Sep. 22, 2015 as U.S. Pat. No. 9,139,828.
U.S. Appl. No. 13/094,548, filed Apr. 26, 2011.
U.S. Appl. No. 13/094,571, filed Apr. 26, 2011.
U.S. Appl. No. 13/266,110, filed Oct. 24, 2011.
U.S. Appl. No. 13/349,198, filed Jan. 12, 2012.
U.S. Appl. No. 13/529,640, filed Jun. 21, 2012, issued Aug. 12, 2014 as U.S. Pat. No. 8,802,645.
U.S. Appl. No. 13/550,210, filed Jul. 16, 2012.
U.S. Appl. No. 13/568,866, filed Aug. 7, 2012, issued Aug. 27, 2013 as U.S. Pat. No. 8,519,097.
U.S. Appl. No. 13/718,666, filed Dec. 18, 2012.
U.S. Appl. No. 14/056,464, filed Oct. 17, 2013.
U.S. Appl. No. 14/097,210, filed Dec. 4, 2013.
U.S. Appl. No. 14/134,971, filed Dec. 19, 2013.
U.S. Appl. No. 14/198,992, filed Mar. 6, 2014.
U.S. Appl. No. 14/200,251, filed Mar. 7, 2014.
U.S. Appl. No. 14/248,279, filed Apr. 8, 2014.
U.S. Appl. No. 14/295,298, filed Jun. 3, 2014.
U.S. Appl. No. 14/295,311, filed Jun. 3, 2014.
U.S. Appl. No. 14/313,152, filed Jun. 24, 2014.
U.S. Appl. No. 14/331,934, filed Jul. 15, 2014.
U.S. Appl. No. 14/444,244, filed Jul. 28, 2014.
U.S. Appl. No. 14/522,002, filed Oct. 23, 2014.
U.S. Appl. No. 14/542,183, filed Nov. 14, 2014.
U.S. Appl. No. 14/581,633, filed Dec. 23, 2014.
U.S. Appl. No. 14/631,686, filed Feb. 25, 2015.
U.S. Appl. No. 14/678,517, filed Apr. 3, 2015.
U.S. Appl. No. 14/688,871, filed Apr. 16, 2015.
U.S. Appl. No. 14/712,753, filed May 14, 2015.
U.S. Appl. No. 14/809,483, filed Jul. 27, 2015.
U.S. Appl. No. 14/839,200, filed Aug. 28, 2015.
U.S. Appl. No. 14/990,712, filed Jan. 7, 2016.
U.S. Appl. No. 15/047,233, filed Feb. 18, 2016.
U.S. Appl. No. 15/053,185, filed Feb. 25, 2016.
U.S. Appl. No. 15/057,861, filed Mar. 1, 2016.
U.S. Appl. No. 15/094,212, filed Apr. 8, 2016.
U.S. Appl. No. 15/098,589, filed Apr. 14, 2016.
U.S. Appl. No. 90/011,320, filed Nov. 9, 2010.
U.S. Appl. No. 15/468,239, filed Mar. 24, 2017.
U.S. Appl. No. 15/479,639, filed Apr. 5, 2017.
U.S. Appl. No. 15/479,646, filed Apr. 5, 2017.

* cited by examiner

Human control PB-MNCs

Monkey PB-MNCs
T: IV 6 mg/kg PS188

SEQUENCE LISTING

<160> NUMBER OF SEQ ID NOS: 47

<210> SEQ ID NO 1
<211> LENGTH: 16
<212> TYPE: DNA
<213> ORGANISM: Homo sapiens

<400> SEQUENCE: 1
guggcuaaca gaagcu                                                        16

<210> SEQ ID NO 2
<211> LENGTH: 17
<212> TYPE: DNA
<213> ORGANISM: Homo sapiens

<400> SEQUENCE: 2
gggaacaugc uaaauac                                                       17

<210> SEQ ID NO 3
<211> LENGTH: 18
<212> TYPE: DNA
<213> ORGANISM: Homo sapiens

<400> SEQUENCE: 3
agacacaaau uccugaga                                                      18

<210> SEQ ID NO 4
<211> LENGTH: 11
<212> TYPE: DNA
<213> ORGANISM: Homo sapiens

<400> SEQUENCE: 4
cuguugagaa a                                                             11

<210> SEQ ID NO 5
<211> LENGTH: 20
<212> TYPE: RNA
<213> ORGANISM: Artificial
<220> FEATURE:
<223> OTHER INFORMATION: synthetic oligonucleotide

<400> SEQUENCE: 5
ucagcuucug uuagccacug                                              20

<210> SEQ ID NO 6
<211> LENGTH: 20
<212> TYPE: RNA
<213> ORGANISM: Artificial
<220> FEATURE:
<223> OTHER INFORMATION: synthetic oligonucleotide

<400> SEQUENCE: 6
uucagcuucu guuagccacu                                              20

<210> SEQ ID NO 7
<211> LENGTH: 21
<212> TYPE: RNA
<213> ORGANISM: Artificial
<220> FEATURE:
<223> OTHER INFORMATION: synthetic oligonucleotide

<400> SEQUENCE: 7
uucagcuucu guuagccacu g                                            21

<210> SEQ ID NO 8
<211> LENGTH: 21
<212> TYPE: RNA
<213> ORGANISM: Artificial
<220> FEATURE:
<223> OTHER INFORMATION: synthetic oligonucleotide

<400> SEQUENCE: 8
ucagcuucug uuagccacug a                                            21

<210> SEQ ID NO 9
<211> LENGTH: 22
<212> TYPE: RNA
<213> ORGANISM: Artificial
<220> FEATURE:
<223> OTHER INFORMATION: synthetic oligonucleotide

<400> SEQUENCE: 9
uucagcuucu guuagccacu ga                                           22

<210> SEQ ID NO 10
<211> LENGTH: 22
<212> TYPE: RNA
<213> ORGANISM: Artificial
<220> FEATURE:
<223> OTHER INFORMATION: synthetic oligonucleotide

<400> SEQUENCE: 10
ucagcuucug uuagccacug au                                           22

<210> SEQ ID NO 11
<211> LENGTH: 23
<212> TYPE: RNA
<213> ORGANISM: Artificial
<220> FEATURE:

<223> OTHER INFORMATION: synthetic oligonucleotide

<400> SEQUENCE: 11
uucagcuucu guuagccacu gau                                              23

<210> SEQ ID NO 12
<211> LENGTH: 23
<212> TYPE: RNA
<213> ORGANISM: Artificial
<220> FEATURE:
<223> OTHER INFORMATION: synthetic oligonucleotide

<400> SEQUENCE: 12
ucagcuucug uuagccacug auu                                              23

<210> SEQ ID NO 13
<211> LENGTH: 24
<212> TYPE: RNA
<213> ORGANISM: Artificial
<220> FEATURE:
<223> OTHER INFORMATION: synthetic oligonucleotide

<400> SEQUENCE: 13
uucagcuucu guuagccacu gauu                                             24

<210> SEQ ID NO 14
<211> LENGTH: 24
<212> TYPE: RNA
<213> ORGANISM: Artificial
<220> FEATURE:
<223> OTHER INFORMATION: synthetic oligonucleotide

<400> SEQUENCE: 14
ucagcuucug uuagccacug auua                                             24

<210> SEQ ID NO 15
<211> LENGTH: 24
<212> TYPE: RNA
<213> ORGANISM: Artificial
<220> FEATURE:
<223> OTHER INFORMATION: synthetic oligonucleotide

<400> SEQUENCE: 15
uucagcuucu guuagccacu gaua                                             24

<210> SEQ ID NO 16
<211> LENGTH: 25
<212> TYPE: RNA
<213> ORGANISM: Artificial
<220> FEATURE:
<223> OTHER INFORMATION: synthetic oligonucleotide

<400> SEQUENCE: 16
ucagcuucug uuagccacug auuaa                                            25

<210> SEQ ID NO 17
<211> LENGTH: 26
<212> TYPE: RNA
<213> ORGANISM: Artificial
<220> FEATURE:
<223> OTHER INFORMATION: synthetic oligonucleotide

<400> SEQUENCE: 17
uucagcuucu guuagccacu gauuaa                                           26

```
<210> SEQ ID NO 18
<211> LENGTH: 26
<212> TYPE: RNA
<213> ORGANISM: Artificial
<220> FEATURE:
<223> OTHER INFORMATION: synthetic oligonucleotide

<400> SEQUENCE: 18
ucagcuucug uuagccacug auuaaa                                               26

<210> SEQ ID NO 19
<211> LENGTH: 27
<212> TYPE: RNA
<213> ORGANISM: Artificial
<220> FEATURE:
<223> OTHER INFORMATION: synthetic oligonucleotide

<400> SEQUENCE: 19
uucagcuucu guuagccacu gauuaaa                                              27

<210> SEQ ID NO 20
<211> LENGTH: 19
<212> TYPE: RNA
<213> ORGANISM: Artificial
<220> FEATURE:
<223> OTHER INFORMATION: synthetic oligonucleotide

<400> SEQUENCE: 20
cagcuucugu uagccacug                                                       19

<210> SEQ ID NO 21
<211> LENGTH: 21
<212> TYPE: RNA
<213> ORGANISM: Artificial
<220> FEATURE:
<223> OTHER INFORMATION: synthetic oligonucleotide

<400> SEQUENCE: 21
cagcuucugu uagccacuga u                                                    21

<210> SEQ ID NO 22
<211> LENGTH: 21
<212> TYPE: RNA
<213> ORGANISM: Artificial
<220> FEATURE:
<223> OTHER INFORMATION: synthetic oligonucleotide

<400> SEQUENCE: 22
agcuucuguu agccacugau u                                                    21

<210> SEQ ID NO 23
<211> LENGTH: 22
<212> TYPE: RNA
<213> ORGANISM: Artificial
<220> FEATURE:
<223> OTHER INFORMATION: synthetic oligonucleotide

<400> SEQUENCE: 23
cagcuucugu uagccacuga uu                                                   22

<210> SEQ ID NO 24
<211> LENGTH: 22
<212> TYPE: RNA
<213> ORGANISM: Artificial
<220> FEATURE:
<223> OTHER INFORMATION: synthetic oligonucleotide
```

```
<400> SEQUENCE: 24
agcuucuguu agccacugau ua                                    22

<210> SEQ ID NO 25
<211> LENGTH: 23
<212> TYPE: RNA
<213> ORGANISM: Artificial
<220> FEATURE:
<223> OTHER INFORMATION: synthetic oligonucleotide

<400> SEQUENCE: 25
cagcuucugu uagccacuga uua                                   23

<210> SEQ ID NO 26
<211> LENGTH: 23
<212> TYPE: RNA
<213> ORGANISM: Artificial
<220> FEATURE:
<223> OTHER INFORMATION: synthetic oligonucleotide

<400> SEQUENCE: 26
agcuucuguu agccacugau uaa                                   23

<210> SEQ ID NO 27
<211> LENGTH: 24
<212> TYPE: RNA
<213> ORGANISM: Artificial
<220> FEATURE:
<223> OTHER INFORMATION: synthetic oligonucleotide

<400> SEQUENCE: 27
cagcuucugu uagccacuga uuaa                                  24

<210> SEQ ID NO 28
<211> LENGTH: 24
<212> TYPE: RNA
<213> ORGANISM: Artificial
<220> FEATURE:
<223> OTHER INFORMATION: synthetic oligonucleotide

<400> SEQUENCE: 28
agcuucuguu agccacugau uaaa                                  24

<210> SEQ ID NO 29
<211> LENGTH: 25
<212> TYPE: RNA
<213> ORGANISM: Artificial
<220> FEATURE:
<223> OTHER INFORMATION: synthetic oligonucleotide

<400> SEQUENCE: 29
cagcuucugu uagccacuga uuaaa                                 25

<210> SEQ ID NO 30
<211> LENGTH: 20
<212> TYPE: RNA
<213> ORGANISM: Artificial
<220> FEATURE:
<223> OTHER INFORMATION: synthetic oligonucleotide

<400> SEQUENCE: 30
agcuucuguu agccacugau                                       20

<210> SEQ ID NO 31
<211> LENGTH: 20
```

```
<210> SEQ ID NO 31
<211> LENGTH: 20
<212> TYPE: RNA
<213> ORGANISM: Artificial
<220> FEATURE:
<223> OTHER INFORMATION: synthetic oligonucleotide

<400> SEQUENCE: 31
gcuucuguua gccacugauu                                                  20

<210> SEQ ID NO 32
<211> LENGTH: 21
<212> TYPE: RNA
<213> ORGANISM: Artificial
<220> FEATURE:
<223> OTHER INFORMATION: synthetic oligonucleotide

<400> SEQUENCE: 32
gcuucuguua gccacugauu a                                                21

<210> SEQ ID NO 33
<211> LENGTH: 22
<212> TYPE: RNA
<213> ORGANISM: Artificial
<220> FEATURE:
<223> OTHER INFORMATION: synthetic oligonucleotide

<400> SEQUENCE: 33
gcuucuguua gccacugauu aa                                               22

<210> SEQ ID NO 34
<211> LENGTH: 23
<212> TYPE: RNA
<213> ORGANISM: Artificial
<220> FEATURE:
<223> OTHER INFORMATION: synthetic oligonucleotide

<400> SEQUENCE: 34
gcuucuguua gccacugauu aaa                                              23

<210> SEQ ID NO 35
<211> LENGTH: 23
<212> TYPE: RNA
<213> ORGANISM: Artificial
<220> FEATURE:
<223> OTHER INFORMATION: synthetic oligonucleotide

<400> SEQUENCE: 35
ccauuuguau uuagcauguu ccc                                              23

<210> SEQ ID NO 36
<211> LENGTH: 20
<212> TYPE: RNA
<213> ORGANISM: Artificial
<220> FEATURE:
<223> OTHER INFORMATION: synthetic oligonucleotide

<400> SEQUENCE: 36
agauaccauu uguauuuagc                                                  20

<210> SEQ ID NO 37
<211> LENGTH: 19
<212> TYPE: RNA
<213> ORGANISM: Artificial
<220> FEATURE:
<223> OTHER INFORMATION: synthetic oligonucleotide

<400> SEQUENCE: 37
```

```
gccauuucuc aacagaucu                                          19

<210> SEQ ID NO 38
<211> LENGTH: 23
<212> TYPE: RNA
<213> ORGANISM: Artificial
<220> FEATURE:
<223> OTHER INFORMATION: synthetic oligonucleotide

<400> SEQUENCE: 38
gccauuucuc aacagaucug uca                                     23

<210> SEQ ID NO 39
<211> LENGTH: 23
<212> TYPE: RNA
<213> ORGANISM: Artificial
<220> FEATURE:
<223> OTHER INFORMATION: synthetic oligonucleotide

<400> SEQUENCE: 39
auucucagga auugugucu uuc                                      23

<210> SEQ ID NO 40
<211> LENGTH: 21
<212> TYPE: RNA
<213> ORGANISM: Artificial
<220> FEATURE:
<223> OTHER INFORMATION: synthetic oligonucleotide

<400> SEQUENCE: 40
ucucaggaau uugugucuuu c                                       21

<210> SEQ ID NO 41
<211> LENGTH: 18
<212> TYPE: RNA
<213> ORGANISM: Artificial
<220> FEATURE:
<223> OTHER INFORMATION: synthetic oligonucleotide

<400> SEQUENCE: 41
guucagcuuc uguuagcc                                           18

<210> SEQ ID NO 42
<211> LENGTH: 21
<212> TYPE: RNA
<213> ORGANISM: Artificial
<220> FEATURE:
<223> OTHER INFORMATION: synthetic oligonucleotide

<400> SEQUENCE: 42
cugauuaaau aucuuuauau c                                       21

<210> SEQ ID NO 43
<211> LENGTH: 18
<212> TYPE: RNA
<213> ORGANISM: Artificial
<220> FEATURE:
<223> OTHER INFORMATION: synthetic oligonucleotide

<400> SEQUENCE: 43
gccgccauuu cucaacag                                           18

<210> SEQ ID NO 44
<211> LENGTH: 18
<212> TYPE: RNA
<213> ORGANISM: Artificial
```

```
<220> FEATURE:
<223> OTHER INFORMATION: synthetic oligonucleotide

<400> SEQUENCE: 44
guauuuagca uguuccca                                              18

<210> SEQ ID NO 45
<211> LENGTH: 18
<212> TYPE: RNA
<213> ORGANISM: Artificial
<220> FEATURE:
<223> OTHER INFORMATION: synthetic oligonucleotide

<400> SEQUENCE: 45
caggaauuug ugucuuuc                                              18

<210> SEQ ID NO 46
<211> LENGTH: 21
<212> TYPE: DNA
<213> ORGANISM: Artificial
<220> FEATURE:
<223> OTHER INFORMATION: synthetic oligonucleotide

<400> SEQUENCE: 46
ucuguuagcc acugauuaaa u                                          21

<210> SEQ ID NO 47
<211> LENGTH: 3685
<212> TYPE: PRT
<213> ORGANISM: Homo sapiens

<400> SEQUENCE: 47
```

| Met | Leu | Trp | Trp | Glu | Glu | Val | Glu | Asp | Cys | Tyr | Glu | Arg | Glu | Asp |
|---|---|---|---|---|---|---|---|---|---|---|---|---|---|---|
| 1 |  |  |  | 5 |  |  |  |  | 10 |  |  |  |  | 15 |

Val

| Gln | Lys | Lys | Thr | Phe | Thr | Lys | Trp | Val | Asn | Ala | Gln | Phe | Ser | Lys | Phe |
|---|---|---|---|---|---|---|---|---|---|---|---|---|---|---|---|
|  |  |  | 20 |  |  |  |  | 25 |  |  |  |  | 30 |  |  |

| Gly | Lys | Gln | His | Ile | Glu | Asn | Leu | Phe | Ser | Asp | Leu | Gln | Asp | Gly | Arg |
|---|---|---|---|---|---|---|---|---|---|---|---|---|---|---|---|
|  |  |  | 35 |  |  |  |  | 40 |  |  |  |  | 45 |  |  |

| Arg | Leu | Leu | Asp | Leu | Leu | Glu | Gly | Leu | Thr | Gly | Gln | Lys | Leu | Pro | Lys |
|---|---|---|---|---|---|---|---|---|---|---|---|---|---|---|---|
| 50 |  |  |  |  | 55 |  |  |  |  | 60 |  |  |  |  |  |

| Glu | Lys | Gly | Ser | Thr | Arg | Val | His | Ala | Leu | Asn | Asn | Val | Asn | Lys | Ala |
|---|---|---|---|---|---|---|---|---|---|---|---|---|---|---|---|
| 65 |  |  |  |  | 70 |  |  |  |  | 75 |  |  |  |  | 80 |

| Leu | Arg | Val | Leu | Gln | Asn | Asn | Asn | Val | Asp | Leu | Val | Asn | Ile | Gly | Ser |
|---|---|---|---|---|---|---|---|---|---|---|---|---|---|---|---|
|  |  |  |  | 85 |  |  |  |  | 90 |  |  |  |  | 95 |  |

| Thr | Asp | Ile | Val | Asp | Gly | Asn | His | Lys | Leu | Thr | Leu | Gly | Leu | Ile | Trp |
|---|---|---|---|---|---|---|---|---|---|---|---|---|---|---|---|
|  |  |  | 100 |  |  |  |  | 105 |  |  |  |  | 110 |  |  |

| Asn | Ile | Ile | Leu | His | Trp | Gln | Val | Lys | Asn | Val | Met | Lys | Asn | Ile | Met |
|---|---|---|---|---|---|---|---|---|---|---|---|---|---|---|---|
|  |  |  | 115 |  |  |  |  | 120 |  |  |  |  | 125 |  |  |

| Ala | Gly | Leu | Gln | Gln | Thr | Asn | Ser | Glu | Lys | Ile | Leu | Leu | Ser | Trp | Val |
|---|---|---|---|---|---|---|---|---|---|---|---|---|---|---|---|
|  | 130 |  |  |  |  | 135 |  |  |  |  | 140 |  |  |  |  |

| Arg | Gln | Ser | Thr | Arg | Asn | Tyr | Pro | Gln | Val | Asn | Val | Ile | Asn | Phe | Thr |
|---|---|---|---|---|---|---|---|---|---|---|---|---|---|---|---|
| 145 |  |  |  |  | 150 |  |  |  |  | 155 |  |  |  |  | 160 |

| Thr | Ser | Trp | Ser | Asp | Gly | Leu | Ala | Leu | Asn | Ala | Leu | Ile | His | Ser | His |
|---|---|---|---|---|---|---|---|---|---|---|---|---|---|---|---|
|  |  |  | 165 |  |  |  |  | 170 |  |  |  |  | 175 |  |  |

| Arg | Pro | Asp | Leu | Phe | Asp | Trp | Asn | Ser | Val | Val | Cys | Gln | Gln | Ser | Ala |
|---|---|---|---|---|---|---|---|---|---|---|---|---|---|---|---|
|  |  |  | 180 |  |  |  |  | 185 |  |  |  |  | 190 |  |  |

| Thr | Gln | Arg | Leu | Glu | His | Ala | Phe | Asn | Ile | Ala | Arg | Tyr | Gln | Leu | Gly |
|---|---|---|---|---|---|---|---|---|---|---|---|---|---|---|---|
|  |  |  | 195 |  |  |  |  | 200 |  |  |  |  | 205 |  |  |

Ile Glu Lys Leu Leu Asp Pro Glu Asp Val Asp Thr Thr Tyr Pro Asp

```
            210                 215                 220
Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                    245                 250                 255

Pro Pro Lys Val Thr Lys Glu Glu His Phe Gln Leu His His Gln Met
                260                 265                 270

His Tyr Ser Gln Gln Ile Thr Val Ser Leu Ala Gln Gly Tyr Glu Arg
            275                 280                 285

Thr Ser Ser Pro Lys Pro Arg Phe Lys Ser Tyr Ala Tyr Thr Gln Ala
        290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                    325                 330                 335

Ser Glu Val Asn Leu Asp Arg Tyr Gln Thr Ala Leu Glu Glu Val Leu
                340                 345                 350

Ser Trp Leu Leu Ser Ala Glu Asp Thr Leu Gln Ala Gln Gly Glu Ile
            355                 360                 365

Ser Asn Asp Val Glu Val Val Lys Asp Gln Phe His Thr His Glu Gly
        370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                    405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Arg Val
            435                 440                 445

Leu Met Asp Leu Gln Asn Gln Lys Leu Lys Glu Leu Asn Asp Trp Leu
        450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                    485                 490                 495

Gln Glu Asp Leu Glu Gln Glu Gln Val Arg Val Asn Ser Leu Thr His
                500                 505                 510

Met Val Val Val Asp Glu Ser Ser Gly Asp His Ala Thr Ala Ala
            515                 520                 525

Leu Glu Glu Gln Leu Lys Val Leu Gly Asp Arg Trp Ala Asn Ile Cys
        530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                    565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
            595                 600                 605

Asp Leu Glu Lys Lys Lys Gln Ser Met Gly Lys Leu Tyr Ser Leu Lys
        610                 615                 620

Gln Asp Leu Leu Ser Thr Leu Lys Asn Lys Ser Val Thr Gln Lys Thr
625                 630                 635                 640
```

```
Glu Ala Trp Leu Asp Asn Phe Ala Arg Cys Trp Asp Asn Leu Val Gln
            645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Glu Leu Pro
            690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
            725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
            755                 760                 765

Glu Lys Ala Glu Lys Phe Arg Lys Leu Gln Asp Ala Ser Arg Ser Ala
            770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
            805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
            835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
            885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
            915                 920                 925

Glu Lys Glu Leu Gln Thr Ile Phe Asp Thr Leu Pro Pro Met Arg Tyr
            930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
            965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
            995                 1000                1005

Lys Ala Pro Ser Glu Ile Ser Arg Lys Tyr Gln Ser Glu Phe Glu
            1010                1015                1020

Glu Ile Glu Gly Arg Trp Lys Lys Leu Ser Ser Gln Leu Val Glu
            1025                1030                1035

His Cys Gln Lys Leu Glu Glu Gln Met Asn Lys Leu Arg Lys Ile
            1040                1045                1050
```

```
Gln Asn His Ile Gln Thr Leu Lys Lys Trp Met Ala Glu Val Asp
1055                1060                1065

Val Phe Leu Lys Glu Glu Trp Pro Ala Leu Gly Asp Ser Glu Ile
1070                1075                1080

Leu Lys Lys Gln Leu Lys Gln Cys Arg Leu Leu Val Ser Asp Ile
1085                1090                1095

Gln Thr Ile Gln Pro Ser Leu Asn Ser Val Asn Glu Gly Gly Gln
1100                1105                1110

Lys Ile Lys Asn Glu Ala Glu Pro Glu Phe Ala Ser Arg Leu Glu
1115                1120                1125

Thr Glu Leu Lys Glu Leu Asn Thr Gln Trp Asp His Met Cys Gln
1130                1135                1140

Gln Val Tyr Ala Arg Lys Glu Ala Leu Lys Gly Gly Leu Glu Lys
1145                1150                1155

Thr Val Ser Leu Gln Lys Asp Leu Ser Glu Met His Glu Trp Met
1160                1165                1170

Thr Gln Ala Glu Glu Glu Tyr Leu Glu Arg Asp Phe Glu Tyr Lys
1175                1180                1185

Thr Pro Asp Glu Leu Gln Lys Ala Val Glu Glu Met Lys Arg Ala
1190                1195                1200

Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
```

-continued

```
            1445                1450                1455
Arg Leu Phe Gln Lys Pro Ala Asn Phe Glu Gln Arg Leu Gln Glu
        1460                1465                1470
Ser Lys Met Ile Leu Asp Glu Val Lys Met His Leu Pro Ala Leu
        1475                1480                1485
Glu Thr Lys Ser Val Glu Gln Glu Val Val Gln Ser Gln Leu Asn
        1490                1495                1500
His Cys Val Asn Leu Tyr Lys Ser Leu Ser Glu Val Lys Ser Glu
        1505                1510                1515
Val Glu Met Val Ile Lys Thr Gly Arg Gln Ile Val Gln Lys Lys
        1520                1525                1530
Gln Thr Glu Asn Pro Lys Glu Leu Asp Glu Arg Val Thr Ala Leu
        1535                1540                1545
Lys Leu His Tyr Asn Glu Leu Gly Ala Lys Val Thr Glu Arg Lys
        1550                1555                1560
Gln Gln Leu Glu Lys Cys Leu Lys Leu Ser Arg Lys Met Arg Lys
        1565                1570                1575
Glu Met Asn Val Leu Thr Glu Trp Leu Ala Ala Thr Asp Met Glu
        1580                1585                1590
Leu Thr Lys Arg Ser Ala Val Glu Gly Met Pro Ser Asn Leu Asp
        1595                1600                1605
Ser Glu Val Ala Trp Gly Lys Ala Thr Gln Lys Glu Ile Glu Lys
        1610                1615                1620
Gln Lys Val His Leu Lys Ser Ile Thr Glu Val Gly Glu Ala Leu
        1625                1630                1635
Lys Thr Val Leu Gly Lys Lys Glu Thr Leu Val Glu Asp Lys Leu
        1640                1645                1650
Ser Leu Leu Asn Ser Asn Trp Ile Ala Val Thr Ser Arg Ala Glu
        1655                1660                1665
Glu Trp Leu Asn Leu Leu Leu Glu Tyr Gln Lys His Met Glu Thr
        1670                1675                1680
Phe Asp Gln Asn Val Asp His Ile Thr Lys Trp Ile Ile Gln Ala
        1685                1690                1695
Asp Thr Leu Leu Asp Glu Ser Glu Lys Lys Lys Pro Gln Gln Lys
        1700                1705                1710
Glu Asp Val Leu Lys Arg Leu Lys Ala Glu Leu Asn Asp Ile Arg
        1715                1720                1725
Pro Lys Val Asp Ser Thr Arg Asp Gln Ala Ala Asn Leu Met Ala
        1730                1735                1740
Asn Arg Gly Asp His Cys Arg Lys Leu Val Glu Pro Gln Ile Ser
        1745                1750                1755
Glu Leu Asn His Arg Phe Ala Ala Ile Ser His Arg Ile Lys Thr
        1760                1765                1770
Gly Lys Ala Ser Ile Pro Leu Lys Glu Leu Glu Gln Phe Asn Ser
        1775                1780                1785
Asp Ile Gln Lys Leu Leu Glu Pro Leu Glu Ala Glu Ile Gln Gln
        1790                1795                1800
Gly Val Asn Leu Lys Glu Glu Asp Phe Asn Lys Asp Met Asn Glu
        1805                1810                1815
Asp Asn Glu Gly Thr Val Lys Glu Leu Leu Gln Arg Gly Asp Asn
        1820                1825                1830
Leu Gln Gln Arg Ile Thr Asp Glu Arg Lys Arg Glu Glu Ile Lys
        1835                1840                1845
```

-continued

Ile Lys Gln Gln Leu Leu Gln Thr Lys His Asn Ala Leu Lys Asp
1850                1855                1860

Leu Arg Ser Gln Arg Arg Lys Ala Leu Glu Ile Ser His Gln
1865                1870                1875

Trp Tyr Gln Tyr Lys Arg Gln Ala Asp Asp Leu Leu Lys Cys Leu
1880                1885                1890

Asp Asp Ile Glu Lys Lys Leu Ala Ser Leu Pro Glu Pro Arg Asp
1895                1900                1905

Glu Arg Lys Ile Lys Glu Ile Asp Arg Glu Leu Gln Lys Lys Lys
1910                1915                1920

Glu Glu Leu Asn Ala Val Arg Arg Gln Ala Glu Gly Leu Ser Glu
1925                1930                1935

Asp Gly Ala Ala Met Ala Val Glu Pro Thr Gln Ile Gln Leu Ser
1940                1945                1950

Lys Arg Trp Arg Glu Ile Glu Ser Lys Phe Ala Gln Phe Arg Arg
1955                1960                1965

Leu Asn Phe Ala Gln Ile His Thr Val Arg Glu Glu Thr Met Met
1970                1975                1980

Val Met Thr Glu Asp Met Pro Leu Glu Ile Ser Tyr Val Pro Ser
1985                1990                1995

Thr Tyr Leu Thr Glu Ile Thr His Val Ser Gln Ala Leu Leu Glu
2000                2005                2010

Val Glu Gln Leu Leu Asn Ala Pro Asp Leu Cys Ala Lys Asp Phe
2015                2020                2025

Glu Asp Leu Phe Lys Gln Glu Glu Ser Leu Lys Asn Ile Lys Asp
2030                2035                2040

Ser Leu Gln Gln Ser Ser Gly Arg Ile Asp Ile Ile His Ser Lys
2045                2050                2055

Lys Thr Ala Ala Leu Gln Ser Ala Thr Pro Val Glu Arg Val Lys
2060                2065                2070

Leu Gln Glu Ala Leu Ser Gln Leu Asp Phe Gln Trp Glu Lys Val
2075                2080                2085

Asn Lys Met Tyr Lys Asp Arg Gln Gly Arg Phe Asp Arg Ser Val
2090                2095                2100

Glu Lys Trp Arg Arg Phe His Tyr Asp Ile Lys Ile Phe Asn Gln
2105                2110                2115

Trp Leu Thr Glu Ala Glu Gln Phe Leu Arg Lys Thr Gln Ile Pro
2120                2125                2130

Glu Asn Trp Glu His Ala Lys Tyr Lys Trp Tyr Leu Lys Glu Leu
2135                2140                2145

Gln Asp Gly Ile Gly Gln Arg Gln Thr Val Val Arg Thr Leu Asn
2150                2155                2160

Ala Thr Gly Glu Glu Ile Ile Gln Gln Ser Ser Lys Thr Asp Ala
2165                2170                2175

Ser Ile Leu Gln Glu Lys Leu Gly Ser Leu Asn Leu Arg Trp Gln
2180                2185                2190

Glu Val Cys Lys Gln Leu Ser Asp Arg Lys Lys Arg Leu Glu Glu
2195                2200                2205

Gln Lys Asn Ile Leu Ser Glu Phe Gln Arg Asp Leu Asn Glu Phe
2210                2215                2220

Val Leu Trp Leu Glu Glu Ala Asp Asn Ile Ala Ser Ile Pro Leu
2225                2230                2235

-continued

Glu Pro Gly Lys Glu Gln Gln Leu Lys Glu Lys Leu Glu Gln Val
    2240                2245                2250

Lys Leu Leu Val Glu Glu Leu Pro Leu Arg Gln Gly Ile Leu Lys
    2255                2260                2265

Gln Leu Asn Glu Thr Gly Gly Pro Val Leu Val Ser Ala Pro Ile
    2270                2275                2280

Ser Pro Glu Glu Gln Asp Lys Leu Glu Asn Lys Leu Lys Gln Thr
    2285                2290                2295

Asn Leu Gln Trp Ile Lys Val Ser Arg Ala Leu Pro Glu Lys Gln
    2300                2305                2310

Gly Glu Ile Glu Ala Gln Ile Lys Asp Leu Gly Gln Leu Glu Lys
    2315                2320                2325

Lys Leu Glu Asp Leu Glu Glu Gln Leu Asn His Leu Leu Leu Trp
    2330                2335                2340

Leu Ser Pro Ile Arg Asn Gln Leu Glu Ile Tyr Asn Gln Pro Asn
    2345                2350                2355

Gln Glu Gly Pro Phe Asp Val Gln Glu Thr Glu Ile Ala Val Gln
    2360                2365                2370

Ala Lys Gln Pro Asp Val Glu Glu Ile Leu Ser Lys Gly Gln His
    2375                2380                2385

Leu Tyr Lys Glu Lys Pro Ala Thr Gln Pro Val Lys Arg Lys Leu
    2390                2395                2400

Glu Asp Leu Ser Ser Glu Trp Lys Ala Val Asn Arg Leu Leu Gln
    2405                2410                2415

Glu Leu Arg Ala Lys Gln Pro Asp Leu Ala Pro Gly Leu Thr Thr
    2420                2425                2430

Ile Gly Ala Ser Pro Thr Gln Thr Val Thr Leu Val Thr Gln Pro
    2435                2440                2445

Val Val Thr Lys Glu Thr Ala Ile Ser Lys Leu Glu Met Pro Ser
    2450                2455                2460

Ser Leu Met Leu Glu Val Pro Ala Leu Ala Asp Phe Asn Arg Ala
    2465                2470                2475

Trp Thr Glu Leu Thr Asp Trp Leu Ser Leu Leu Asp Gln Val Ile
    2480                2485                2490

Lys Ser Gln Arg Val Met Val Gly Asp Leu Glu Asp Ile Asn Glu
    2495                2500                2505

Met Ile Ile Lys Gln Lys Ala Thr Met Gln Asp Leu Glu Gln Arg
    2510                2515                2520

Arg Pro Gln Leu Glu Glu Leu Ile Thr Ala Ala Gln Asn Leu Lys
    2525                2530                2535

Asn Lys Thr Ser Asn Gln Glu Ala Arg Thr Ile Ile Thr Asp Arg
    2540                2545                2550

Ile Glu Arg Ile Gln Asn Gln Trp Asp Glu Val Gln Glu His Leu
    2555                2560                2565

Gln Asn Arg Arg Gln Gln Leu Asn Glu Met Leu Lys Asp Ser Thr
    2570                2575                2580

Gln Trp Leu Glu Ala Lys Glu Glu Ala Glu Gln Val Leu Gly Gln
    2585                2590                2595

Ala Arg Ala Lys Leu Glu Ser Trp Lys Glu Gly Pro Tyr Thr Val
    2600                2605                2610

Asp Ala Ile Gln Lys Lys Ile Thr Glu Thr Lys Gln Leu Ala Lys
    2615                2620                2625

Asp Leu Arg Gln Trp Gln Thr Asn Val Asp Val Ala Asn Asp Leu

-continued

```
                2630                2635                2640
Ala Leu Lys Leu Leu Arg Asp Tyr Ser Ala Asp Thr Arg Lys
    2645                2650                2655

Val His Met Ile Thr Glu Asn Ile Asn Ala Ser Trp Arg Ser Ile
2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850

Glu Leu Lys Thr Lys Glu Pro Val Ile Met Ser Thr Leu Glu Thr
    2855                2860                2865

Val Arg Ile Phe Leu Thr Glu Gln Pro Leu Glu Gly Leu Glu Lys
    2870                2875                2880

Leu Tyr Gln Glu Pro Arg Glu Leu Pro Pro Glu Glu Arg Ala Gln
    2885                2890                2895

Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970

His Leu Glu Lys Val Lys Ala Leu Arg Gly Glu Ile Ala Pro Leu
    2975                2980                2985

Lys Glu Asn Val Ser His Val Asn Asp Leu Ala Arg Gln Leu Thr
    2990                2995                3000

Thr Leu Gly Ile Gln Leu Ser Pro Tyr Asn Leu Ser Thr Leu Glu
    3005                3010                3015

Asp Leu Asn Thr Arg Trp Lys Leu Leu Gln Val Ala Val Glu Asp
    3020                3025                3030
```

-continued

```
Arg Val Arg Gln Leu His Glu Ala His Arg Asp Phe Gly Pro Ala
3035               3040                3045
Ser Gln His Phe Leu Ser Thr Ser Val Gln Gly Pro Trp Glu Arg
3050               3055                3060
Ala Ile Ser Pro Asn Lys Val Pro Tyr Tyr Ile Asn His Glu Thr
3065               3070                3075
Gln Thr Thr Cys Trp Asp His Pro Lys Met Thr Glu Leu Tyr Gln
3080               3085                3090
Ser Leu Ala Asp Leu Asn Asn Val Arg Phe Ser Ala Tyr Arg Thr
3095               3100                3105
Ala Met Lys Leu Arg Arg Leu Gln Lys Ala Leu Cys Leu Asp Leu
3110               3115                3120
Leu Ser Leu Ser Ala Ala Cys Asp Ala Leu Asp Gln His Asn Leu
3125               3130                3135
Lys Gln Asn Asp Gln Pro Met Asp Ile Leu Gln Ile Ile Asn Cys
3140               3145                3150
Leu Thr Thr Ile Tyr Asp Arg Leu Glu Gln Glu His Asn Asn Leu
3155               3160                3165
Val Asn Val Pro Leu Cys Val Asp Met Cys Leu Asn Trp Leu Leu
3170               3175                3180
Asn Val Tyr Asp Thr Gly Arg Thr Gly Arg Ile Arg Val Leu Ser
3185               3190                3195
Phe Lys Thr Gly Ile Ile Ser Leu Cys Lys Ala His Leu Glu Asp
3200               3205                3210
Lys Tyr Arg Tyr Leu Phe Lys Gln Val Ala Ser Ser Thr Gly Phe
3215               3220                3225
Cys Asp Gln Arg Arg Leu Gly Leu Leu Leu His Asp Ser Ile Gln
3230               3235                3240
Ile Pro Arg Gln Leu Gly Glu Val Ala Ser Phe Gly Gly Ser Asn
3245               3250                3255
Ile Glu Pro Ser Val Arg Ser Cys Phe Gln Phe Ala Asn Asn Lys
3260               3265                3270
Pro Glu Ile Glu Ala Ala Leu Phe Leu Asp Trp Met Arg Leu Glu
3275               3280                3285
Pro Gln Ser Met Val Trp Leu Pro Val Leu His Arg Val Ala Ala
3290               3295                3300
Ala Glu Thr Ala Lys His Gln Ala Lys Cys Asn Ile Cys Lys Glu
3305               3310                3315
Cys Pro Ile Ile Gly Phe Arg Tyr Arg Ser Leu Lys His Phe Asn
3320               3325                3330
Tyr Asp Ile Cys Gln Ser Cys Phe Phe Ser Gly Arg Val Ala Lys
3335               3340                3345
Gly His Lys Met His Tyr Pro Met Val Glu Tyr Cys Thr Pro Thr
3350               3355                3360
Thr Ser Gly Glu Asp Val Arg Asp Phe Ala Lys Val Leu Lys Asn
3365               3370                3375
Lys Phe Arg Thr Lys Arg Tyr Phe Ala Lys His Pro Arg Met Gly
3380               3385                3390
Tyr Leu Pro Val Gln Thr Val Leu Glu Gly Asp Asn Met Glu Thr
3395               3400                3405
Pro Val Thr Leu Ile Asn Phe Trp Pro Val Asp Ser Ala Pro Ala
3410               3415                3420
```

-continued

```
Ser Ser Pro Gln Leu Ser His Asp Asp Thr His Ser Arg Ile Glu
    3425            3430            3435

His Tyr Ala Ser Arg Leu Ala Glu Met Glu Asn Ser Asn Gly Ser
    3440            3445            3450

Tyr Leu Asn Asp Ser Ile Ser Pro Asn Glu Ser Ile Asp Asp Glu
    3455            3460            3465

His Leu Leu Ile Gln His Tyr Cys Gln Ser Leu Asn Gln Asp Ser
    3470            3475            3480

Pro Leu Ser Gln Pro Arg Ser Pro Ala Gln Ile Leu Ile Ser Leu
    3485            3490            3495

Glu Ser Glu Glu Arg Gly Glu Leu Glu Arg Ile Leu Ala Asp Leu
    3500            3505            3510

Glu Glu Glu Asn Arg Asn Leu Gln Ala Glu Tyr Asp Arg Leu Lys
    3515            3520            3525

Gln Gln His Glu His Lys Gly Leu Ser Pro Leu Pro Ser Pro Pro
    3530            3535            3540

Glu Met Met Pro Thr Ser Pro Gln Ser Pro Arg Asp Ala Glu Leu
    3545            3550            3555

Ile Ala Glu Ala Lys Leu Leu Arg Gln His Lys Gly Arg Leu Glu
    3560            3565            3570

Ala Arg Met Gln Ile Leu Glu Asp His Asn Lys Gln Leu Glu Ser
    3575            3580            3585

Gln Leu His Arg Leu Arg Gln Leu Leu Glu Gln Pro Gln Ala Glu
    3590            3595            3600

Ala Lys Val Asn Gly Thr Thr Val Ser Ser Pro Ser Thr Ser Leu
    3605            3610            3615

Gln Arg Ser Asp Ser Ser Gln Pro Met Leu Leu Arg Val Val Gly
    3620            3625            3630

Ser Gln Thr Ser Asp Ser Met Gly Glu Glu Asp Leu Leu Ser Pro
    3635            3640            3645

Pro Gln Asp Thr Ser Thr Gly Leu Glu Glu Val Met Glu Gln Leu
    3650            3655            3660

Asn Asn Ser Phe Pro Ser Ser Arg Gly Arg Asn Thr Pro Gly Lys
    3665            3670            3675

Pro Met Arg Glu Asp Thr Met
    3680            3685
```

METHOD FOR EFFICIENT EXON (44) SKIPPING IN DUCHENNE MUSCULAR DYSTROPHY AND ASSOCIATED MEANS

CROSS REFERENCE

This application is a continuation of U.S. application Ser. No. 12/992,218 filed Nov. 11, 2010, which is a continuation of PCT application No. PCT/NL2009/050258 filed May 14, 2009, which claims priority to European application No. EP 08156193.8 filed May 14, 2008, and to U.S. provisional application No. 61/128,010 filed May 15, 2008, the contents of each of which is incorporated by reference in their entirety.

The present specification is being filed with a Sequence Listing in Computer Readable Form (CFR), which is entitled 11808-325-999_SEQLIST.txt of 41,702 bytes in size and was created Oct. 8, 2018; the content of which is incorporated herein by reference in its entirety.

FIELD OF THE INVENTION

The invention relates to the field of genetics, more specifically human genetics. The invention in particular relates to the modulation of splicing of the human Duchenne Muscular Dystrophy gene.

BACKGROUND

Myopathies are disorders that result in functional impairment of muscles. Muscular dystrophy (MD) refers to genetic diseases that are characterized by progressive weakness and degeneration of skeletal muscles. Duchenne muscular dystrophy (DMD) and Becker muscular dystrophy (BMD) are the most common childhood forms of muscular dystrophy. They are recessive disorders and because the gene responsible for DMD and BMD resides on the X-chromosome, mutations mainly affect males with an incidence of about 1 in 3500 boys.

DMD and BMD are caused by genetic defects in the DMD gene encoding dystrophin, a muscle protein that is required for interactions between the cytoskeleton and the extracellular matrix to maintain muscle fiber stability during contraction. DMD is a severe, lethal neuromuscular disorder resulting in a dependency on wheelchair support before the age of 12 and DMD patients often die before the age of thirty due to respiratory- or heart failure. In contrast, BMD patients often remain ambulatory until later in life, and have near normal life expectancies. DMD mutations in the dystrophin gene are characterized by frame shifting insertions or deletions or nonsense point mutations, resulting in the absence of functional dystrophin. BMD mutations in general keep the reading frame intact, allowing synthesis of a partly functional dystrophin.

Several possible treatments have been investigated over the last 20 years, including myoblast-transplantation, DNA-targeted gene therapy, and antisense-mediated exon skipping (van Deutekom and van Ommen, (2003), Nat. Rev. Genet., 4(10):774-83). Antisense-mediated exon skipping aims at transforming out-of-frame mutations present in DMD patients into in-frame BMD-like mutations that result in synthesis of an at least partially functional dystrophin, which will prolong the viability of the muscles (Aartsma-Rus and van Ommen, (2007), RNA, 13(10): 1609-24).

Exon skipping can be induced by antisense oligonucleotides (AON) directed against the splice donor or splice acceptor site of a splice junction that are involved in the enzymatic process of exon joining, or against exon-internal sequences. In general, splice donor and splice acceptor sites comprise conserved sequences and targeting these sequences has the inevitable risk of co-targeting splice sites of additional exons from DMD or other gene transcripts.

Exon 44 of the DMD gene consists of 148 base pairs. Therapeutic skipping of exon 44 would restore the correct reading frame in DMD patients having deletions including but not limited to exons 03-43, 05-43, 06-43, 10-43, 13-43, 14-43, 17-43, 19-43, 28-43, 30-43, 31-43, 33-43, 34-43, 35-43, 36-43, 37-43, 38-43, 40-43, 41-43, 42-43, 43, 45, 45-54, and 45-68, or having a duplication of exon 44. Furthermore, for some DMD patients the mutations are such that the simultaneous skipping of one or more exons is required in addition to exon 44 skipping to restore the reading frame. Non-limiting examples of such mutations are nonsense point mutations in the flanking exons 43 or 45, requiring exon 43+44 skipping or exon 44+45 skipping respectively. The aforementioned mutations in total occur in about 6-8% of all DMD patients. The majority of resulting dystrophin proteins will be truncated in the central rod domain of the protein, leaving the essential N-terminal actin-binding domain and the C-terminal domain binding to dystrobrevin and syntrophin, and the β-dystroglycan-binding C-terminal cysteine-rich domain, intact.

DETAILED DESCRIPTION OF THE EMBODIMENTS

The present invention identifies four different regions in exon 44 that are particularly suited for inducing skipping of exon 44. The invention thus provides a method for modulating splicing of exon 44 of the DMD gene in a cell, the method comprising providing said cell with a molecule that binds to a nucleotide sequence comprising SEQ ID NO. 1: 5'-GUGGCUAACAGAAGCU; SEQ ID NO. 2: 5'-GGGAACAUGCUAAAUAC, SEQ ID NO. 3: 5'-AGACACAAAUUCCUGAGA, or SEQ ID NO. 4: 5'-CUGUUGAGAAA. This molecule preferably binds or is complementary to any of SEQ ID NO: 1, 2, 3, or 4 when SEQ ID NO:1, 2, 3, or 4 is present within exon 44 of the DMD pre-mRNA.

Throughout the application, the expression "inducing skipping" is synonymous of "modulating splicing".

It was found that a molecule that binds to a nucleotide sequence comprising SEQ ID NO. 1: 5'-GUGGCUAACAGAAGCU; SEQ ID NO. 2: 5'-GGGAACAUGCUAAAUAC, SEQ ID NO. 3: 5'-AGACACAAAUUCCUGAGA, or SEQ ID NO. 4: 5'-CUGUUGAGAAA results in highly efficient skipping of exon 44 in cells provided with this molecule. Furthermore, none of the indicated sequences is derived from conserved parts of splice junction sites. Therefore, said molecule is not likely to mediate differential splicing of other exons from the DMD pre-mRNA or exons from other genes. In addition, other (immuno)toxicity is preferably avoided by avoiding CpG pairs in the molecule that binds to a nucleotide sequence as defined herein above.

Exon skipping refers to the induction in a cell of a mature mRNA that does not contain a particular exon that is normally present therein. Exon skipping is achieved by providing a cell expressing the pre-mRNA of said mRNA, with a molecule capable of interfering with sequences such as, for example, the splice donor or splice acceptor sequence required for allowing the enzymatic process of splicing, or that is capable of interfering with an exon inclusion signal required for recognition of a stretch of nucleotides as an exon to be included into the mRNA. The term pre-mRNA refers to a non-processed or partly processed precursor mRNA that is synthesized from a DNA template in the cell nucleus by transcription.

Certain methods of the invention will alleviate one or more characteristics of a myogenic cell or muscle cell of a DMD patient having deletions including, but not limited to, exons 03-43, 05-43, 06-43, 10-43, 13-43, 14-43, 17-43, 19-43, 28-43, 30-43, 31-43, 33-43, 34-43, 35-43, 36-43, 37-43, 38-43, 40-43, 41-43, 42-43, 43, 45, 45-54, and 45-68, or having a duplication of exon 44. Furthermore, the removal of a flanking exon, such as, for example, exon 43 or exon 45, because of a nonsense point mutation in the flanking exon, will result in an out of frame transcript. The additional skipping of exon 44, in combination with skipping of the flanking exon, will restore the reading frame of the DMD gene in myogenic cells or muscle cells of DMD patients. Non-limiting examples of such mutations are nonsense point mutations in the flanking exons 43 or 45, requiring exon 43+44 skipping or exon 44+45 skipping respectively.

In an embodiment, a method of the invention may also alleviate one or more characteristics of a myogenic cell or muscle cell of a strong BMD patient, to the characteristics of a mild BMD patient. The characteristics of a cell of a DMD or BMD patient include increased calcium uptake by muscle cells, increased collagen synthesis, altered morphology, altered lipid biosynthesis, increased oxidative stress, and/or damaged sarcolemma. Preferred embodiments of a method of the invention are later defined herein.

In one embodiment, a molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 1, 2, 3, or 4 sequence, preferably in the context of exon 44 of DMD may be assessed via techniques known to the skilled person. A preferred technique is gel mobility shift assay as described in EP 1 619 249. In a preferred embodiment, a molecule is said to bind to one of the specified sequences as soon as a binding of said molecule to a labelled sequence SEQ ID NO: 1, 2, 3 or 4 is detectable in a gel mobility shift assay. Alternatively or in combination with previous embodiment, a molecule is an oligonucleotide which is complementary or substantially complementary to SEQ ID NO:1, 2, 3, or 4 or part thereof as later defined herein. The term "substantially" complementary used in this context indicates that one or two or more mismatches may be allowed as long as the functionality, i.e. inducing skipping of exon 44, is still acceptable.

The invention provides a method for designing a molecule, preferably an oligonucleotide able to induce the skipping of exon 44 of the DMD gene. First said oligonucleotide is selected to bind to one of SEQ ID NO: 1, 2, 3, or 4 or parts thereof as earlier defined herein. Subsequently, in a preferred method at least one of the following aspects has to be taken into account for designing, improving said molecule any further:

The molecule does not contain a CpG,
The molecule does not contain a G-quartet motif,
The molecule has acceptable RNA binding kinetics and/or thermodynamic properties.

The presence of a CpG in an oligonucleotide is usually associated with an increased immunogenicity of said oligonucleotide (Dorn and Kippenberger, Curr Opin Mol Ther 2008 10(1) 10-20). This increased immunogenicity is undesired since it may induce the breakdown of muscle fibers. Immunogenicity may be assessed in an animal model by assessing the presence of $CD4^+$ and/or $CD8^+$ cells and/or inflammatory mononucleocyte infiltration in muscle biopsy of said animal. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person. An increase in immunogenicity may be assessed by detecting the presence or an increasing amount of a neutralizing antibody or an antibody recognizing said oligonucleotide using a standard immunoassay.

An oligonucleotide comprising a G-quartet motif has the tendency to form a quadruplex, a multimer or aggregate formed by the Hoogsteen base-pairing of four single-stranded oligonucleotides (Cheng and Van Dyke, Gene. 1997 Sep. 15; 197(1-2):253-60), which is of course not desired: as a result the efficiency of the oligonucleotide is expected to be decreased. Multimerisation or aggregation is preferably assessed by standard polyacrylamide non-denaturing gel electrophoresis techniques known to the skilled person. In a preferred embodiment, less than 20% or 15%, 10%, 7%, 5% or less of a total amount of an oligonucleotide of the invention has the capacity to multimerise or aggregate assessed using the assay mentioned above.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbour model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 65° C. and an acceptable free energy may be ranged between 15 and 45 kcal/mol.

The skilled person may therefore first choose an oligonucleotide as a potential therapeutic compound as binding and/or being complementary to SEQ ID NO:1, 2, 3, or 4 of exon 44 or parts thereof as defined herein. The skilled person may check that said oligonucleotide is able to bind to said sequences as earlier defined herein. Optionally in a second step, he may use the invention to further optimise said oligonucleotide by checking for the absence of CpG, the absence of a G-quartet motif, and/or by optimizing its Tm and/or free energy of the AON-target complex. He may try to design an oligonucleotide wherein no CpG and/or no G-quartet motif are present and/or wherein a more acceptable Tm and/or free energy are obtained by choosing a distinct sequence of exon 44 (for example SEQ ID NO:1, 2, 3, or 4) to which the oligonucleotide is complementary. Alternatively, if an oligonucleotide complementary to a given stretch within SEQ ID NO:1, 2, 3 or 4 of exon 44, comprises a CpG, a G-quartet motif and/or does not have an acceptable Tm and/or free energy, the skilled person may improve any of these parameters by decreasing the length of the oligonucleotide, and/or by choosing a distinct stretch within any of SEQ ID NO: 1, 2, 3, or 4 to which the oligonucleotide is complementary and/or by altering the chemistry of the oligonucleotide.

As an example, if one chooses SEQ ID NO:1, several oligonucleotides were designed which were found to bind this sequence: SEQ ID NO: 5, 41, and 46. The oligonucleotide comprising SEQ ID NO:5 was found to have the most optimal RNA binding kinetics and/or thermodynamic properties, such as the most optimal Tm. When we tested the functionality of these oligonucleotides to induce the skipping of exon 44, it was confirmed that an oligonucleotide comprising SEQ ID NO:5 is the most efficient of these four oligonucleotides. Each of these oligonucleotides is functional in the sense of the invention. However, an oligonucleotide comprising SEQ ID NO:5 is the most preferred oligonucleotide identified that binds and/or is complementary to SEQ ID NO:1.

At any step of the method, an oligonucleotide of the invention is preferably an olignucleotide, which is still able to exhibit an acceptable level of a functional activity. A functional activity of said oligonucleotide is preferably to induce the skipping of exon 44 of the DMD gene to a certain extent, to provide an individual with a functional dystrophin protein and/or mRNA and/or at least in part decreasing the production of an aberrant dystrophin protein and/or mRNA. Each of these features is later defined herein. Such functional activity may be measured in a muscular tissue or in a muscular cell of an individual or in vitro in a cell. The assessment of the functionality may be carried out at the mRNA level, preferably using RT-PCR. The assessment of the functionality may be carried out at the protein level, preferably using western blot analysis or immunofluorescence analysis of cross-sections. In a preferred embodiment, an oligonucleotide is said to induce skipping of exon 44 of a DMD gene, when tested in a muscle cell of a DMD patient, by RT-PCR, the exon 44 skipping percentage is of at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

In a preferred embodiment, such oligonucleotide is preferably a medicament. More preferably, said medicament is for preventing or treating Duchenne Muscular Dystrophy or Becker Muscular Dystrophy in an individual or a patient. As defined herein a DMD pre-mRNA preferably means the pre-mRNA of a DMD gene of a DMD or BMD patient. A patient is preferably intended to mean a patient having DMD or BMD or a patient susceptible to develop DMD or BMD due to his or her genetic background.

In the case of a DMD patient, an oligonucleotide used will preferably correct at least one of the DMD mutations as present in the DMD gene of said patient and therefore will preferably create a dystrophin that will look like a BMD dystrophin: said dystrophin will preferably be a functional dystrophin as later defined herein.

In the case of a BMD patient, an oligonucleotide as used will preferably correct at least one of the BMD mutations as present in the DMD gene of said patient and therefore will preferably create a, or more of a, dystrophin, which will be more functional than the dystrophin which was originally present in said BMD patient. Even more preferably, said medicament increases the production of a functional or more functional dystrophin protein and/or mRNA and/or at least in part decreases the production of an aberrant or less functional dystrophin protein and/or mRNA in an individual.

Preferably, a method of the invention increases production of a more functional dystrophin protein and/or mRNA and/or decreases the production of an aberrant or less functional dystrophin protein and/or mRNA in a patient, by inducing and/or promoting skipping of at least exon 44 of the DMD pre-mRNA as identified herein in one or more cells, preferably muscle cells of said patient. Increasing the production of a more functional dystrophin protein and/or mRNA and/or decreasing the production of an aberrant dystrophin protein and/or mRNA in a patient is typically applied in a DMD patient. Increasing the production of a more functional or functional dystrophin and/or mRNA is typically applied in a BMD patient.

Therefore a preferred method is a method, wherein in a patient or in one or more cells of said patient, production of a more functional or functional dystrophin protein and/or mRNA is increased and/or the production of an aberrant dystrophin protein and/or mRNA in said patient is decreased, wherein the level of said aberrant or more functional dystrophin protein and/or mRNA is assessed by comparison to the level of said dystrophin and/or mRNA in said patient at the onset of the method.

As defined herein, a functional dystrophin is preferably a wild type dystrophin corresponding to a protein having the amino acid sequence as identified in SEQ ID NO: 47. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO: 47. In another embodiment, a functional dystrophin is a dystrophin, which exhibits at least to some extent an activity of a wild type dystrophin. "At least to some extent" preferably means at least 30%, 40%, 50%, 60%, 70%, 80%, 90%, 95% or 100% of a corresponding activity of a wild type functional dystrophin. In this context, an activity of a wild type dystrophin is preferably binding to actin and to the dystrophin-associated glycoprotein complex (DGC)(Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144.). Binding of dystrophin to actin and to the DGC complex may be visualized by either co-immunoprecipitation using total protein extracts or immunofluorescence analysis of cross-sections, from a biopsy of a muscle suspected to be dystrophic, as known to the skilled person.

Individuals suffering from Duchenne muscular dystrophy typically have a mutation in the gene encoding dystrophin that prevents synthesis of the complete protein, i.e. a premature stop prevents the synthesis of the C-terminus of the protein. In Becker muscular dystrophy the dystrophin gene also comprises a mutation compared to the wild type but the mutation does typically not include a premature stop and the C-terminus of the protein is typically synthesized. As a result a functional dystrophin protein is synthesized that has at least the same activity in kind as a wild type protein, although not necessarily the same amount of activity. In a preferred embodiment, a functional dystrophin protein means an in frame dystrophin gene. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The amino acids indicated herein correspond to amino acids of the wild type dystrophin being represented by SEQ ID NO: 47. Exon-skipping for the treatment of DMD is preferably but not exclusively directed to overcome a premature stop in the pre-mRNA by skipping an exon in the rod-domain shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated using an oligonucleotide as defined herein will be provided a dystrophin, which exhibits at least to some extent an activity of a wild type dystrophin. More preferably, if said individual is a Duchenne patient or is suspected to be a Duchenne patient, a functional dystrophin is a dystrophin comparable in functionality to a dystrophin from an individual having BMD: preferably said dystrophin is able to interact with both actin and the DGC, but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The central rod domain of wild type dystrophin comprises 24 spectrin-like repeats (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). For example, a central rod shaped domain of a dystrophin as provided herein may comprise 5 to 23, 10 to 22 or 12 to 18 spectrin-like repeats as long as it can bind to actin and to DGC.

Decreasing the production of an aberrant dystrophin in said patient or in a cell of said patient may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional or less to non-functional or semi-functional dystrophin mRNA or protein. A non-functional pre-mRNA dystrophin is preferably leads to an out of frame dystrophin protein, which means that no dystrophin protein will be produced and/or detected. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in a patient or in a cell of said patient may be assessed at the mRNA level (by RT-PCR analysis) and preferably means that a detectable amount of a functional or in frame dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional or in frame dystrophin mRNA.

Increasing the production of a functional dystrophin in a patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%, 30%, 40%, 50%, 60%, 70%, 80%, 90% or more of the detectable dystrophin protein is a functional dystrophin protein.

An increase or a decrease is preferably assessed in a muscular tissue or in a muscular cell of an individual or a patient by comparison to the amount present in said individual or patient before treatment with said molecule or composition of the invention. Alternatively, the comparison can be made with a muscular tissue or cell of said individual or patient, which has not yet been treated with said oligonucleotide or composition in case the treatment is local.

In a further aspect, there is provided a method for alleviating one or more symptom(s) of Duchenne Muscular Dystrophy or Becker Muscular Dystrophy in an individual or alleviate one or more characteristic(s) of a myogenic or muscle cell of said individual, the method comprising administering to said individual an oligonucleotide or a composition as defined herein.

There is further provided a method for enhancing, inducing or promoting skipping of an exon from a dystrophin pre-mRNA in a cell expressing said pre-mRNA in an individual suffering from Duchenne Muscular Dystrophy or Becker Muscular Dystrophy, the method comprising administering to said individual an oligonucleotide or a composition as defined herein. Further provided is a method for increasing the production of a functional dystrophin protein and/or decreasing the production of an aberrant dystrophin protein in a cell, said cell comprising a pre-mRNA of a dystrophin gene encoding an aberrant dystrophin protein, the method comprising providing said cell with an oligonucleotide or composition of the invention and allowing translation of mRNA produced from splicing of said pre-mRNA. In one embodiment, said method is performed in vivo, for instance using a cell culture. Preferably, said method is in vivo in said individual.

In this context, increasing the production of a functional dystrophin protein has been defined herein.

Alleviating one or more symptom(s) of Duchenne Muscular Dystrophy or Becker Muscular Dystrophy in an individual using a molecule or a composition of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration.) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a molecule or composition of the invention. Detectable improvement or prolongation is preferably a statistically significant improvement or prolongation as described in Hodgetts et al (Hodgetts S., et al, (2006), Neuromuscular Disorders, 16: 591-602).

Alternatively, the alleviation of one or more symptom(s) of Duchenne Muscular Dystrophy or Becker Muscular Dystrophy may be assessed by measuring an improvement of a characteristic of a muscle fiber relating to its function, integrity and/or survival, said characteristic being assessed on the patient self. Such characteristics may be assessed at the cellular, tissue level of a given patient. An alleviation of one or more characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

An oligonucleotide as used herein preferably comprises an antisense oligonucleotide or antisense oligoribonucleotide. In a preferred embodiment an exon skipping technique is applied. Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered product. Technology for exon-skipping is currently directed towards the use of antisense oligonucleotides (AONs). Much of this work is done in the mdx mouse model for Duchenne muscular dystrophy. The mdx mouse carries a nonsense mutation in exon 23. Despite the mdx mutation, which should preclude the synthesis of a functional dystrophin protein, rare, naturally occurring dystrophin positive fibers have been observed in mdx muscle tissue. These dystrophin-positive fibers are thought to have arisen from an apparently naturally occurring exon-skipping mechanism, either due to somatic mutations or through alternative splicing. AONs directed to, respectively, the 3' and/or 5' splice sites of introns 22 and 23 in dystrophin pre-mRNA, have been shown to interfere with factors normally involved in removal of intron 23 so that also exon 23 was removed from the mRNA (Alter J, et al. Systemic delivery of morpholino oligonucleotide restores dystrophin expression bodywide and improves dystrophic pathology. Nat Med 2006; 12(2): 175-7, Lu Q L, et al. Functional amounts of dystrophin produced by skipping the mutated exon in the mdx dystrophic mouse. Nat Med 2003; 6:6, Lu Q L, et al. Systemic delivery of antisense oligoribonucleotide restores dystrophin expression in body-wide skeletal muscles. Proc Natl Acad Sci USA 2005; 102(1):198-203, Mann C J, et al, Improved antisense oligonucleotide induced exon skipping in the mdx mouse model of muscular dystrophy. J Gene Med 2002; 4(6):644-54 or Graham I R, et al, Towards a therapeutic inhibition of dystrophin exon 23 splicing in mdx mouse muscle induced by antisense oligoribonucleotides (splicomers): target sequence optimisation using oligonucleotide arrays. J Gene Med 2004; 6(10):1149-58).

By the targeted skipping of a specific exon, a DMD phenotype is converted into a milder BMD phenotype. The skipping of an exon is preferably induced by the binding of AONs targeting exon-internal sequences. An oligonucleotide directed toward an exon internal sequence typically exhibits no overlap with non-exon sequences. It preferably does not overlap with the splice sites at least not insofar, as these are present in the intron. An oligonucleotide directed toward an exon internal sequence preferably does not contain a sequence complementary to an adjacent intron. Further provided is thus an oligonucleotide according to the invention, wherein said oligonucleotide, or a functional equivalent thereof, is for inhibiting inclusion of an exon of a dystrophin pre-mRNA into mRNA produced from splicing of said pre-mRNA. An exon skipping technique is preferably applied such that the absence of an exon from mRNA produced from dystrophin pre-mRNA generates a coding region for a more functional—albeit shorter—dystrophin protein. In this context, inhibiting inclusion of an exon preferably means that the detection of the original, aberrant dystrophin mRNA and/or protein is decreased as earlier defined herein.

Within the context of the invention, a functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a functional dystrophin protein. Said activity of said functional equivalent is therefore preferably assessed by quantifying the amount of a functional dystrophin protein or by quantifying the amount of a functional dystrophin mRNA. A functional dystrophin protein (or a functional dystrophin mRNA) is herein preferably defined as being a dystrophin protein (or a dystrophin protein encoded by said mRNA) able to bind actin and members of the DGC protein. The assessment of said activity of an oligonucleotide is preferably done by RT-PCR (m-RNA) or by immunofluorescence or Western blot analyses (protein). Said activity is preferably retained to at least some extent when it represents at least 50%, or at least 60%, or at least 70% or at least 80% or at least 90% or at least 95% or more of corresponding activity of said oligonucleotide the functional equivalent derives from. Such activity may be measured in a muscular tissue or in a muscular cell of an individual or in vitro in a cell by comparison to an activity of a corresponding oligonucleotide of said oligonucleotide the functional equivalent derives from. Throughout this application, when the word oligonucleotide is used it may be replaced by a functional equivalent thereof as defined herein.

In a preferred embodiment, an oligonucleotide of the invention, which comprises a sequence that binds and/or is complementary to a sequence of exon 44 of dystrophin pre-mRNAas earlier defined herein is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or even more preferably at least 99%, or even more preferably 100%. In a most preferred embodiment, an oligonucleotide of the invention consists of a sequence that is complementary to part of dystrophin pre-mRNA as defined herein. As an example, an oligonucleotide may comprise a sequence that is complementary to part of dystrophin pre-mRNA as defined herein and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. Preferably, additional flanking sequences are used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridising to the complementary part. In this context, "sufficiently" preferably means that using a gel mobility shift assay as described in example 1 of EP 1 619 249, binding of an oligonucleotide is detectable. Optionally, said oligonucleotide may further be tested by transfection into muscle cells of patients. Skipping of the targeted exon may be assessed by RT-PCR (as described in EP 1 619 249). The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides.

A preferred molecule of the invention comprises or consists of a nucleotide-based sequence that is antisense to a sequence selected from exon 44 of the DMD pre-mRNA. The sequence of the DMD pre-mRNA is preferably selected from SEQ ID NO 1: 5'-GUGGCUAACAGAAGCU; SEQ ID NO 2: 5'-GGGAACAUGCUAAAUAC, SEQ ID NO 3: 5'-AGACACAAAUUCCUGAGA, and SEQ ID NO 4: 5'-CUGUUGAGAAA.

A molecule of the invention is preferably an isolated molecule.

A molecule of the invention is preferably a nucleic acid molecule or a nucleotide-based molecule or an oligonucleotide or an antisense oligonucleotide which binds and/or is complementary to a sequence of exon 44 selected from SEQ ID NO:1, 2, 3 or 4.

A preferred molecule of the invention comprises or consists of from about 8 to about 60 nucleotides, more preferred from about 10 to about 50 nucleotides, more preferred from about 17 to about 40 nucleotides, more preferred from about 18 to about 30 nucleotides, more preferred from about 18 to about 24 nucleotides, most preferred about 20 nucleotides, such as 18 nucleotides, 19 nucleotides, 20 nucleotides, 21 nucleotides, 22 nucleotides or 23 nucleotides.

A preferred molecule of the invention comprises or consists of from 8 to 60 nucleotides, more preferred from 10 to 50 nucleotides, more preferred from 17 to 40 nucleotides, more preferred from 18 to 30 nucleotides, more preferred from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In certain embodiments, the invention provides a molecule comprising or consisting of an antisense nucleotide sequence selected from the antisense nucleotide sequences depicted in Table 1A.

A molecule or nucleic acid molecule of the invention that binds and/or is complementary and/or is antisense to a nucleotide having nucleotide sequence: SEQ ID NO 1: 5'-GUGGCUAACAGAAGCU preferably comprises or consists of the antisense nucleotide sequence of SEQ ID NO 5; SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO: 41 or SEQ ID NO: 46. A preferred molecule that targets this region of the DMD pre-mRNA comprises or consists of the antisense nucleotide sequence of SEQ ID NO:5, SEQ ID NO 41, or SEQ ID NO 46. Most preferred oligonucleotide comprises or consists of the antisense nucleotide sequence of SEQ ID NO:5.

In a more preferred embodiment, the invention provides a molecule comprising or consisting of the antisense nucleotide sequence SEQ ID NO 5: 5'-UCAGCUUCUGUUAGC-CACUG. It was found that this molecule is very efficient in modulating splicing of exon 44 of the DMD gene in muscle cells. This preferred molecule of the invention comprising SEQ ID NO:5 comprises from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, or preferably comprises or consists of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In another preferred embodiment, the invention provides a molecule comprising or consisting of the antisense nucleotide sequence SEQ ID NO 41 or 46. These preferred molecules of the invention comprising either SEQ ID NO: 41 or SEQ ID NO: 46 further comprise from 18 to 60, more preferred from 18 to 55, more preferred from 20 to 53, more preferred from 24 to 50, more preferred from 25 to 45, more preferred from 26 to 43, more preferred from 27 to 41, more preferred from 28 to 40, more preferred from 29 to 40, or preferably comprises or consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In a further embodiment, a molecule of the invention that is antisense to SEQ ID NO 2: 5'-GGGAACAUGC-UAAAUAC preferably comprises or consists of the antisense nucleotide sequence of SEQ ID NO 35 or SEQ ID NO 36. These preferred molecules of the invention comprising either SEQ ID NO: 35 or SEQ ID NO: 36, further comprise from 17 to 60 nucleotides, more preferred from 18 to 30 nucleotides, more preferred from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In yet a further embodiment, a molecule of the invention that is antisense to SEQ ID NO 3: 5'-AGACACAAAUUC-CUGAGA preferably comprises or consists of the antisense nucleotide sequence of SEQ ID NO 39 or SEQ ID NO 40. These preferred molecules of the invention comprising either SEQ ID NO: 39 or SEQ ID NO: 40 further comprise from 17 to 60 nucleotides, more preferred from 18 to 30 nucleotides, more preferred from 17 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In still a further embodiment, a molecule of the invention that is antisense to SEQ ID NO 4: 5'-CUGUUGAGAAA preferably comprises or consists of the antisense nucleotide sequence of SEQ ID NO 37 or SEQ ID NO 38. These preferred molecules of the invention comprising either SEQ ID NO: 37 or SEQ ID NO: 38 further comprise from 11 to 60 nucleotides, more preferred from 11 to 30 nucleotides, more preferred from 11 to 60, or preferably comprises or consists of 11, 12, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

A nucleotide sequence of a molecule of the invention may contain RNA residues, or one or more DNA residues, and/or one or more nucleotide analogues or equivalents, as will be further detailed herein below.

It is preferred that a molecule of the invention comprises one or more residues that are modified to increase nuclease resistance, and/or to increase the affinity of the antisense nucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred antisense oligonucleotide according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

A most preferred antisense oligonucleotide according to the invention comprises a 2'-O-methyl phosphorothioate ribose.

It will also be understood by a skilled person that different antisense oligonucleotides can be combined for efficiently skipping of exon 44. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably myogenic cells or muscle cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

A preferred antisense oligonucleotide comprises a peptide-linked PMO.

An oligonucleotide of the invention may be indirectly administrated using suitable means known in the art. An oligonucleotide may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of a molecule as identified herein. A cell can be provided with a molecule capable of interfering with essential sequences that result in highly efficient skipping of exon 44 by plasmid-derived antisense oligonucleotide expression or viral expression provided by adenovirus- or adeno-associated virus-based vectors. Expression is preferably driven by a polymerase III promoter, such as a U1, a U6, or a U7 RNA promoter. A preferred delivery vehicle is a viral vector such as an adeno-associated virus vector (AAV), or a retroviral vector such as a lentivirus vector (Goyenvalle A, et al. Rescue of dystrophic muscle through U7 snRNA-mediated exon skipping. Science 2004; 306(5702):1796-9, De Angelis F G, et al. Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61 or Denti M A, et al. Chimeric adeno-associated virus/antisense U1 small nuclear RNA effectively rescues dystrophin synthesis and muscle function by local treatment of mdx mice. Hum Gene Ther 2006; 17(5):565-74) and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript (see the same Goyenvalle A et al, De Angelis F G et al or Denti M A et al). Such fusions may be generated as described (Gorman L, et al, Stable alteration of pre-mRNA splicing patterns by modified U7 small nuclear RNAs. Proc Natl Acad Sci USA 1998; 95(9):4929-34 or Suter D, et al, Double-target antisense U7 snRNAs promote efficient skipping of an aberrant exon in three human beta-thalassemic mutations. Hum Mol Genet 1999; 8(13):2415-23). The oligonucleotide may be delivered as is. However, the oligonucleotide may also be encoded by the viral vector. Typically, this is in the form of an RNA transcript that comprises the sequence of the oligonucleotide in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of exon 44 of DMD.

A preferred AAV-based vector comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of exon 44 of the DMD gene.

Improvements in means for providing an individual or a cell, tissue, organ of said individual with an oligonucleotide and/or an equivalent thereof, are anticipated considering the progress that has already thus far been achieved. Such future improvements may of course be incorporated to achieve the mentioned effect on restructuring of mRNA using a method of the invention. An oligonucleotide and/or an equivalent thereof can be delivered as is to an individual, a cell, tissue or organ of said individual. When administering an oligonucleotide and/or an equivalent thereof, it is preferred that an oligonucleotide and/or an equivalent thereof is dissolved in a solution that is compatible with the delivery method. Muscle or myogenic cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a muscle cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constitutent as defined herein to a cell, preferably a muscle cell. Such excipients have been shown to efficiently deliver an oligonucleotide such as antisense nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an oligonucleotide for use in the current invention to deliver it for the treatment of Duchenne Muscular Dystrophy or Becker Muscular Dystrophy in humans.

In addition, an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an oligonucleotide is formulated in a composition or a medicament or a composition, which is provided with at least an excipient and/or a targeting ligand for delivery and/or a delivery device thereof to a cell and/or enhancing its intracellular delivery. Accordingly, the invention also encompasses a pharmaceutically acceptable composition comprising an oligonucleotide and further comprising at least one excipient and/or a targeting ligand for delivery and/or a delivery device of said oligonucleotide to a cell and/or enhancing its intracellular delivery. It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an oligonucleotide and a further adjunct compound as later defined herein.

A preferred oligonucleotide is for preventing or treating Duchenne Muscular Dystrophy (DMD) or Becker Muscular Dystrophy (BMD) in an individual. An individual, which may be treated using an oligonucleotide of the invention may already have been diagnosed as having a DMD or a BMD. Alternatively, an individual which may be treated using an oligonucleotide of the invention may not have yet been diagnosed as having a DMD or a BMD but may be an individual having an increased risk of developing a DMD or a BMD in the future given his or her genetic background. A preferred individual is a human being.

If required, a molecule or a vector expressing an antisense oligonucleotide of the invention can be incorporated into a pharmaceutically active mixture by adding a pharmaceutically acceptable carrier.

Therefore, the invention also provides a pharmaceutical composition comprising a molecule comprising an antisense oligonucleotide according to the invention, or a viral-based vector expressing the antisense oligonucleotide according to the invention.

In a further aspect, there is provided a composition comprising an oligonucleotide as defined herein. Preferably, said composition comprises at least two distinct oligonucleotides as defined herein. More preferably, these two distinct oligonucleotides are designed to skip one or two or more exons. Multi-skipping is encompassed by the present invention, wherein an oligonucleotide of the invention inducing the skipping of exon 44 is used in combination with another oligonucleotide inducing the skipping of another exon. In this context, another exon may be exon 43, 45 or 52. Multi exon skipping has been already disclosed in EP 1 619 249. The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.4 Mb. Defects may occur in any part of the DMD gene. Skipping of a particular exon or particular exons can, very often, result in a restructured mRNA that encodes a shorter than normal but at least partially functional dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations, requires the generation of a series of different pharmaceuticals as for different mutations different exons need to be skipped. An advantage of an oligonucleotide or of a composition comprising at least two distinct oligonucleotide as later defined herein capable of inducing skipping of two or more exons, is that more than one exon can be skipped with a single pharmaceutical. This property is not only practically very useful in that only a limited number of pharmaceuticals need to be generated for treating many different DMD or particular, severe BMD mutations. Another option now open to the person skilled in the art is to select particularly functional restructured dystrophin proteins and produce compounds capable of generating these preferred dystrophin proteins. Such preferred end results are further referred to as mild phenotype dystrophins.

In a preferred embodiment, said composition being preferably a pharmaceutical composition said pharmaceutical composition comprising a pharmaceutically acceptable carrier, adjuvant, diluent and/or excipient. Such a pharmaceutical composition may comprise any pharmaceutically acceptable carrier, filler, preservative, adjuvant, solubilizer, diluent and/or excipient is also provided. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000. Each feature of said composition has earlier been defined herein.

If several oligonucleotides are used, concentration or dose already defined herein may refer to the total concentration or dose of all oligonucleotides used or the concentration or dose of each oligonucleotide used or added. Therefore in one embodiment, there is provided a composition wherein each or the total amount of oligonucleotide used is dosed in an amount ranged between 0.5 mg/kg and 10 mg/kg.

The invention further provides the use of an antisense oligonucleotide according to the invention, or a viral-based vector that expresses an antisense oligonucleotide according to the invention, for modulating splicing of the DMD mRNA. The splicing is preferably modulated in human myogenic cells or muscle cells in vitro. More preferred is that splicing is modulated in human myogenic cells or muscle cells in vivo.

A preferred antisense oligonucleotide comprising one or more nucleotide analogs or equivalents of the invention modulates splicing in one or more muscle cells, including heart muscle cells, upon systemic delivery. In this respect, systemic delivery of an antisense oligonucleotide comprising a specific nucleotide analog or equivalent might result in targeting a subset of muscle cells, while an antisense oligonucleotide comprising a distinct nucleotide analog or equivalent might result in targeting of a different subset of muscle cells. Therefore, in one embodiment it is preferred to use a combination of antisense oligonucleotides comprising different nucleotide analogs or equivalents for modulating skipping of exon 44 of the DMD mRNA.

The invention furthermore provides the use of an antisense oligonucleotide according to the invention, or of a viral-based vector expressing the antisense oligonucleotide according to the invention, for the preparation of a medicament for the treatment of a DMD or BMD patient.

Therefore in a further aspect, there is provided the use of a oligoucleotide or of a composition as defined herein for the manufacture of a medicament for preventing or treating Duchenne Muscular Dystrophy or Becker Muscular Dystrophy in an individual. Each feature of said use has earlier been defined herein.

A treatment in a use or in a method according to the invention is at least one week, at least one month, at least several months, at least one year, at least 2, 3, 4, 5, 6 years or more. Each molecule or oligonucleotide or equivalent thereof as defined herein for use according to the invention may be suitable for direct administration to a cell, tissue and/or an organ in vivo of individuals affected by or at risk of developing DMD or BMD, and may be administered directly in vivo, ex vivo or in vitro. The frequency of administration of an oligonucleotide, composition, compound or adjunct compound of the invention may depend on several parameters such as the age of the patient, the mutation of the patient, the number of molecules (i.e. dose), the formulation of said molecule. The frequency may be ranged between at least once in two weeks, or three weeks or four weeks or five weeks or a longer time period.

Dose ranges of oligonucleotide according to the invention are preferably designed on the basis of rising dose studies in clinical trials (in vivo use) for which rigorous protocol requirements exist. A molecule or an oligonucleotide as defined herein may be used at a dose which is ranged between 0.1 and 20 mg/kg, preferably 0.5 and 10 mg/kg.

In a preferred embodiment, a concentration of an oligonucleotide as defined herein, which is ranged between 0.1 nM and 1 μM is used. Preferably, this range is for in vitro use in a cellular model such as muscular cells or muscular tissue. More preferably, the concentration used is ranged between 0.3 to 400 nM, even more preferably between 1 to 200 nM. If several oligonucleotides are used, this concentration or dose may refer to the total concentration or dose of oligonucleotides or the concentration or dose of each oligonucleotide added. The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimised any further.

An oligonucleotide as defined herein for use according to the invention may be suitable for administration to a cell, tissue and/or an organ in vivo of individuals affected by or at risk of developing DMD or BMD, and may be administered in vivo, ex vivo or in vitro. Said oligonucleotide may be directly or indirectly administered to a cell, tissue and/or an organ in vivo of an individual affected by or at risk of developing DMD or BMD, and may be administered directly or indirectly in vivo, ex vivo or in vitro. As Duchenne and Becker muscular dystrophy have a pronounced phenotype in muscle cells, it is preferred that said cells are muscle cells, it is further preferred that said tissue is a muscular tissue and/or it is further preferred that said organ comprises or consists of a muscular tissue. A preferred organ is the heart. Preferably, said cells comprise a gene encoding a mutant dystrophin protein. Preferably, said cells are cells of an individual suffering from DMD or BMD.

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

The expression "in vivo" as used herein may mean in a cellular system which may be isolated from the organism the cells derive from. Preferred cells are muscle cells. In vivo may also mean in a tissue or in a multicellular organism which is preferably a patient as defined herein. Through out the invention, in vivo is opposed to in vitro which is generally associated with a cell free system.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

(A) In differentiated muscle cells (myotubes) from a patient with an exon 45 deletion, all tested (transfected) AONs induced exon 44 skipping at a concentration of 150 nM, with PS188 (SEQ ID NO:5), PS190 (previously published as h44AON2; Aartsma-Rus et al. Neuromuscul Disord 2002; 12 Suppl: S71), PS191 (SEQ ID NO: 39), PS193 (SEQ ID NO: 40), PS194 (SEQ ID NO: 38), and PS196 (SEQ ID NO: 43) demonstrating highest efficiencies (between 84% and 94%).

(B) The majority of AONs was also tested by transfection into healthy human control cells at 150 and 400 nM concentrations. The results are summarized in this column chart. PS188 (SEQ ID NO:5), PS190, PS191 (SEQ ID NO: 39), PS193 (SEQ ID NO: 40), PS194 (SEQ ID NO: 38), and PS196 (SEQ ID NO: 43) were confirmed to be most efficient in inducing exon 44 skipping. Note that the exon 44 skipping levels in patient cells are typically higher than in control cells as a result of the fact that, in contrast to healthy cells, in patient cells exon 44 skipping is frame-restoring and giving rise to a more functional and stable. No exon 44 skipping was observed in non-transfected muscle cells in all experiments (data not shown).

(C) Examples of PS197 (SEQ ID NO 44) and three additional AONs, PS199 (SEQ ID NO 36), PS200 (SEQ ID NO 41), and PS201 (SEQ ID NO 42), similarly tested in control muscle cells, at transfection concentrations 150 nM and 400 nM. The exon 44 skipping percentages varied between 1% (PS199) and 44% (PS200). M: DNA size marker (100 bp ladder).

Figure 2A:
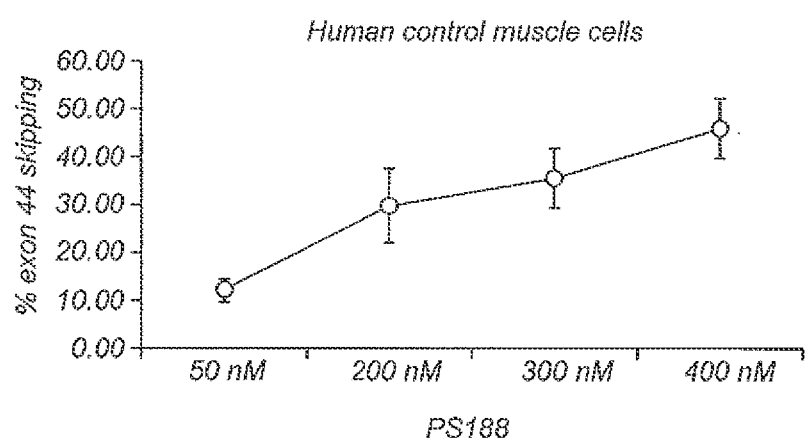
Figure 2B:
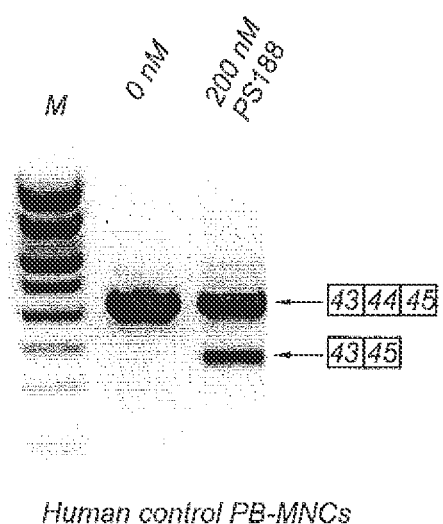

FIGS. 2A-2B. Further evaluation of PS188 (SEQ ID NO:5) by transfection of human control muscle cells or peripheral blood mononuclear cells (PB-MNCs).

(A) Dose-response experiment. In human control muscle cells, PS188 showed increasing levels of exon 44 skipping at transfection doses increasing from 50 nM to 400 nM {in triplo), up to 45% at 400 nM.

(B) PB-MNCs of a healthy individual were transfected with 200 nM PS188. Despite the fact that dystrophin is only expressed at low levels in this type of cells, exon 44 skipping was clearly observed. These results confirm the efficiency of PS188 in inducing exon 44 skipping from the DMD gene. M: DNA size marker.

Figure 3A:
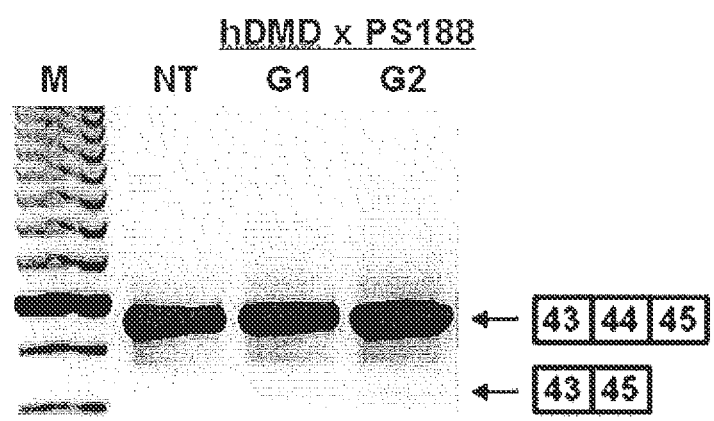
Figure 3B:
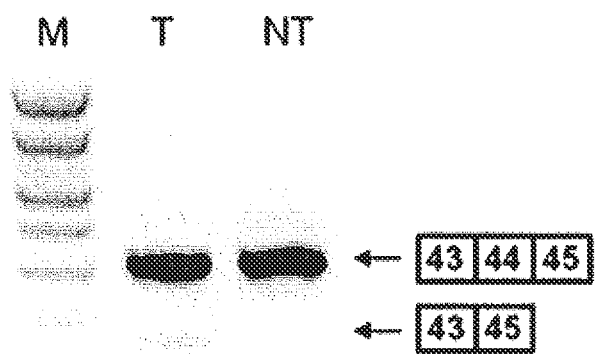

FIGS. 3A-3B. Further evaluation of PS188 (SEQ ID NO:5) by administration to transgenic hDMD mice expressing the full length human DMD gene, and to cynomolgus monkeys included in extensive toxicity studies.

(A) Following intramuscular injection of 2×40|ig PS188 into both gastrocnemius muscles (G1 and G2) of an hDMD mouse, exon 44 skipping was observed, albeit at low levels. This confirms the capacity of PS188 to induce human exon 44 skipping in muscle tissue in vivo. The low levels were expected given the fact that this mouse model has healthy muscle fibers typically showing lower levels of AON uptake when compared to dystrophic muscle fibers. NT: in non-treated hDMD muscle no exon 44 skipping was observed. M: DNA size marker (B) In monkeys included in toxicity studies on PS188, exon 44 skipping was observed in peripheral blood mononuclear cells (PB-MNCs) after 1-hour intravenous infusions every fourth day for 29 days at a dose-level of 6 mg/kg PS188. No exon 44 skipping was observed in non-treated monkeys (NT). M: DNA size marker.

EXAMPLES

Example 1

Material and Methods

AON design was based on (partly) overlapping open secondary structures of the target exon RNA as predicted by the m-fold program (Mathews et al., J Mol Biol 1999; 288(5): 911-40), on (partly) overlapping putative SR-protein binding sites as predicted by the ESE-finder software (rulai.cshl.edu/tools/ESE/) (Cartegni et al., Nucleic Acids Res 2003; 31(13): 3568-71), and on avoiding G-stretches of 3 or more nucleotides or CpG pairs. AONs (see Table 1) were synthesized by Eurogentec (Belgium) and Prosensa Therapeutics BV (Leiden, Netherlands), and contain 2'-O-methyl RNA and full-length phosphorothioate backbones.

Tissue Culturing, Transfection and RT-PCR Analysis

Myotube cultures derived from a healthy individual ("human control") or a DMD patient with an exon 45 deletion were processed as described previously (Aartsma-Rus et al. Hum Mol Genet 2003; 12(8): 907-14; Havenga et al. J Virol 2002; 76(9): 4612-20). For the screening of AONs, myotube cultures were transfected with 150 and/or 400 nM of each AON. Transfection reagent polyethylenimine (PEI, ExGen500 MBI Fermentas) or a derivative (UNIFectylin, Prosensa Therapeutics BV, Netherlands) was used, with 2 µl ExGen500 or UNIFectylin per µg AON. A control AON with a fluorescein label was used to confirm optimal transfection efficiencies (typically over 90% fluorescent nuclei were obtained). RNA was isolated 24 to 48 hours after transfection as described (Aartsma-Rus et al. Neuromuscul Disord 2002; 12 Suppl: S71). Exon skipping efficiencies were determined by nested RT-PCR analysis using primers in the exons flanking exon 44 (Aartsma-Rus et al. Neuromuscul Disord 2002; 12 Suppl: S71). PCR fragments were isolated from agarose gels (using the QIAquick Gel Extraction Kit (QIAGEN) for sequence verification (by the Leiden Genome Technology Center (LGTC) using the BigDye Terminator Cycle Sequencing Ready Reaction kit (PE Applied Biosystems), and ABI 3700 Sequencer (PE Applied Biosystems). For quantification, the PCR products were analyzed using the DNA 1000 LabChips Kit on the Agilent 2100 bioanalyzer (Agilent Technologies, USA).

Results

Figure 1A:
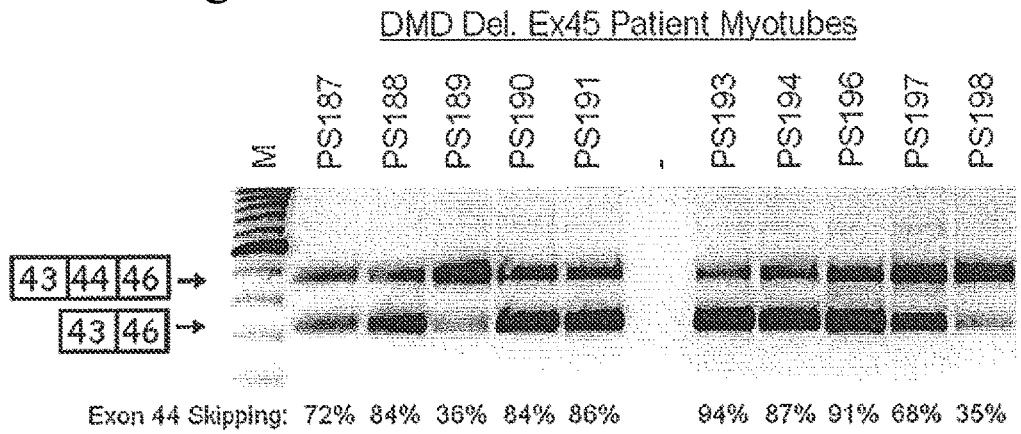
FIGS. 1A-1C. Evaluation of AONs designed to induce the skipping of exon 44 from the DMD gene in transfected muscle cells from healthy control or a DMD patient with an exon 45 deletion.

A series of AONs targeting sequences within exon 44 were designed and tested both in healthy control and patient-derived myotube cultures, by transfection and subsequent RT-PCR and sequence analysis of isolated RNA. In myotubes derived from a DMD patient with a deletion of exon 45, specific exon 44 skipping was induced at 150 nM for every AON (PS187 to PS201) tested, with PS188 (SEQ ID NO:5), PS190 (previously published as h44AON2, Aartsma-Rus et al. Neuromuscul Disord 2002; 12 Suppl: S71), PS191 (SEQ ID NO: 39), PS193 (SEQ ID NO: 40), PS194 (SEQ ID NO: 38), and PS196 (SEQ ID NO: 43) demonstrating highest levels of skipping (between 84% and 94% at 150 nM) (FIG. 1A).

Figure 1B:
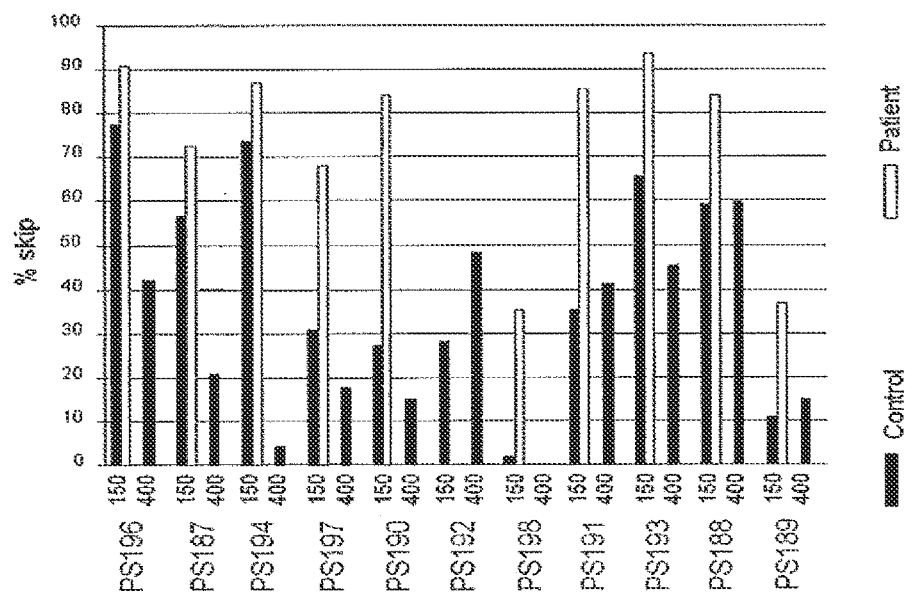

Similar transfection experiments were done in control cells from a healthy individual. Percentages of exon 44 skipping were assessed and compared to those in the patient cell cultures (FIG. 1B). Inherent to nonsense-mediated RNA decay of the control transcript after exon 44 skipping, the control percentages were typically lower than those in the patient cells (see for instance results with PS197 in FIG. 1A (patient cells) vs FIG. 1C (control cells)).

Figure 1C:
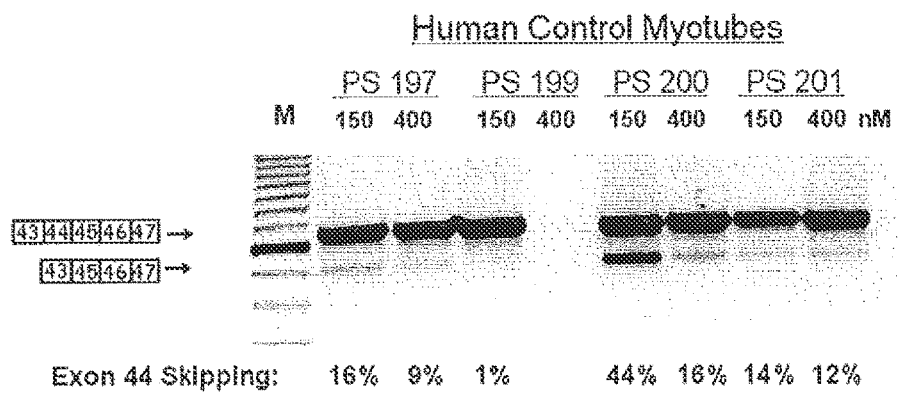

Three additional AONs (PS199 (SEQ ID NO 36), PS200 (SEQ ID NO 41), and PS201 (SEQ ID NO. 42) were tested in control muscle cells, at concentrations of 150 nM and 400 nM. The exon 44 skipping percentages varied between 1% (PS199) and 44% (PS200) (FIG. 1C). Based on all transfection experiments, the AONs PS187, PS188, PS190, PS191, PS192, PS193, PS194, PS196 and PS200 were considered most efficient, and AONs PS189, PS197, PS198, PS199, and PS201 least efficient.

PS188 (SEQ ID NO 5) was further tested in dose-response experiments in healthy human control muscle cells, applying increasing doses from 50 to 400 nM in triplo. Increasing levels of exon 44 skipping were accordingly observed, up to 45% at 400 nMPS188 (FIG. 2A).

Example 2

Materials and Methods

A fresh healthy human control blood sample, collected in an EDTA tube, was layered on top of a HistoPaque gradient. Upon centrifugation, the second layer (of the four layers, from top to bottom) with the mononuclear cells was collected, washed, and centrifuged again. The cell pellet was resuspended in proliferation culturing medium and counted. In a 6-wells plate, $8 \times 10^6$ cells per well were plated and incubated at 37° C., 5% $CO_2$ for 3 hrs. The cells were then transfected with 0 or 200 nM PS188 (SEQ ID NO:5; 2'OMePS RNA; Prosensa Therapeutics BV), in duplo, per dish. RNA was isolated 72 hrs after transfection, and analysed by RT-PCR analysis using DMD-gene specific primers flanking exon 44 (Aartsma-Rus et al. Neuromuscul Disord 2002; 12 Suppl: S71). Sequence analysis (by the Leiden Genome Technology Center (LGTC) using the BigDye Terminator Cycle Sequencing Ready Reaction kit (PE Applied Biosystems), and ABI 3700 Sequencer (PE Applied Biosystems) was performed on isolated PCR products (using the QIAquick Gel Extraction Kit (QIAGEN) to confirm the specific exon 44 skipping on RNA level.

Results

In transfected peripheral blood mononuclear cells (PB-MNCs) from a healthy control individual, PS188 induced the production of a novel shorter transcript fragment when applied at 200 nM (FIG. 2B). This fragment was isolated an sequenced and confirmed due to the specific skipping of exon 44. In non-transfected PB-MNCs no exon 44 skipping was observed. These results indicate that PS188 is an efficient compound inducing human exon 44 skipping in vitro.

Example 3

Materials and Methods

Antisense Oligoribonucleotides (AONs).

Normal and mdx mice (Sicinski et al. (1989). Science 244: 1578-1580) were injected with the mouse-specific m46AON4 (van Deutekom et al. (2001) Hum Mol Genet 10: 1547-1554), whereas the hDMD mice with the human-specific PS196 (SEQ ID NO 43) or PS188 (SEQ ID NO 5). Both AONs contained a full-length phosphorothioate backbone and 2'-0-methyl modified ribose molecules (PS196: Eurogentec, Belgium; PS188: Prosensa Therapeutics BV).

Normal, Mdx and Transgenic hDMD Mice

Normal mice (C57Bl/6NCrL) and mdx mice (C57Bl/10ScSn-mthdJ) were obtained from Charles River Laboratories (The Netherlands). Transgenic hDMD mice were engineered in our own LUMC laboratories. Briefly, embryonic stem (ES) cells were genetically modified through fusions with yeast spheroplasts carrying a YAC of 2.7 Mb that contained the full-length (2.4 Mb) human DMD gene. This YAC was previously reconstructed by homologous recombination of smaller overlapping YACs in yeast (Den Dunnen et al. (1992). Hum Mol Genet 1: 19-28). ES-cells showing integration of one copy of the full-size YAC, as assessed by PFGE mapping, exon-PCR analysis across the entire gene, and metaphase FISH analysis, were then used to generate homozygous hDMD mice ('t Hoen et al., J. Biol. Chem. 2008). Transgenic hDMD mice do not appear to be physically affected by the genetic modification. Appropriate expression of the human DMD gene could be demonstrated in muscle, both at RNA and protein level. The engineering of these mice was authorised by the Dutch Ministry of Agriculture (LNV); project nr. VVA/BD01.284 (E21).

Administration of AONs.

The experiments on intramuscular AON-injections in mice were authorised by the animal experimental commission (UDEC) of the Medical Faculty of the Leiden University (project no. 00095, 03027). AONs were injected, either pure, or complexed to the cationic polymer polyethylenimine (PEI; ExGen 500 (20×), MBI Fermentas) at ratios of 1 ml PEI per nmol AON in a 5% w/v glucose solution, or to 15 nmol SAINT-18TM (Synvolux Therapeutics B.V., The Netherlands), according to the manufacturers' instructions. The SAINT-18TM delivery system is based on a cationic pyridinium head group and allows non-toxic delivery of antisense oligonucleotides. Mice were anaesthetised by intraperitoneal injection of a 1:1 (v/v) Hypnorm/Dormicum solution (Janssen Pharmaceutica, Belgium/Roche, The Netherlands). Pure AON (PS188) was administered in a final injection volume of 40 µl by intramuscular injection into both gastrocnemius muscles of the mice using a Hamilton syringe with a 22-Gauge needle. The mice received two injections of 40 µg at a 24 h interval. They were sacrificed at different time-points post-injection; for PS188-injected hDMD mice ten days after the last injection. Muscles were isolated and frozen in liquid nitrogen-cooled 2-methylbutane.

RT-PCR Analysis.

Muscle samples were homogenized in RNA-Bee solution (Campro Scientific, The Netherlands). Total RNA was isolated and purified according to the manufacturer's instructions. For cDNA synthesis with the reverse transcriptase C. therm polymerase or Transcriptor (Roche Diagnostics, The Netherlands), 300 ng of RNA was used in a 20·1 reaction at 60° C. for 30 min, reverse primed with either mouse- or human-specific primers. First PCRs were performed with outer primer sets (flanking exons 43-45 for PS188-injected mice), for 20 cycles of 94° C. (40 sec), 60° C. (40 sec), and 72° C. (60 sec). One µl of this reaction (diluted 1:10) was then re-amplified using nested primer combinations in the exons directly flanking the target exon (exon 44 for PS188-injected mice), with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). Primer sets and sequences were described previously (Aartsma-Rus et al. (2002) Neuromuscul Disord 12 Suppl: S71.8, 17; van Deutekom et al. (2001) Hum Mol Genet 10: 1547-1554).

Sequence Analysis.

RT-PCR products were isolated from 2% agarose gels using the QIAquick Gel Extraction Kit (QIAGEN). Direct DNA sequencing was carried out by the Leiden Genome Technology Center (LGTC) using the BigDye Terminator Cycle Sequencing Ready Reaction kit (PE Applied Biosystems), and analyzed on an ABI 3700 Sequencer (PE Applied Biosystems).

MALDI-TOF Mass-Spectrometry.

RNA-Bee muscle homogenates were purified using a nucleic acid purification kit (Nucleic Acid Purification Kit for Sequazyme™ Pinpoint SNP Kit, Applied Biosystems) with 96 well spin plates (Applied Biosystems) following the manufacturer's instructions. Matrix solution (50 mg/ml 3-hydroxy picolinic acid and 25 mM dibasic ammonium citrate in 50% acetonitrile) was applied in 1 ml aliquots to an AnchorChip™ sample target (Bruker Daltonics, Germany) and air-dried. Samples were spotted in 0.5 ml aliquots onto the matrix crystals and air-dried. Mass determinations were performed on a Reflex III MALDI-TOF mass-spectrometer (Bruker Daltonics, Germany). Spectra were acquired in reflector mode and accumulated for approximately 900 laser shots. Samples of labelled and unlabelled m46AON4 were analyzed for comparison.

Results

Exon Skipping in Wild-Type Muscle

We first set up targeted exon skipping in mouse muscle in vivo and optimised different parameters of administration. Initial experiments were performed in wild type mice, and, while nonsense-mediated RNA decay will cause underestimation of the exon skipping efficiencies, the effect of the AONs was monitored on mRNA level only. We injected increasing dosages from 0.9 nmol to 5.4 nmol of each antisense oligonucleotide. RT-PCR analysis of total muscle RNA demonstrated the occurrence of a novel shorter transcript fragment in all samples injected. Sequence analysis confirmed the precise skipping of exon 44 in this product (data not shown).

Cross-sections of the contra-lateral injected muscles were analysed for dispersion and persistence of a fluorescein-labelled control AON. Following injection of pure AON, we observed fluorescent signals within some fibres for up to one week. At later time points only weak signals were observed, and mainly within the interstitial spaces. The use of PEI clearly enhanced both dispersion and persistence of the fluorescent signal, even after 3 weeks. However, it also induced fibre degeneration and monocyte infiltration absorbing most fluorescence. Using SAINT, most of the signal was detected in the interstitial spaces for up to one week, indicating that this reagent did not efficiently deliver the AON into the muscle fibres. Since the fluorescent signal may not correspond to the presence of intact and functional AONs, we performed MALDI-TOF mass-spectrometry of injected muscle samples. The analyses indicated that the fluorescent label was removed from the AON within 24 hours. The labelled AON was only detectable for up to two weeks when using PEI. The interstitial AONs were probably more vulnerable to degradation than the intracellular AONs. The unlabelled AON was observed for three to four weeks post-injection in all three series, but it may only be functional when present intracellularly, i.e. in the PEI series.

Human-Specific Exon Skipping in hDMD Muscle

Since the exon skipping strategy is a sequence-specific therapeutic approach, the ideal pre-clinical validation would be a target human DMD gene, in a mouse experimental background. We have engineered such transgenic, "humanised" DMD (hDMD) mice carrying an integrated and functional copy of the full-length human DMD gene. Expression of human dystrophin in hDMD mouse muscle was specifically detected by immunohistochemical analysis of cross-sections, using a human-specific antibody (MANDYS106). On muscle RNA level, RT-PCR analyses using either mouse- or human-specific primers demonstrated correct transcription of the human DMD gene. Furthermore, upon crossing with mdx mice, the hDMD construct showed to complement the dystrophic defect, as was assessed by histological and cDNA microarray analysis ('t Hoen et al., J. Biol. Chem. 2008). hDMD mice have healthy muscle fibers typically exhibiting a limited uptake of naked AONs. We injected the human-specific AON PS196 (SEQ ID NO 43) complexed to PEI, or PS188 (SEQ ID NO 5) without PEI, into the gastrocnemius muscles of the hDMD mice (2×40 µg injections within 24 hrs). At 7 to 10 days post-injection we clearly observed the skipping of the targeted exon 44 from the human DMD transcript (FIG. 3A). Although the human-specific AONs are highly homologous to the corresponding mouse sequences, with only 2 or 3 mismatches in the respective 20-mers, the mouse endogenous transcripts were not affected to any detectable level. PS188 induced exon 44 skipping, as confirmed by sequence analysis. No exon 44 skipping was observed in non-treated hDMD muscle. These results indicate that PS188 is an efficient compound inducing human exon 44 skipping in muscle tissue.

Example 4

Material and Methods

As part of an extensive toxicity program for PS188, non-fasted cynomolgus monkeys were treated by 1-hour intravenous infusion (5 mL/kg/h) every fourth day for 29 days at the dose-level of 6 mg/kg PS188 (SEQ ID NO 5; 2'OMePS RNA; Agilent Life Sciences, USA). The PS188 formulations were freshly prepared on each treatment day (on test days 1, 5, 9, 13, 17, 21, 25 and 29) shortly before initiation of the administration (as soon as possible before, at the most within one hour before start of administration). Formulations were prepared by dissolving PS188 in phosphate buffer; the purity and water content were taken into account as provided in the Certificate of Analysis of the drug substance. The amount of PS188 was adjusted to each animal's current body weight. The animals were sacrificed 96 hours after the last administration (day 33). Whole blood samples (10 ml) were collected in EDTA tubes, and (after overnight shipment at room temperature) layered on top of a HistoPaque gradient. Upon centrifugation, the second layer (of the four layers, from top to bottom) with the mononuclear cells was collected, washed, and centrifuged again. RNA was isolated from the resulting cell pellet and analysed by RT-PCR analysis using DMD-gene specific primers flanking exon 44 (Aartsma-Rus et al. Neuromuscul Disord 2002; 12 Suppl: S71). Sequence analysis (by the Leiden Genome Technology Center (LGTC) using the Big-Dye Terminator Cycle Sequencing Ready Reaction kit (PE Applied Biosystems), and ABI 3700 Sequencer (PE Applied Biosystems) was performed on isolated PCR products (using the QIAquick Gel Extraction Kit (QIAGEN) to confirm the specific exon 44 skipping on RNA level.

Results

In monkeys treated by 1-hour intravenous infusions every fourth day for 29 days at the dose-level of 6 mg/kg PS188, exon 44 skipping was observed in peripheral blood mononuclear cells (FIG. 3B), despite the fact that these cells express only low levels of dystrophin. The human and monkey DMD sequence targeted by PS188 is in fact 100% identical. No exon 44 skipping was observed in non-treated monkeys. These results indicate that PS188 is an efficient compound inducing exon 44 skipping in vivo.

TABLE 1A

Table 1 Antisense oligonucleotide sequences.

| # | Sequence | SEQ ID |
|---|---|---|
| 1 (PS188) | UCAGCUUCUGUUAGCCACUG | SEQ ID NO 5 |
| 2 | UUCAGCUUCUGUUAGCCACU | SEQ ID NO 6 |
| 3 | UUCAGCUUCUGUUAGCCACUG | SEQ ID NO 7 |
| 4 | UCAGCUUCUGUUAGCCACUGA | SEQ ID NO 8 |
| 5 | UUCAGCUUCUGUUAGCCACUGA | SEQ ID NO 9 |
| 6 | UCAGCUUCUGUUAGCCACUGAU | SEQ ID NO 10 |
| 7 | UUCAGCUUCUGUUAGCCACUGAU | SEQ ID NO 11 |
| 8 | UCAGCUUCUGUUAGCCACUGAUU | SEQ ID NO 12 |
| 9 | UUCAGCUUCUGUUAGCCACUGAUU | SEQ ID NO 13 |
| 10 | UCAGCUUCUGUUAGCCACUGAUUA | SEQ ID NO 14 |
| 11 | UUCAGCUUCUGUUAGCCACUGAUA | SEQ ID NO 15 |
| 12 | UCAGCUUCUGUUAGCCACUGAUUAA | SEQ ID NO 16 |
| 13 | UUCAGCUUCUGUUAGCCACUGAUUAA | SEQ ID NO 17 |
| 14 | UCAGCUUCUGUUAGCCACUGAUUAAA | SEQ ID NO 18 |
| 15 | UUCAGCUUCUGUUAGCCACUGAUUAAA | SEQ ID NO 19 |
| 16 | CAGCUUCUGUUAGCCACUG | SEQ ID NO 20 |
| 17 | CAGCUUCUGUUAGCCACUGAU | SEQ ID NO 21 |
| 18 | AGCUUCUGUUAGCCACUGAUU | SEQ ID NO 22 |
| 19 | CAGCUUCUGUUAGCCACUGAUU | SEQ ID NO 23 |
| 20 | AGCUUCUGUUAGCCACUGAUUA | SEQ ID NO 24 |
| 21 | CAGCUUCUGUUAGCCACUGAUUA | SEQ ID NO 25 |
| 22 | AGCUUCUGUUAGCCACUGAUUAA | SEQ ID NO 26 |
| 23 | CAGCUUCUGUUAGCCACUGAUUAA | SEQ ID NO 27 |
| 24 | AGCUUCUGUUAGCCACUGAUUAAA | SEQ ID NO 28 |
| 25 | CAGCUUCUGUUAGCCACUGAUUAAA | SEQ ID NO 29 |

TABLE 1A-continued

Table 1 Antisense oligonucleotide sequences.

| | | |
|---|---|---|
| 26 | AGCUUCUGUUAGCCACUGAU | SEQ ID NO 30 |
| 27 | GCUUCUGUUAGCCACUGAUU | SEQ ID NO 31 |
| 28 | GCUUCUGUUAGCCACUGAUUA | SEQ ID NO 32 |
| 29 | GCUUCUGUUAGCCACUGAUUAA | SEQ ID NO 33 |
| 30 | GCUUCUGUUAGCCACUGAUUAAA | SEQ ID NO 34 |
| 31 (PS 192) | CCAUUUGUAUUUAGCAUGUUCCC | SEQ ID NO 35 |
| 32 (PS 199) | AGAUACCAUUUGUAUUUAGC | SEQ ID NO 36 |
| 33 (PS 187) | GCCAUUUCUCAACAGAUCU | SEQ ID NO 37 |
| 34 (PS 194) | GCCAUUUCUCAACAGAUCUGUCA | SEQ ID NO 38 |
| 35 (PS191) | AUUCUCAGGAAUUUGUGUCUUUC | SEQ ID NO 39 |
| 36 (PS 193) | UCUCAGGAAUUUGUGUCUUUC | SEQ ID NO 40 |
| 37 (PS 200) | GUUCAGCUUCUGUUAGCC | SEQ ID NO 41 |
| 38 (PS 201) | CUGAUUAAAUAUCUUUAUAU C | SEQ ID NO 42 |

TABLE 1B

| | | |
|---|---|---|
| 39 (PS 196) | GCCGCCAUUUCUCAACAG | SEQ ID NO 43 |
| 40 (PS 197) | GUAUUUAGCAUGUUCCCA | SEQ ID NO 44 |
| 41 (PS 198) | CAGGAAUUUGUGUCUUUC | SEQ ID NO 45 |
| 42 (PS 189) | UCUGUUAGCCACUGAUUAAAU | SEQ ID NO 46 |

SEQ. ID NO: 47
MLWWEEVEDCYEREDVQKKTFTKWVNAQFSKFGKQHIENLFSDLQDGRR
LLDLLEGLTGQKLPKEKGSTRVHALNNVNKALRVLQNNNVDLVNIGSTD
IVDGNHKLTLGLIWNIILHWQVKNVMKNIMAGLQQTNSEKILLSWVRQS
TRNYPQVNVINFTTSWSDGLALNALIHSHRPDLFDWNSVVCQQSATQRL
EHAFNIARYQLGIEKLLDPEDVDTTYPDKKSILMYITSLFQVLPQQVSI
EAIQEVEMLPRPPKVTKEEHFQLHHQMHYSQQITVSLAQGYERTSSPKP
RFKSYAYTQAAYVTTSDPTRSPFPSQHLEAPEDKSFGSSLMESEVNLDR
YQTALEEVLSWLLSAEDTLQAQGEISNDVEVVKDQFHTHEGYMMDLTAH
QGRVGNILQLGSKLIGTGKLSEDEETEVQEQMNLLNSRWECLRVASMEK
QSNLHRVLMDLQNQKLKELNDWLTKTEERTRKMEEEPLGPDLEDLKRQV
QQHKVLQEDLEQEQVRVNSLTHMVVVVDESSGDHATAALEEQLKVLGDR
WANICRWTEDRWVLLQDILLKWQRLTEEQCLFSAWLSEKEDAVNKIHTT
GFKDQNEMLSSLQKLAVLKADLEKKKQSMGKLYSLKQDLLSTLKNKSVT
QKTEAWLDNFARCWDNLVQKLEKSTAQISQAVTTTQPSLTQTTVMETVT
TVTTTREQILVKHAQEELPPPPPQKKRQITVDSEIRKRLDVDITELHSWI
TRSEAVLQSPEFAIFRKEGNFSDLKEKVNAIEREKAEKFRKLQDASRSA
QALVEQMVNEGVNADSIKQASEQLNSRWIEFCQLLSERLNWLEYQNNII
AFYNQLQQLEQMTTTAENWLKIQPTTPSEPTAIKSQLKICKDEVNRLSG

-continued
LQPQIERLKIQSIALKEKGQGPMFLDADFVAFTNHFKQVFSDVQAREKE
LQTIFDTLPPMRYQETMSAIRTWVQQSETKLSIPQLSVTDYEIMEQRLG
ELQALQSSLQEQQSGLYYLSTTVKEMSKKAPSEISRKYQSEFEEIEGRW
KKLSSQLVEHCQKLEEQMNKLRKIQNHIQTLKKWMAEVDVFLKEEWPAL
GDSEILKKQLKQCRLLVSDIQTIQPSLNSVNEGGQKIKNEAEPEFASRL
ETELKELNTQWDHMCQQVYARKEALKGGLEKTVSLQKDLSEMHEWMTQA
EEEYLERDFEYKTPDELQKAVEEMKRAKEEAQQKEAKVKLLTESVNSVI
AQAPPVAQEALKKELETLTTNYQWLCTRLNGKCKTLEEVWACWHELLSY
LEKANKWLNEVEFKLKTTENIPGGAEEISEVLDSLENLMRHSEDNPNQI
RILAQTLTDGGVMDELINEELETFNSRWRELHEEAVRRQKLLEQSIQSA
QETEKSLHLIQESLTFIDKQLAAYIADKVDAAQMPQEAQKIQSDLTSHE
ISLEEMKKHNQGKEAAQRVLSQIDVAQKKLQDVSMKFRLFQKPANFEQR
LQESKMILDEVKMHLPALETKSVEQEVVQSQLNHCVNLYKSLSEVKSEV
EMVIKTGRQIVQKKQTENPKELDERVTALKLHYNELGAKVTERKQQLEK
CLKLSRKMRKEMNVLTEWLAATDMELTKRSAVEGMPSNLDSEVAWGKAT
QKEIEKQKVHLKSITEVGEALKTVLGKKETLVEDKLSLLNSNWIAVTSR
AEEWLNLLLEYQKHMETFDQNVDHITKWIIQADTLLDESEKKKPQQKED
VLKRLKAELNDIRPKVDSTRDQAANLMANRGDHCRKLVEPQISELNHRF
AAISHRIKTGKASIPLKELEQFNSDIQKLLEPLEAEIQQGVNLKEEDFN
KDMNEDNEGTVKELLQRGDNLQQRITDERKREEIKIKQQLLQTKHNALK
DLRSQRRKKALEISHQWYQYKRQADDLLKCLDDIEKKLASLPEPRDERK
IKEIDRELQKKKEELNAVRRQAEGLSEDGAAMAVEPTQIQLSKRWREIE
SKFAQFRRLNFAQIHTVREETMMVMTEDMPLEISYVPSTYLTEITHVSQ
ALLEVEQLLNAPDLCAKDFEDLFKQEESLKNIKDSLQQSSGRIDIIHSK
KTAALQSATPVERVKLQEALSQLDFQWEKVNKMYKDRQGRFDRSVEKWR -continued

RFHYDIKIFNQWLTEAEQFLRKTQIPENWEHAKYKWYLKELQDGIGQRQ

TVVRTLNATGEEIIQQSSKTDASILQEKLGSLNLRWQEVCKQLSDRKKR

LEEQKNILSEFQRDLNEFVLWLEEADNIASIPLEPGKEQQLKEKLEQVK

LLVEELPLRQGILKQLNETGGPVLVSAPISPEEQDKLENKLKQTNLQWI

KVSRALPEKQGEIEAQIKDLGQLEKKLEDLEEQLNHLLLWLSPIRNQLE

IYNQPNQEGPFDVQETEIAVQAKQPDVEEILSKGQHLYKEKPATQPVKR

KLEDLSSEWKAVNRLLQELRAKQPDLAPGLTTIGASPTQTVTLVTQPVV

TKETAISKLEMPSSLMLEVPALADFNRAWTELTDWLSLLDQVIKSQRVM

VGDLEDINEMIIKQKATMQDLEQRRPQLEELITAAQNLKNKTSNQEART

IITDRIERIQNQWDEVQEHLQNRRQQLNEMLKDSTQWLEAKEEAEQVLG

QARAKLESWKEGPYTVDAIQKKITETKQLAKDLRQWQTNVDVANDLALK

LLRDYSADDTRKVHMITENINASWRSIHKRVSEREAALEETHRLLQQFP

LDLEKFLAWLTEAETTANVLQDATRKERLLEDSKGVKELMKQWQDLQGE

IEAHTDVYHNLDENSQKILRSLEGSDDAVLLQRRLDNMNFKWSELRKKS

LNIRSHLEASSDQWKRLHLSLQELLVWLQLKDDELSRQAPIGGDFPAVQ

KQNDVHRAFKRELKTKEPVIMSTLETVRIFLTEQPLEGLEKLYQEPREL

PPEERAQNVTRLLRKQAEEVNTEWEKLNLHSADWQRKIDETLERLQELQ

EATDELDLKLRQAEVIKGSWQPVGDLLIDSLQDHLEKVKALRGEIAPLK

ENVSHVNDLARQLTTLGIQLSPYNLSTLEDLNTRWKLLQVAVEDRVRQL

HEAHRDFGPASQHFLSTSVQGPWERAISPNKVPYYINHETQTTCWDHPK

MTELYQSLADLNNVRFSAYRTAMKLRRLQKALCLDLLSLSAACDALDQH

NLKQNDQPMDILQIINCLTTIYDRLEQEHNNLVNVPLCVDMCLNWLLNV

YDTGRTGRIRVLSFKTGIISLCKAHLEDKYRYLFKQVASSTGFCDQRRL

GLLLHDSIQIPRQLGEVASFGGSNIEPSVRSCFQFANNKPEIEAALFLD

WMRLEPQSMVWLPVLHRVAAAETAKHQAKCNICKECPIIGFRYRSLKHF

NYDICQSCFFSGRVAKGHKMHYPMVEYCTPTTSGEDVRDFAKVLKNKFR

TKRYFAKHPRMGYLPVQTVLEGDNMETPVTLINFWPVDSAPASSPQLSH

DDTHSRIEHYASRLAEMENSNGSYLNDSISPNESIDDEHLLIQHYCQSL

NQDSPLSQPRSPAQILISLESEERGELERILADLEEENRNLQAEYDRLK

QQHEHKGLSPLPSPPEMMPTSPQSPRDAELIAEAKLLRQHKGRLEARMQ

ILEDHNKQLESQLHRLRQLLEQPQAEAKVNGTTVSSPSTSLQRSDSSQP

MLLRVVGSQTSDSMGEEDLLSPPQDTSTGLEEVMEQLNNSFPSSRGRNT

PGKPMREDTM

*homo sapiens* DMD amino acid sequence

---

What is claimed is:

1. A single stranded antisense oligonucleotide 16 to 25 nucleotides in length that comprises a base sequence of the sequence selected from the group consisting of SEQ ID NO: 5 to SEQ ID NO: 16, SEQ ID NO: 20 to SEQ ID NO: 28, SEQ ID NO: 30 to SEQ ID NO: 34, SEQ ID NO: 41, and SEQ ID NO: 46, wherein the antisense oligonucleotide induces skipping of exon 44 of human dystrophin pre-mRNA, and comprises a modification.

2. The antisense oligonucleotide according to claim 1, wherein said antisense oligonucleotide comprises the base sequence of the sequence SEQ ID NO: 5.

3. The antisense oligonucleotide according to claim 1, comprising a 2'-O-alkyl phosphorothioate antisense oligonucleotide.

4. The antisense oligonucleotide according to claim 3, wherein said antisense oligonucleotide comprises a 2'-O-methyl phosphorothioate ribose.

5. A viral-based vector, comprising a Pol III-promoter driven expression cassette for expression of an antisense oligonucleotide according to claim 1.

6. The antisense oligonucleotide of claim 1, wherein said modification comprises a modified backbone.

7. The antisense oligonucleotide according to claim 6, wherein the modified backbone is selected from the group consisting of a morpholino backbone, a carbamate backbone, a siloxane backbone, a sulfide backbone, a sulfoxide backbone, a sulfone backbone, a formacetyl backbone, a thioformacetyl backbone, a methyleneformacetyl backbone, a riboacetyl backbone, an alkene containing backbone, a sulfamate backbone, a sulfonate backbone, a sulfonamide backbone, a methyleneimino backbone, a methylenehydrazino backbone and an amide backbone.

8. The antisense oligonucleotide according to claim 1, wherein said modification is selected from the group consisting of: phosphorodiamidate morpholino oligomer (PMO), peptide nucleic acid, and locked nucleic acid.

9. The antisense oligonucleotide according to claim 2, wherein the antisense oligonucleotide is a PMO.

10. The oligonucleotide of claim 1, wherein said oligonucleotide is conjugated to a ligand.

11. The oligonucleotide of claim 10, wherein said ligand is a peptide.

12. The antisense oligonucleotide according to claim 1, wherein said modification comprises a locked nucleic acid (LNA).

* * * * *